United States Patent
Meyer et al.

(10) Patent No.: US 11,952,588 B2
(45) Date of Patent: Apr. 9, 2024

(54) METHODS FOR ALLOGENIC HEMATOPOIETIC STEM CELL TRANSPLANTATION

(71) Applicant: The Board of Trustees of the Leland Stanford Junior University, Stanford, CA (US)

(72) Inventors: Everett H. Meyer, Belmont, CA (US); Robert S. Negrin, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 919 days.

(21) Appl. No.: 16/967,375

(22) PCT Filed: Feb. 7, 2019

(86) PCT No.: PCT/US2019/017017
§ 371 (c)(1),
(2) Date: Aug. 4, 2020

(87) PCT Pub. No.: WO2019/157158
PCT Pub. Date: Aug. 15, 2019

(65) Prior Publication Data
US 2021/0030797 A1 Feb. 4, 2021

Related U.S. Application Data

(60) Provisional application No. 62/628,015, filed on Feb. 8, 2018.

(51) Int. Cl.
| | | |
|---|---|---|
| A61K 35/17 | (2015.01) | |
| A61K 31/436 | (2006.01) | |
| A61K 31/445 | (2006.01) | |
| A61K 35/28 | (2015.01) | |
| A61K 39/00 | (2006.01) | |
| A61P 35/02 | (2006.01) | |
| A61P 37/06 | (2006.01) | |
| C12N 5/0783 | (2010.01) | |
| C12N 5/0789 | (2010.01) | |
| A61K 35/12 | (2015.01) | |

(52) U.S. Cl.
CPC .......... *C12N 5/0647* (2013.01); *A61K 31/436* (2013.01); *A61K 31/445* (2013.01); *A61K 35/17* (2013.01); *A61K 35/28* (2013.01); *A61K 39/001* (2013.01); *A61P 35/02* (2018.01); *A61P 37/06* (2018.01); *C12N 5/0637* (2013.01); *A61K 2035/122* (2013.01); *C12N 2506/11* (2013.01)

(58) Field of Classification Search
None
See application file for complete search history.

(56) References Cited

U.S. PATENT DOCUMENTS

| | | |
|---|---|---|
| 5,806,529 A | 9/1998 | Reisner et al. |
| 8,632,768 B2 | 1/2014 | Ildstad et al. |
| 8,951,793 B2 | 2/2015 | Tran et al. |
| 9,452,184 B2 | 9/2016 | Ildstad et al. |
| 10,434,121 B2 | 10/2019 | Reisner et al. |
| 10,660,954 B2 | 5/2020 | Mitchell et al. |
| 10,842,821 B2 | 11/2020 | Deitcher |
| 10,881,692 B2 | 1/2021 | Deitcher |
| 11,447,747 B2 * | 9/2022 | Meyer .................. A61K 39/001 |
| 2005/0163760 A1 | 7/2005 | Cartier-Lacave et al. |
| 2009/0232774 A1 | 9/2009 | Reisner |
| 2012/0121539 A1 | 5/2012 | Sands et al. |
| 2014/0294793 A1 | 10/2014 | Littman et al. |
| 2015/0110738 A1 | 4/2015 | Horwitz |
| 2017/0073406 A1 | 3/2017 | Schurpf et al. |
| 2018/0251731 A1 | 9/2018 | Guillonneau et al. |
| 2019/0032013 A1 | 1/2019 | Leventhal |
| 2019/0183930 A1 | 6/2019 | Lamb et al. |
| 2019/0275079 A1 | 9/2019 | Ildstad et al. |
| 2019/0275085 A1 | 9/2019 | Deitcher et al. |

(Continued)

FOREIGN PATENT DOCUMENTS

| | | |
|---|---|---|
| EP | 2352816 B1 | 6/2015 |
| EP | 2606120 B1 | 10/2015 |

(Continued)

OTHER PUBLICATIONS

Duval, et al. (2010) "Hematopoietic Stem-Cell Transplantation for Acute Leukemia in Relapse or Primary Induction of Failure", Journal of Clinical Oncology, 28: 3730-38. (Year: 2010).*
Arai et al. (2015) "Increasing incidence of Chronic Graft versus-Host Disease in Allogeneic Transplantation: A Report from the Center for International Blood and Marrow Transplant Research" Biology of Blood Marrow Transplantation Journal American Society for Blood and Marrow Transplantation 21: 266-274.
Bhatia et al. (2007) "Late mortality after allogeneic hematopoietic cell transplantation and functional status of long-term survivors: report from the Bone Marrow Transplant Survivor Study" Blood 110: 3784-3792.

(Continued)

*Primary Examiner* — Robert M Kelly
(74) *Attorney, Agent, or Firm* — Pamela J. Sherwood; Bozicevic, Field and Francis LLP

(57) ABSTRACT

The disclosure provides methods for improved hematopoietic stem cell transplantations, including methods to enhance protection from graft versus host disease while maintaining effective immune responses such as graft versus tumor immune responses. The disclosure provides methods for administering, for example, hematopoietic stem and progenitor cells, regulatory T cells, and conventional T cells, wherein the conventional T cells are administered after the hematopoietic stem and progenitor cells and regulatory T cells. The disclosure also provides methods for administering, for example, hematopoietic stem and progenitor cells, regulatory T cells, and conventional T cells, wherein the regulatory T cells have not been cryopreserved prior to administration.

22 Claims, 12 Drawing Sheets

(56) References Cited

U.S. PATENT DOCUMENTS

| | | | |
|---|---|---|---|
| 2020/0002422 | A1 | 1/2020 | Sachs et al. |
| 2020/0016198 | A1 | 1/2020 | Jongen et al. |
| 2020/0030380 | A1 | 1/2020 | Ichim |
| 2020/0077644 | A1 | 3/2020 | Church et al. |
| 2020/0150108 | A1 | 5/2020 | Hill et al. |
| 2020/0179931 | A1 | 6/2020 | Foster et al. |
| 2021/0008200 | A1 | 1/2021 | Mitchell et al. |

FOREIGN PATENT DOCUMENTS

| | | |
|---|---|---|
| EP | 2558857 B1 | 9/2017 |
| EP | 3240803 A2 | 11/2017 |
| EP | 3340997 A1 | 7/2018 |
| EP | 2797421 B1 | 5/2020 |
| EP | 3676614 A1 | 7/2020 |
| WO | WO-2013130499 A1 | 9/2013 |
| WO | WO2015/066551 | 5/2015 |
| WO | WO2016139482 | 9/2016 |
| WO | WO-2018106610 A1 | 9/2018 |
| WO | WO-2018170335 A1 | 9/2018 |
| WO | WO-2019157158 A2 | 8/2019 |
| WO | WO-2020247341 A1 | 12/2020 |
| WO | WO-2022098926 A9 | 5/2022 |

OTHER PUBLICATIONS

Boyiadzis et al. (2015) "Impact of Chronic Graft-versus-Host Disease on Late Relapse and Survival on 7,489 Patients after Myeloablative Allogeneic Hematopoietic Cell Transplantation for Leukemia" Clinical Cancer Research, Journal American Association for Cancer Research 21:9 2020-2028.

Bradfield et al. (2004) "Graft-versus-leukemia effect in acute lymphoblastic leukemia: the importance of tumor burden and early detection" Leukemia 18: 1156-1158.

Gupta et al. (2010) "Comparable survival after HLA-well-matched unrelated or matched sibling donor transplantation for acute myeloid leukemia in first remission with unfavorable cytogenetics at diagnosis" Blood 116:11 1839-1848.

Hamilton et al. (2013) "Sustained disease-free survival achieved with withdrawal of immunosuppression after rapid relapse of myelodysplastic syndrome following myeloablative allogeneic hematopoietic transplantation: a case report" Journal of Medical Case Reports 7:18 4 pages.

Kanakry et al. (2014) "Single-agent GVHD prophylaxis with post-transplantation cyclophosphamide after myeloablative, HLA-matched BMT for AML, ALL, and MDS".

Kurosawa, et al. (2013) "Recent decrease in non-relapse mortality due to GVHD and infection after allogeneic hematopoietic cell transplantation in non-remission acute leukemia" Bone Marrow Transplantation 48: 1198-1204.

Srour et al. (2018) "Immunosuppression Withdrawal is an Effective Treatment of Relapse after Allogeneic Stem Cell Transplant for Myelofibrosis" Biology of Blood and Marrow Transplantation 24: S196-S197.

Storb et al. (1989) "Methotrexate and Cyclosporine Versus Cyclosporine Alone for Prophylaxis of Graft-Versus-Host Disease in Patients Given HLA-identical Marrow Grafts for Leukemia: Long-Term Follow-up of a Controlled Trial" Blood 73: 1729-1734.

Fowler, et al. In Vitro and In Vivo Sirolimus for Modulation of Allogeneic Hematopoietic Stem Cell Transplantation. Current Medicinal Chemistry-Immunology, Endocrine & Metabolic Agents 5.6 (2005): 555-564.

Gaidot, et al. Immune reconstitution is preserved in hematopoietic stem cell transplantation coadministered with regulatory T cells for GVHD prevention. Blood 117.10 (2011): 2975-2983.

U.S. Appl. No. 17/031,187 Office Action dated Feb. 5, 2021.
U.S. Appl. No. 17/031,187 Office Action dated Nov. 30, 2020.
U.S. Appl. No. 17/031,213 Office Action dated Jan. 15, 2021.

Zhao, et al. The cell composition of infused donor lymphocyte has different impact in different types of allogeneic hematopoietic stem cell transplantation. Clinical transplantation 28.8 (2014): 926-934.

Zorn, E. CD4+ CD25+ regulatory T cells in human hematopoietic cell transplantation. InSeminars in cancer biology Apr. 1, 2006 (vol. 16, No. 2, pp. 150-159). Academic Press.

Cutler, et al. Sirolimus for GVHD prophylaxis in allogeneic stem cell transplantation. Bone marrow transplantation 34.6 (2004): 471-476.

EP19750722.1 Extended European Search Report dated Oct. 15, 2021.

Fisher, Sheila A et al. Increased regulatory T cell graft content is associated with improved outcome in haematopoietic stem cell transplantation: a systematic review. British journal of haematology vol. 176,3 (2017): 448-463. doi:10.1111/bjh.14433.

PCT/US2021/058141 International Search Report and Written Opinion dated Jan. 14, 2022.

U.S. Appl. No. 17/031,187 Final Office Action dated Mar. 30, 2021.
U.S. Appl. No. 17/031,187 Office Action dated Nov. 1, 2021.
U.S. Appl. No. 17/031,213 Final Office Action dated Apr. 21, 2021.
U.S. Appl. No. 17/031,213 Notice of Allowance dated Feb. 17, 2022.
U.S. Appl. No. 17/031,213 Notice of Allowance dated May 27, 2022.
U.S. Appl. No. 17/031,213 Office Action dated Nov. 1, 2021.

Martelli et al. (2014) "HLA-haploidentical transplantation with regulatory and conventional T-cell adoptive immunotherapy prevents acute leukemia relapse", Key Points, Blood, vol. 124, No. 4, pp. 638-644.

Velardi et al. (2017) "Low-Toxicity/High-Efficacy HLA Haploidentical Transplantation for Elderly/Unfit Patients with Acute Leukemia", Blood, American Society of Hematology, vol. 130, p. 4601.

Aversa, et al. Full haplotype-mismatched hematopoietic stem-cell transplantation: a phase II study in patients with acute leukemia at high risk of relapse. Journal of Clinical Oncology 23.15 (2005): 3447-3454.

Aversa, et al. Haploidentical stem cell transplantation in leukemia. Blood reviews 15.3 (2001): 111-119.

Baker, et al. Comparative outcomes after haploidentical or unrelated donor bone marrow or blood stem cell transplantation in adult patients with hematological malignancies. Biology of Blood and Marrow Transplantation 22.11 (2016): 2047-2055.

Bashey, et al. Comparison of outcomes of hematopoietic cell transplants from T-replete haploidentical donors using post-transplantation cyclophosphamide with 10 of 10 HLA-A,-B,-C,-DRB1, and -DQB1 allele-matched unrelated donors and HLA-identical sibling donors: a multivariable analysis including disease risk index. Biology of Blood and Marrow Transplantation 22.1 (2016): 125-133.

Bensinger, et al. Transplantation of allogeneic CD34+ peripheral blood stem cells in patients with advanced hematologic malignancy. (1996): 4132-4138.

Blaise, et al. Haploidentical T cell-replete transplantation with post-transplantation cyclophosphamide for patients in or above the sixth decade of age compared with allogeneic hematopoietic stem cell transplantation from an human leukocyte antigen-matched related or unrelated donor. Biology of Blood and Marrow Transplantation 22.1 (2016): 119-124.

Bleakley, et al. Outcomes of acute leukemia patients transplanted with naive T cell-depleted stem cell grafts. The Journal of clinical investigation 125.7 (2015): 2677-2689.

Bluestone, et al. Type 1 diabetes immunotherapy using polyclonal regulatory T cells. Science translational medicine 7.315 (2015): 315ra189-315ra189.

Brunstein, et al. Umbilical cord blood-derived T regulatory cells to prevent GVHD: kinetics, toxicity profile, and clinical effect. Blood 127.8 (2016): 1044-1051.

Buckley, et al. Prognostic and therapeutic implications of minimal residual disease at the time of transplantation in acute leukemia. Received and accepted Jun. 19, 2012; Bone marrow transplantation 48.5 (2013): 630-641.

Burroughs, et al. Comparison of outcomes of HLA-matched related, unrelated, or HLA-haploidentical related hematopoietic cell trans-

(56) References Cited

OTHER PUBLICATIONS plantation following nonmyeloablative conditioning for relapsed or refractory Hodgkin lymphoma. Biology of blood and marrow transplantation 14.11 (2008): 1279-1287.
Champlin, et al. Haploidentical 'megadose'stem cell transplantation in acute leukemia: recommendations for a protocol agreed upon at the Perugia and Chicago meetings. Leukemia 16.3 (2002): 427-428.
Ciurea, et al. Haploidentical transplant with posttransplant cyclophosphamide vs matched unrelated donor transplant for acute myeloid leukemia. Blood 126.8 (2015): 1033-1040.
Cornelissen, et al. A randomized multicenter comparison of CD34+-selected progenitor cells from blood vs from bone marrow in recipients of HLA-identical allogeneic transplants for hematological malignancies. Experimental hematology 31.10 (2003): 855-864.
Devine, et al. Low risk of chronic graft-versus-host disease and relapse associated with T cell-depleted peripheral blood stem cell transplantation for acute myelogenous leukemia in first remission: Results of the Blood and Marrow Transplant Clinical Trials Network Protocol 0303. Biology of Blood and Marrow Transplantation 17.9 (2011): 1343-1351.
Di Stasi, et al. Similar transplantation outcomes for acute myeloid leukemia and myelodysplastic syndrome patients with haploidentical versus 10/10 human leukocyte antigen-matched unrelated and related Donors. Biology of Blood and Marrow Transplantation 20.12 (2014): 1975-1981.
Duong, et al. Peripheral blood progenitor cell mobilization for autologous and allogeneic hematopoietic cell transplantation: guidelines from the American Society for Blood and Marrow Transplantation. Biology of Blood and Marrow Transplantation 20.9 (2014): 1262-1273.
Gale, et al. Identical-twin bone marrow transplants for leukemia. Annals of internal medicine 120.8 (1994): 646-652.
Heinrichs, et al. Regulatory T-cell therapy for graft-versus-host disease. Journal of immunology research and therapy 1.1 (2016): 1-14.
Horowitz, et al. Graft-versus-leukemia reactions after bone marrow transplantation. (1990): 555-562.
Jakubowski, et al. T-cell depleted unrelated donor stem cell transplantation provides favorable disease-free survival for adults with hematologic malignancies. Biology of Blood and Marrow Transplantation 17.9 (2011): 1335-1342.
Johnston, et al. A phase I study of donor regulatory T cells as treatment for steroid dependent/refractory chronic graft versus host disease. Blood (2016): 385.
Kernan, et al. Clonable T lymphocytes in T cell-depleted bone marrow transplants correlate with development of graft-v-host disease. (1986): 770-773.
Kindwall-Keller, et al. The evolution of hematopoietic SCT in myelodysplastic syndrome. Bone marrow transplantation 43.8 (2009): 597-609.
Magenau et al., "Frequency of CD4+CD25hiFOXP3+Regulatory T Cells Has Diagnostic and Prognostic Value as a Biomarker for Acute Graft-versus-Host-Disease," Biol Blood Marrow Transplant 16:907-914, 2010.
Malard, et al. Larger number of invariant natural killer T cells in PBSC allografts correlates with improved GVHD-free and progression-free survival. Blood 127.14 (2016): 1828-1835.
Michallet, et al. Long-term outcome after allogeneic hematopoietic stem cell transplantation for advanced stage acute myeloblastic leukemia: a retrospective study of 379 patients reported to the Societe Francaise de Greffe de Moelle (SFGM). Bone marrow transplantation 26.11 (2000): 1157-1163.
Muffly, et al. Infusion of donor-derived CD8+ memory T cells for relapse following allogeneic hematopoietic cell transplantation. Blood advances 2.6 (2018): 681-690.
Muller, et al. Definition of a critical T cell threshold for prevention of GVHD after HLA non-identical PBPC transplantation in children. Bone marrow transplantation 24.6 (1999): 575-581.
Ogawa, et al. Impact of pretransplant leukemic blast% in bone marrow and peripheral blood on transplantation outcomes of patients with acute myeloid leukemia undergoing allogeneic stem cell transplantation in non-CR. Bone marrow transplantation 53.4 (2018): 478-482.
Olsson, et al. Primary graft failure after myeloablative allogeneic hematopoietic cell transplantation for hematologic malignancies. Leukemia 29.8 (2015): 1754-1762.
Pasquini, et al. Comparative outcomes of donor graft CD34+ selection and immune suppressive therapy as graft-versus-host disease prophylaxis for patients with acute myeloid leukemia in complete remission undergoing HLA-matched sibling allogeneic hematopoietic cell transplantation. Journal of clinical oncology 30.26 (2012): 3194-3201.
Ramlal, et al. Advances in the use of regulatory T-cells for the prevention and therapy of graft-vs.-host disease. Biomedicines 5.2 (2017): 23.
Razvani, et al. High donor FOXP3-positive regulatory T-cell (Treg) content is associated with a low risk of GVHD following HLA-matched allogeneic SCT. Blood 108.4 (2006): 1291-1297.
Rubio, et al. Early posttransplantation donor-derived invariant natural killer T-cell recovery predicts the occurrence of acute graft-versus-host disease and overall survival. Blood 120.10 (2012): 2144-2154.
Ruggeri, et al. Chemotherapy-Based HLA Haploidentical Transplantation with Treg/Tcon Immunotherapy in Unfit/Elderly Leukemia Patients: Powerful Gvl Effect and Insights from Animal Models. (2016): 3483-3483.
Saad, et al. Ex vivo T-cell depletion in allogeneic hematopoietic stem cell transplant: past, present and future. Bone marrow transplantation 52.9 (2017): 1241-1248.
Shlomchik, et al. Graft-versus-host disease. Nature Reviews Immunology 7.5 (2007): 340-352.
Shook, et al. Haploidentical stem cell transplantation augmented by CD45RA negative lymphocytes provides rapid engraftment and excellent tolerability. Pediatric Blood & Cancer 62.4 (2015): 666-673.
Sureda, et al. Indications for allo-and auto-SCT for haematological diseases, solid tumours and immune disorders: current practice in Europe, 2015. Bone marrow transplantation 50.8 (2015): 1037-1056.
Theil, et al. Adoptive transfer of allogeneic regulatory T cells into patients with chronic graft-versus-host disease. Cytotherapy 17.4 (2015): 473-486.
Touzot, et al. CD45RA depletion in HLA-mismatched allogeneic hematopoietic stem cell transplantation for primary combined immunodeficiency: A preliminary study. Journal of Allergy and Clinical Immunology 135.5 (2015): 1303-1309.
Triplett et al., "Rapid memory T-cell reconstitution recapitulating CD45RA-depleted haploidentical transplant graft content in patients with hematologic malignancies" Bone Marrow Transplantation 50:968-977, 2015.
Urbano-Ispizua, et al. Risk factors for acute graft-versus-host disease in patients undergoing transplantation with CD34+ selected blood cells from HLA-identical siblings. Blood, the Journal of the American Society of Hematology 100.2 (2002): 724-727.
Brunstein, et al. "Infusion of ex vivo expanded T regulatory cells in adults transplanted with umbilical cord blood: safety profile and detection kinetics." Blood, the Journal of the American Society of Hematology 117.3 (2011): 1061-1070.
Co-pending U.S. Appl. No. 17/031,187, inventors Meyer; Everett Hurteau et al., filed Sep. 24, 2020.
Co-pending U.S. Appl. No. 17/031,213, inventors Meyer; Everett Hurteau et al., filed Sep. 24, 2020.
Di Ianni, et al. "Tregs prevent GVHD and promote immune reconstitution in HLA-haploidentical transplantation." Blood, the Journal of the American Society of Hematology 117.14 (2011): 3921-3928.
Edinger, et al. "CD4+ CD25+ regulatory T cells preserve graft-versus-tumor activity while inhibiting graft-versus-host disease after bone marrow transplantation." Nature medicine 9.9 (2003): 1144-1150.

(56) References Cited

OTHER PUBLICATIONS

Florek, et al. "Freeze and thaw of CD4+ CD25+ Foxp3+ regulatory T cells results in loss of CD62L expression and a reduced capacity to protect against graft-versus-host disease." PLoS One 10.12 (2015).

Martelli, et al. "HLA-haploidentical transplantation with regulatory and conventional T-cell adoptive immunotherapy prevents acute leukemia relapse." Blood, the Journal of the American Society of Hematology 124.4 (2014): 638-644.

Meyer, E. Phase 1-2 MAHCT w/ TCell Depleted Graft wl Simultaneous Infusion Conventional and Regulatory T Cell. U.S. National Library of Medicine. ClinicalTrials.gov Identifier: NCT01660607. Aug. 8, 2012; Last updated Jun. 14, 2019. Available at https://clinicaltrials.gov/ct2/show/record/NCT01660607?view=record. Accessed May 7, 2020.

Meyer, E. Conventional and Regulatory T Cells in Treating Patients with Advanced Hematologic Malignancies Undergoing T Cell-Depleted Donor Stem Cell Transplant. National Cancer Institute. Available at https://www.cancer.gov/about-cancer/treatment/clinical-trials/search/v?id=NCI-2011-03025&r=1 . Accessed on May 7, 2020.

Meyer, E. Haploidentical Allogeneic Transplant With Posttransplant Infusion of Regulatory Tcells. U.S. National Library of Medicine. ClinicalTrials.gov Identifier: NCT01050764. Jan. 15, 2010. Last updated Jun. 27, 2018. Available at https://clinicaltrials.gov/ct2/show/record/NCT01050764. Accessed on May 7, 2020.

Meyer, et al. "Phase I/II Trial for Patients with Advanced Hematologic Malignancies Undergoing Myeloablative Allogeneic HCT with a T Cell Depleted Graft with Infusion of Conventional T Cells and Regulatory T Cells." Biology of Blood and Marrow Transplantation 24.3 (2018): S171.

Nguyen, et al. "In vivo dynamics of regulatory T-cell trafficking and survival predict effective strategies to control graft-versus-host disease following allogeneic transplantation." Blood 109.6 (2007): 2649-2656.

PCT/US2019/017017 International Search Report dated Apr. 19, 2019.

Trzonkowski, et al. "First-in-man clinical results of the treatment of patients with graft versus host disease with human ex vivo expanded CD4+ CD25+ CD127-T regulatory cells." Clinical immunology 133.1 (2009): 22-26.

Pidala et al., 2009, "Sirolimus as primary treatment of acute graft-versus-host disease following allogeneic hematopoietic cell transplantation" Bioi. Blood. Marrow. Transplant. vol. 15: 881-885.

Tang et al. "CD4+Foxp3+ Regulatory T Cell Therapy in Transplantation," Journal of Molecular 1-3, 53-55, 105-107 Cell Biology, vol. 4, pp. 11-21.

Lu at el. (2010) "Characterization of Protective Human CD-1+ CD25+FOXP3+ Regulatory T Cells G3-GG Generated with IL-2, TGF-b and Retinoic Acid," PLoS One, vol. 5, Iss. 12, e15150, pp. 1-12.

Mehrotra et al. (2010) "Amelioration of a Mouse Model of Osteogenesis Imperfecta with 1-3, 53-55, 105-107 Hematopoietic Stem Cell Transplantation: Micro-Computed Tomography Studies," Exp Hematol, . 38, No. 7, pp. 593-602.

\* cited by examiner

| Subject | Age | Sex | CMV (D/R) | Cohort | Conditioning | GVHD PPx | Disease status at transplant |
|---|---|---|---|---|---|---|---|
| 5126 | 56 | M | -/+ | 1 | TBI/Cy/VP-16 | None | AML, active disease |
| 5201 | 61 | F | -/- | 1A | TBI/Cy/VP-16 | None | AML, CR2 |
| 5534 | 65 | M | -/- | 1A | TBI/Cy/VP-16 | None | MDS, RAEB2, active disease |
| 5902 | 45 | F | +/+ | 1A | BCNU/VP-16/Cy | None | Gamma delta NHL, active disease |
| 6157 | 51 | M | +/+ | 1A | TBI/Cy/VP-16 | None | AML, active disease |
| 6666 | 49 | M | -/- | 1A | BCNU/VP-16/Cy | Sirolimus | Refractory NHL, active disease |
| 6708 | 42 | M | +/- | 2A | Bu/Cy | Sirolimu | FLT3+ AML, CR2 |
| 6784 | 34 | M | +/+ | 2A | TBI/Cy/VP-16 | Sirolimus | ETP-ALL, active disease |
| 6820 | 20 | M | +/+ | 2A | Bu/Cy | Tacrolimus | ALL, CR2 (MRD+) |
| 6857 | 54 | M | +/- | 2A | Bu/Cy | Tacrolimus | CML blast crisis, active disease |
| 6948 | 53 | M | -/- | 2A | Bu/Cy | Tacrolimus | AML, CR2 |
| 7011 | 56 | M | +/- | 2A | Bu/Cy | Tacrolimus | MF, active disease |

FIG. 1

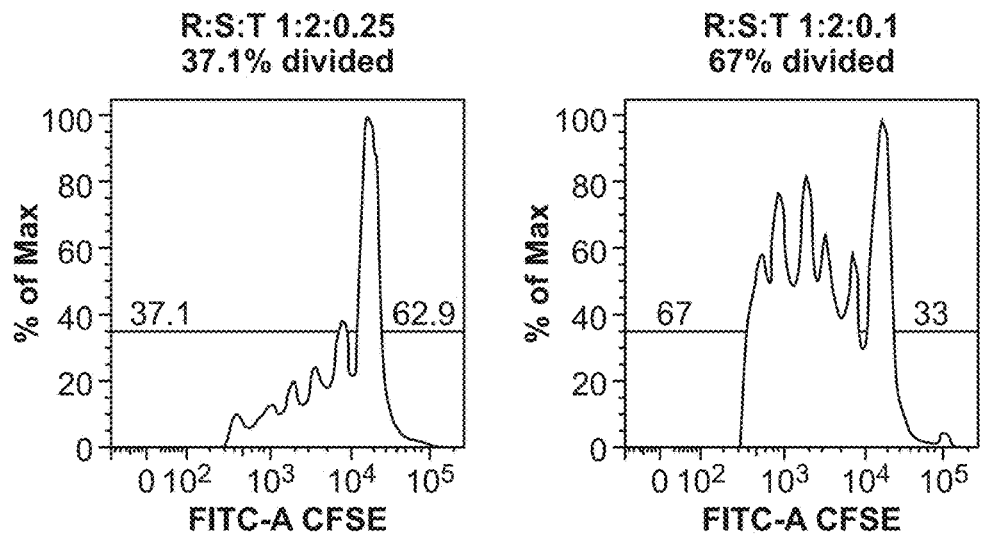
FIG. 4B (Cont.)
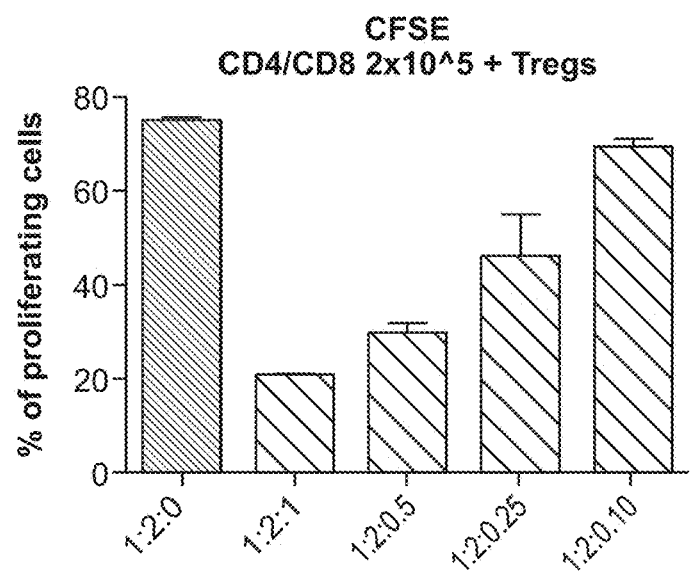
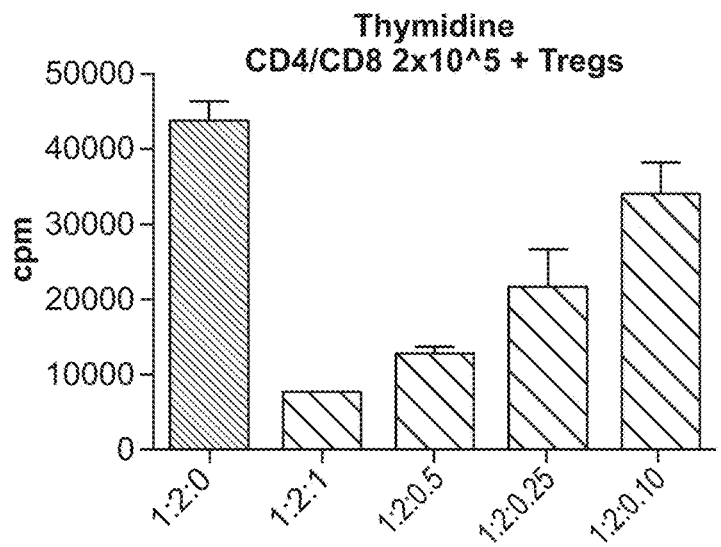
FIG. 4C

| | Patient | %FoxP3+ Post-Sort | T_reg Count Post-Sort | T_reg Count Pre-Sort | %Recovery |
|---|---|---|---|---|---|
| Initial protocol: Frozen T_reg | 5126 | 96 | $156 \times 10^6$ | $101 \times 10^6$ | 64.7 |
| | 5201 | 96 | $150 \times 10^6$ | $130 \times 10^6$ | 86.6 |
| | 5534 | 91 | $150 \times 10^6$ | $112 \times 10^6$ | 74.7 |
| | 5902 | 96 | $82 \times 10^6$ | $72 \times 10^6$ | 87.8 |
| | 6157 | 94 | $234 \times 10^6$ | $120 \times 10^6$ | 51.2 |
| Modified protocol: Fresh T_reg | 6666 | 94 | $111 \times 10^6$ | $73 \times 10^6$ | 65.8 |
| | 6708 | 96 | $137 \times 10^6$ | $72 \times 10^6$ | 52.2 |
| | 6784 | 94 | $130 \times 10^6$ | $66 \times 10^6$ | 50.7 |
| | 6820 | 92 | $159 \times 10^6$ | $105 \times 10^6$ | 66.0 |
| | 6857 | 92 | $293 \times 10^6$ | $191 \times 10^6$ | 79.9 |
| | 6948 | 95 | $162 \times 10^6$ | $110 \times 10^6$ | 67.9 |
| | 7011 | 92 | $67 \times 10^6$ | $50 \times 10^6$ | 74.6 |

FIG. 7

| | Subject | T$_{reg}$ dose/kg | T$_{con}$ dose/kg | CD34$^+$ dose/kg |
|---|---|---|---|---|
| Initial protocol: Frozen T$_{reg}$ | 5126 | 1.0 x 10$^6$ | 3.0 x 10$^6$ | 4.6 x 10$^6$ |
| | 5201 | 1.0 x 10$^6$ | 1.0 x 10$^6$ | 4.2 x 10$^6$ |
| | 5534 | 1.0 x 10$^6$ | 1.0 x 10$^6$ | 3.6 x 10$^6$ |
| | 5902 | 1.0 x 10$^6$ | 1.0 x 10$^6$ | 4.9 x 10$^6$ |
| | 6157 | 1.0 x 10$^6$ | 1.0 x 10$^6$ | 7.4 x 10$^6$ |
| Modified protocol: Fresh T$_{reg}$ | 6666 | 1.0 x 10$^6$ | 1.0 x 10$^6$ | 1.2 x 10$^6$ |
| | 6708 | 2.4 x 10$^6$ | 3.0 x 10$^6$ | 14.7 x 10$^6$ |
| | 6784 | 2.5 x 10$^6$ | 3.0 x 10$^6$ | 5.8 x 10$^6$ |
| | 6820 | 2.3 x 10$^6$ | 3.0 x 10$^6$ | 15.9 x 10$^6$ |
| | 6857 | 3.0 x 10$^6$ | 3.0 x 10$^6$ | 6.8 x 10$^6$ |
| | 6948 | 2.6 x 10$^6$ | 3.0 x 10$^6$ | 3.6 x 10$^6$ |
| | 7011 | 2.5 x 10$^6$ | 3.0 x 10$^6$ | 5.2 x 10$^6$ |

FIG. 8

| | Subject | Disease | Disease status at transplant | aGVHD | cGVHD | Disease relapse | Status at last follow-up | SAE(s) |
|---|---|---|---|---|---|---|---|---|
| Initial protocol: Frozen T_reg | 5126 | AML | Refractory disease | Yes, grade 3 GI and liver | N/A | Persistent disease | Day+56, deceased | Severe pulmonary infection |
| | 5201 | AML | CR2 | Yes, grade 3 skin and liver | Mild, Day+474 | None | Day+1887, remission | CMV reactivation |
| | 5534 | MDS, RAEB2 | Refractory disease | None | N/A | Persistent disease | Day+64, deceased | Graft loss Fungal pneumonia |
| | 5902 | Gamma delta NHL | Refractory disease | Yes, grade 1 skin | Mild, Day+145 | None | Day+1184, remission | Gram negative bacteremia |
| | 6157 | AML | Refractory disease | Yes, grade 1 skin | None | Day+175 | Day+212, deceased | Acute diverticulitis, HHV6 viremia |
| | 6666 | Refractory NHL | Refractory disease | None | None | Persistent disease | Day+236, remission, deceased D+247 | CoNS bacteremia |
| | 6708 | FLT3+ AML | CR2 | None | None | Day+483 | Day+635, remission | Mild VOD |
| | 6784 | ETP-ALL | Refractory disease | None | None | None | Day+529, remission | Herpes labialis |
| Modified protocol: Fresh T_reg | 6820 | ALL | CR2 (MRD+) | None | None | None | Day+501, remission | Acute cholecystitis Disseminated candidiasis CMV reactivation |
| | 6857 | CML blast crisis | Refractory disease | None | None | Persistent disease | Day+539 | Coronavirus URI |
| | 6948 | AML | CR2 | None | None | None | Day+447, remission | Unspecified transaminitis |
| | 7011 | MF | Refractory disease | None | None | None | Day+411, remission | Strep mitis bacteremia |

FIG. 9

METHODS FOR ALLOGENIC HEMATOPOIETIC STEM CELL TRANSPLANTATION

CROSS REFERENCE

This application claims the benefit and is a 371 application of PCT Application No. PCT/US2019/017017, filed Feb. 7, 2019, which claims benefit of United States Provisional Application No. 62/628,015, filed Feb. 8, 2018, which is are incorporated herein by reference in its their entirety.

GOVERNMENT SUPPORT REASEARCH

This invention was made with Government support under HL114591 awarded by the National Institutes of Health. The Government has certain rights in the invention.

BACKGROUND

Patients with high risk hematologic malignancies such as leukemia and lymphoma beyond first remission or with refractory relapse are rarely cured with standard chemotherapy. Myeloablative allogeneic hematopoietic cell transplantation (HCT) is associated improved survival in these patients, with disease free survival ranging from 10-50% and non-relapse mortality ranging from 30 to 50%. The early morbidity and mortality associated with acute graft versus host disease (aGVHD) is a major factor limiting the success of HCT, as is the long-term morbidity associated with chronic GVHD.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Disclosed herein, in some embodiments, is a method of treating a human subject in need thereof, comprising administering to said human subject: a) a population of hematopoietic stem and progenitor cells (HSPCs); b) a population of cells comprising regulatory T cells (Tregs); and c) a population of conventional T cells (Tcons); wherein said population of HSPCs and said population of cells comprising Tregs are administered prior to said population of Tcons; and wherein said population of cells comprising Tregs has not been cryopreserved prior to said administering of said population of cells comprising Tregs.

Disclosed herein, in some embodiments, is a method of treating a human subject in need thereof, comprising administering to said human subject: a) a population of hematopoietic stem and progenitor cells (HSPCs); b) a population of cells comprising regulatory T cells (Tregs); and c) a population of conventional T cells (Tcons); wherein said population of HSPCs and said population of cells comprising Tregs are administered prior to said population of conventional T cells; and wherein said human subject does not develop graft versus host disease (GVHD) within 30 days after said administering of said population of Tcons.

Disclosed herein, in some embodiments, is a method of treating a human subject in need thereof, comprising administering to said human subject: a) a population of hematopoietic stem and progenitor cells (HSPCs); b) a population of cells comprising regulatory T cells (Tregs); and c) a population of conventional T cells (Tcons); wherein said population of HSPCs and said population of cells comprising Tregs are administered prior to said population of Tcons; wherein said population of cells comprising Tregs comprises $CD45^+$ cells, wherein more than 90% of said $CD45^+$ cells are Tregs.

BRIEF DESCRIPTION OF THE DRAWINGS

FIG. 1 provides patient characteristics from a clinical trial comprising administering HSPCs and Tregs prior to Tcons.

FIG. 7 shows the cell dose yields of Tregs from donors in the clinical trial.

FIG. 8 provides cell dosing details for subjects in the clinical trial.

FIG. 9 summarizes clinical outcome data from the clinical trial.

DETAILED DESCRIPTION

Figure 2A:
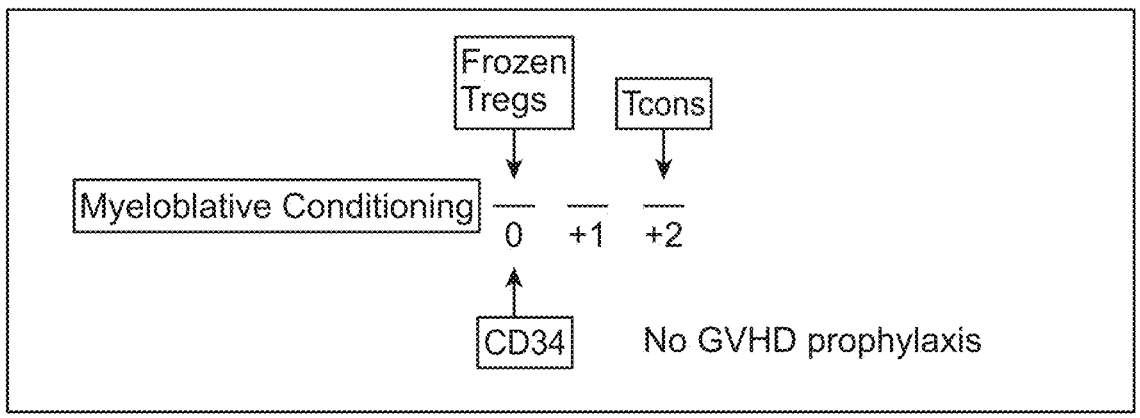
FIG. 2 illustrates original and modified clinical protocol schemas.

The following description and examples illustrate embodiments of the invention in detail. It is to be understood that this invention is not limited to the particular embodiments described herein and as such can vary. Those of skill in the art will recognize that there are numerous variations and modifications of this invention, which are encompassed within its scope.

As used herein, the singular forms "a," "an," and "the" include plural referents unless the context clearly dictates otherwise.

The term "about" and its grammatical equivalents in relation to a reference numerical value and its grammatical equivalents as used herein can include a range of values plus or minus 10% from that value. For example, the amount "about 10" includes amounts from 9 to 11. The term "about" in relation to a reference numerical value can also include a range of values plus or minus 10%, 9%, 8%, 7%, 6%, 5% 4%, 3%, 2%, or 1% from that value.

Overview

Provided herein are methods for improved allogenic hematopoietic stein cell transplantation (HCT). In some embodiments, the methods disclosed herein retain graft-versus-tumor (GVT) effects of HCT administered to a subject with a cancer, while preventing or reducing graft versus host disease (GVHD).

HCT is the transplantation of multipotent hematopoietic stem and progenitor cells (HSPCs), usually derived from donor bone marrow, peripheral blood, or umbilical cord blood, into a recipient. The recipient can be subjected to myeloablative conditioning, which can kill hematopoietic cells including tumor cells and host immune cells. The HSPCs transferred into the recipient can then reconstitute the hematopoietic compartment. HCT can be useful as a treatment for cancer due to the ability of donor T cells to exert anti-tumor effects, referred to as graft versus tumor (GVT). In patients with hematologic malignancies that are refractory to chemotherapy, HCT is associated with improved survival.

However, donor T cells can also attack non-tumor host cells, resulting in graft versus host disease (GVHD). GVHD is a major source of post-HCT complications, and can be fatal. Management of GVHD can require immunosuppressive therapy or cytotoxic mediations, which can cause toxicity, increase susceptibility to infection, or blunt anti-tumor immunity. The early morbidity and mortality associated with acute graft versus host disease (aGVHD) is a major factor limiting the success of HCT, as is the long-term morbidity associated with chronic GVHD (cGVHD). GVHD is a risk for both HLA-matched and -mismatched transplantations. GVKD can occur even if the donor and recipient are ILA-matched, because the immune system can still recognize other differences between their tissues. The incidence of aGVHD following allogeneic HCT from an HLA-matched sibling donor (MSD) is 20 to 60%, despite the use of various immunosuppressive agents.

Both GVT and GVHD are largely mediated by conventional T cells (Tcons), which mount immune responses upon recognition of cognate antigen by T cell receptors. Depleting T cells from HCT grafts can reduce GVHD, but can also result in reduced GVT and increased likelihood of cancer relapse. Besides Tcons, Tregs are an additional subset of T cells that negatively regulate inflammation and promote immune tolerance. Tregs can prevent or reduce GVHD through their negative regulation of inflammation, including, for example, inflammation elicited by donor Tcons recognizing recipient antigens.

Provided herein are methods for improved HCT, comprising administering to a subject certain populations of cells, including a population comprising HSPCs, a population comprising Tregs, and a population comprising Tcons. Without wishing to be bound by theory, administering Tregs can reduce GVHD, while administering Tcons enhances GVT; thus, the present disclosure provides methods for administering both to enhance GVT while minimizing GVHD. Without wishing to be bound by theory, these beneficial aspects of the present invention may be linked to the order of administering cells as described herein (e.g., administration of Tregs prior to Tcons), or to a lack of cryopreservation of Tregs prior to administration. Accordingly, the methods disclosed herein can retain the graft-versus-tumor (GVT) effects of HCT administered to a subject with a cancer, while preventing or reducing graft versus host disease (GVHD). In some embodiments, two or more populations of cells are administered at different times, for example, HSPCs and Tregs can be administered prior to Tcons.

One or more populations of cells can be fresh, and one or more populations of cells can be cryopreserved prior to thawing and administering to a subject. Without wishing to be bound by theory, administering fresh Tregs can reduce GVHD in a subject, and/or administering cryopreserved Tcons can reduce GVHD in a subject. For example, administering cryopreserved Tcons after fresh Tregs can reduce GVHD in a subject, promote GVT in a subject, or promote GVT in a subject in the absence of GVHD.

The present disclosure also provides a population of cells comprising Tregs that is sorted to generate a population of cells comprising a high percentage of Tregs. In some embodiments, administering a population of cells comprising a high percentage of fresh Tregs prior to administering Tcons reduces GVHD in a subject.

Hematopoietic Cell Transplantation and Cancer

Provided herein are methods wherein a recipient subject having a cancer receives a hematopoietic stem cell transplantation (HCT). The HCT can be useful for treating or reducing cancer in the subject. In some embodiments, a population of conventional T cells (Tcons) is administered to the subject in order to elicit graft-versus-tumor (GVT) immune responses.

Patients with high risk hematologic malignancies are rarely cured with standard chemotherapy. High risk malignancies include, for example, leukemia or lymphoma that has progressed beyond first remission, or leukemia or lymphoma with refractory relapse. Myeloablative allogeneic hematopoietic stem cell transplantation (HCT) is associated improved survival in these patients, with disease free survival ranging from 10-50% and non-relapse mortality ranging from 30 to 50%.

Hematopoietic stem cell transplantation (HCT) is the transplantation of multipotent hematopoietic stein and progenitor cells (HSPCs), usually derived from bone marrow, peripheral blood, or umbilical cord blood. HSPCs can have extensive self-renewal capacity, and an ability to differentiate into specialized cell types, for example, an ability to reconstitute all hematopoietic cell lineages. HSPCs can undergo asynchronous replication, where two daughter cells are produced with different phenotypes. Hematopoietic stem cells can exist in a mitotically quiescent form.

HSPCs can be obtained by harvesting from bone marrow or from peripheral blood. Bone marrow can be aspirated from the posterior iliac crest or the anterior iliac crest while the donor is under either regional or general anesthesia. HSPCs can be obtained by harvesting from peripheral blood, for example, by peripheral blood apheresis. The number of stein cells harvested can be increased by treating the donor with a mobilization agent, i.e. an agent that mobilizes stem cells from the bone marrow into peripheral blood. Non-limiting examples of mobilization agents include granulocyte colony-stimulating factor (G-CSF), granulocyte macrophage colony-stimulating factor (GM-CSF), mozobil, and combinations thereof. Techniques to mobilize stem cells into peripheral blood can comprise administering to a donor, for example, 10 to 40 µ/kg/day of a mobilization agent. A mobilization agent can be administered to the donor in, for example, 1, 2, 3, 4, 5, 6, 7, 8, 9, or 10 doses. An apheresis product can be isolated from a donor about, for example, 1, 2, 3, 4, 5, 6, 7, 8, 9, 10, 11, 12, 13, 14, 15, 16, 17, 18, 19, 20, 21, 22, 23, 24, 26, 28, or 30 hour(s) after a dose of mobilization agent.

The methods of the disclosure can be used for treating a human subject with a cancer. In some embodiments, the subject has been treated for cancer, e.g. by treatment with a chemotherapeutic drug or with radiation. The methods of the disclosure can be useful for treating, a hematologic malignancy, for example, leukemia or lymphoma. Examples of hematologic malignancies that can be treated by the methods of the disclosure include, but are not limited to, acute lymphocytic leukemia (ALL), acute myelogenous leukemia (AML), chronic myelogenous leukemia (CML), multiple myeloma, and lymphomas such as Hodgkin and non-Hodgkin lymphomas. A cancer can be a solid tumor. In some embodiments, the cancer is a primary or metastatic tumor.

The types of cancer that can be treated using the methods of the present invention include but are not limited to leukemia, lymphoma, adrenal cortical cancer, anal cancer, aplastic anemia, bile duct cancer, bladder cancer, bone cancer, bone metastasis, brain cancers, central nervous system (CNS) cancers, peripheral nervous system (PNS) cancers, breast cancer, cervical cancer, childhood Non-Hodgkin's lymphoma, colon and rectum cancer, endometrial cancer, esophagus cancer, Ewing's family of tumors (e.g. Ewing's sarcoma), eye cancer, gallbladder cancer, gastrointestinal carcinoid tumors, gastrointestinal stromal tumors, gestational trophoblastic disease, hairy cell leukemia, Hodgkin's lymphoma, Kaposi's sarcoma, kidney cancer, laryngeal and pharyngeal cancer, acute lymphocytic leukemia, acute myeloid leukemia, children's leukemia, chronic lymphocytic leukemia, chronic myeloid leukemia, liver cancer, lung cancer, lung carcinoid tumors, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcomas, melanoma skin cancer, non-melanoma skin cancers, stomach cancer, testicular cancer; thymus cancer, thyroid cancer, uterine cancer (e.g. uterine sarcoma), transitional cell carcinoma, vaginal cancer, vulvar cancer, mesothelioma, squamous cell or epidermoid carcinoma, bronchial adenoma, choriocarinoma, head and neck cancers, teratocarcinoma, and Waldenstrom's macroglobulinemia.

Hematopoietic Cell Transplantation and Graft Versus Host Disease

The present disclosure provides methods for improved hematopoietic stem cell transplantation (HCT), wherein GVHD is reduced or prevented. In some embodiments, an HCT recipient subject is administered populations of cells described herein, and the recipient subject does not develop GVHD within certain spans of time after administration of the cells (e.g, within 30, 100, or 200 days). For example, populations of cells described herein can be administered to an HCT recipient subject, and the likelihood of the recipient subject developing GVHD can be reduced within certain spans of time after administration of the cells, relative to a subject receiving HCT according to a different protocol (e.g., within 30, 100, or 200 days). A population of cells comprising Tregs can be administered to an HCT recipient subject, and the population of Tregs can serve to reduce or prevent GVHD in the HCT recipient subject. A population of cells comprising fresh Tregs can be administered to an HCT recipient subject, and can serve to reduce or prevent GVHD in the HCT recipient subject. In some embodiments, a population of cells comprising a high proportion of Tregs (e.g., CD4+FOXP3+ or CD4+CD25+CD127dim cells) is administered to an HCT recipient subject, and serves to reduce or prevent GVHD in the HCT recipient subject.

Graft-versus-host disease (GVHD) is an inflammatory disease that can occur in the allogenic transplant setting. GVHD involves donor cells (graft) attacking recipient cells (host). GVHD can be classified into acute GVHD (aGVHD) and chronic GVHD (cGVHD). aGVHD typically occurs in the first 3 months after transplantation. aGVHD can be life-threatening and can involve, for example, the skin, the intestines, and/or the liver. cGVHD typically occurs after the first 3 months following transplant. cGVHD is a major source of late treatment-related complications, and can be life-threatening. In addition to inflammation, cGVHD can lead to the development of fibrosis, which can result in functional disability.

The early morbidity and mortality associated with acute graft versus host disease (aGVHD) is a major factor limiting the success of HCT, as is the long-term morbidity associated with chronic GVHD (cGVHD). The incidence of aGVHD following allogeneic HCT from an HLA-matched sibling donor (MSD) is 20 to 60%, despite the use of various immunosuppressive agents such as tacrolimus, cyclosporine, methotrexate, mycophenolate, anti-thymocyte globulin and corticosteroids. Approximately one-third of patients who undergo allogeneic HCT using a MSD and a T cell replete graft will develop chronic GVHD.

GVHD severity can be graded, for example, using the Glucksberg grade (I-IV) or the International Bone Marrow Transplant Registry (IBMTR) grading system (A-D). The severity of acute GVHD is determined by an assessment of the degree of involvement of the skin, liver, and gastrointestinal tract. The stages of individual organ involvement are combined with (Glucksberg) or without (IBMTR) the patient's performance status to produce an overall grade, which can have prognostic significance. Grading is important in terms of assessing the response to prophylaxis or treatment, impact upon survival, and association with graft-versus-leukemia effect.

Grade I(A) GVHD is characterized as mild disease, grade II(B) GVHD as moderate, grade III(C) as severe, and grade IV(D)life-threatening. The IBMTR grading system defines the severity of acute GVHD as follows: Grade A: stage 1 skin involvement alone (maculopapular rash over <25 percent of the body) with no liver or gastrointestinal involvement; Grade B: stage 2 skin involvement, stage 1 to 2 gut or liver involvement; Grade C: stage 3 involvement of any organ system (generalized erythroderma; bilirubin 6.1 to 15.0 mg/dL; diarrhea 1500 to 2000 mL/day); Grade D: stage 4 involvement of any organ system (generalized erythroderma with bullous formation; bilirubin >15 mg/dL; diarrhea >2000 mL/day OR pain OR ileus). Patients with moderate to severe GVHD have a significantly higher mortality rate compared with those with milder disease, for example, estimated five year survival for patients with grade III (C) aGVHD is 25%, while for patients with grade IV (D) estimated five year survival is 5%.

Management of GVHD may require immunosuppressive therapy (for example, high dose corticosteroids, prolonged administration of immunosuppressants) or cytotoxic mediations, all of which are associated with toxicity. In many cases, immunosuppressive therapies can fail to effectively treat GVHD, or can result in increased susceptibility to infection, or blunted anti-tumor immunity.

In some embodiments, the methods disclosed herein prevent or reduce GVHD in an HCT recipient subject. For example, the methods disclosed herein can prevent any manifestation of GVHD in a subject receiving HCT.

The methods disclosed herein can prevent, for example, any GVHD of stage 1 or above, any GVHD of stage 2 or above, any GVHD of stage 3 or above, or any GVHD of stage 4 in subjects receiving HCT.

In some embodiments, the methods disclosed herein prevent any GVHD of stage 1, 2, 3, or 4 in subjects receiving HCT for greater than at least about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 365, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900, 950, 1000, or more days after administering a population of cells as disclosed herein.

The present disclosure provides methods that can prevent any GVHD of stage 1, 2, 3, or 4 in subjects receiving HCT for at most about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 365, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900, 950, 1000, or less days after administering a population of cells as disclosed herein.

The present disclosure provides methods that can prevent, for example, any GVHD of grade A or above, any GVHD of grade B or above, any GVHD of grade C or above, or any GVHD of grade D in subjects receiving HCT.

In some embodiments, the methods described herein can prevent any GVHD of grade A, B, C, or D in subjects receiving HCT for greater than at least about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 365, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900, 950, 1000, or more days after administering a population of cells as disclosed herein.

The present disclosure provides methods that can prevent any GVHD of grade A, B, C, or D in subjects receiving HCT for at most about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 365, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900, 950, 1000, or less days after administering a population of cells as disclosed herein.

The methods disclosed herein can reduce, for example, the proportion of HCT recipient subjects exhibiting GVHD of stage 1 or above, stage 2 or above, stage 3 or above, or stage 4 relative to other HCT methods.

The methods disclosed herein can, for example, reduce the proportion of HCT recipient subjects exhibiting GVHD of stage 1 or above, stage 2 or above, stage 3 or above, or stage 4, for greater than at least about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 365, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900, 950, 1000, or more days after administering a population of cells as disclosed herein, relative to other HCT methods.

In some embodiments, the methods disclosed herein reduce the proportion of HCT recipient subjects exhibiting GVHD of stage 1 or above, stage 2 or above, stage 3 or above, or stage 4, for at most about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 365, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900, 950, 1000, or less days after administering a population of cells as disclosed herein, relative to other HCT methods.

Disclosed herein are methods that can, for example, reduce the proportion of HCT recipient subjects exhibiting GVHD of grade A or above, grade B or above, grade C or above, or grade D relative to other HCT methods.

The methods disclosed herein can, for example, reduce the proportion of HCT recipient subjects exhibiting GVHD of grade A or above, grade B or above, grade C or above, or grade D, for greater than at least about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 365, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900, 950, 1000, or more days after administering a population of cells as disclosed herein, relative to other HCT methods.

In some embodiments, the methods disclosed herein reduce the proportion of HCT recipient subjects exhibiting GVHD of grade A or above, grade B or above, grade C or above, or grade D, for at most about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 365, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900, 950, 1000, or less days after administering a population of cells as disclosed herein, relative to other HCT methods.

Immune Cells in HCT and GVHD

Provided herein are methods for improved hematopoietic stem cell transplantation (HCT), wherein GVHD is reduced or prevented as compared to, for example, a comparable method of treatment wherein Tcons are not administered after HSPCs and/or Tregs, or wherein the Tregs are cryopreserved, or wherein the Tcons are not cryopreserved, or any combination thereof. Subsets of immune cells, such as conventional T cells (Tcons), regulatory T cells (Tregs), invariant natural killer T cells (iNKTs), and memory T cells (Tmems) can contribute to aspects of GVHD following HCT, and can also contribute to, for example, GVT immune responses, immune reconstitution, infection susceptibility, and survival.

Disclosed herein are methods comprising administering populations of Tcons and Tregs to an HCT recipient subject. In some embodiments, iNKTs are also administered. In some embodiments, Tmems are also administered. The disclosure provides parameters for administering these populations of cells that contribute to successful clinical outcomes in HCT recipient subjects. Without wishing to be bound by theory, parameters that can contribute to successful clinical outcomes in HCT recipient subjects include, for example, populations administered, order and timing for the administration of different populations, purity standards for populations, methods for obtaining populations, methods of handling or storing populations (e.g., use of fresh versus frozen cell populations), dosages of populations administered, methods for obtaining populations, and combinations thereof.

GVHD is mediated in large part by donor T cells, which can elicit inflammatory responses upon recognition of recipient antigens. T cell depletion (TCD) of donor grafts can be undertaken to decrease the likelihood of acute and chronic GVHD. T cells can be depleted using methods including, but not limited to, physical adsorption of T cells to protein ligands such as lectins, immunodeletion with T cell specific antibodies, and immunoaffinity techniques (for example, use of T cell or lymphocyte-specific antibodies in immunoadsorption columns, magnetic activated cell sorting (MACS), or fluorescent activated cell sorting (FACS)). Applying TCD techniques to donor grafts can result in 10-fold to $10^5$-fold depletion of T cells, and reduced incidence of GVHD. However, TCD can also result in increased incidence of cancer relapse, as the lack of T cells can reduce graft-versus-tumor (GVT) immune responses. Additionally, TCD can result in impaired immune recovery, and increased susceptibility to infections.

Both GVT and GVHD are largely mediated by conventional T cells (Tcons), which mount immune responses upon recognition of cognate antigen by T cell receptors (tumor antigens for GVT, non-tumor recipient antigens for GVHD). Tcons can, for example, contribute to GVT, GVHD, or a combination thereof. Without wishing to be bound by theory, administration of Tcons after administration of Tregs can enhance GVT immunity, and/or reduce susceptibility to infection.

As used herein, Tcons can broadly refer to all CD3+ T cells, cells expressing medium to high levels of CD127, cells expressing CD3 and medium to high levels of CD127, or cells expressing CD3, medium to high levels of CD127, and CD4 or CD8. In some embodiments, Tcons do not express Vα24Jα18 TCR. Tcons and Tregs can be non-mutually-exclusive cell populations. In some embodiments, Tcons and Tregs are mutually exclusive cell populations.

Regulatory T cells ("Tregs") are a specialized subpopulation of T cells that can suppress activation of the immune system and thereby maintain immune tolerance. Without wishing to be bound by theory, populations of Tregs as administered by methods of the disclosure can contribute to positive clinical outcomes by, for example, reducing or preventing GVHD in a transplant recipient, and/or improving immune reconstitution in a transplant recipient. Administering Tregs with HSPCs prior to administering conventional T cells (Tcons) can, for example, facilitate retention of graft versus tumor (GVT) and prevention of GVHD. Administering Tregs with HSPCs prior to administering conventional T cells (Tcons) can, for example, facilitate retention of graft versus tumor (GVT) and reduces GVHD relative to alternate HCT methods. Administering Tregs with HSPCs prior to administering conventional T cells (Tcons) can, for example, facilitate retention of graft versus tumor (GVT) effects with reduced risk of GVHD relative to alternate HCT methods. Without wishing to be bound by theory, administering Tregs can prevent GVHD, and administering Tcons can promote GVT effects, for example, relative to alternate HCT methods. In some embodiments, administering Tregs reduces the risk of developing GVHD, and administering Tcons promotes GVT effects relative to alternate HCT methods.

There are various types of Tregs, for example, TCRαβ+ CD4+ regulatory T cells, which include natural regulatory T cells (nTregs) and induced regulatory T cells (iTregs). nTregs are T cells produced in the thymus and delivered to the periphery as a long-lived lineage of self-antigen-specific lymphocytes. iTregs are recruited from circulating lymphocytes and acquire regulatory properties under particular conditions of stimulation in the periphery. nTregs and iTregs are CD4+CD25+; both can inhibit proliferation of CD4+ CD25− T cells in a dose-dependent manner, and both are anergic and do not proliferate upon TCR stimulation. In addition to being positive for CD4 and CD25, Tregs are positive for the transcription factor FOXP3, an intracellular marker. Tregs can be identified or selected based on various marker expression profiles. Non-limiting examples of marker expression profiles that can be used to select Tregs include (1) CD4+CD25+CD127dim, (2) CD4+FOXP3+, (3) CD3+CD4+CD25+, (5) CD3-CD4+CD25+CD127dim, (6) CD3+CD4+CD25+CD127dim FOXP3+, (7) CD3+ FOXP3+, (8) CD3+CD4+FOXP3+, (9) CD3+CD4+CD25+ FOXP3+, (10) CD3-CD25+FOXP3+, (11) CD3+CD25-CD127dim, (12) CD4+CD25+, (13) CD4+CD25+ CD127dimFOXP3+, (14) FOXP3+, CD4+FOXP3+, (15) CD4+CD25+FOX3+, (16) CD25+FOXP3+, or (17) CD25+ CD127dim.

Selection based on certain expression profiles can be achieved based on extracellular markers and without requiring cell permeabilization, for example, selection based on CD4+CD25+CD127dim.

In the methods of the disclosure, administering Tregs to a subject receiving HCT can, for example, help to prevent graft rejection, help to prevent GVHD, help to reduce GVHD, promote hematopoietic reconstitution, promote immune reconstitution, promote mixed chimerism, or a combination thereof.

In the methods of the disclosure, Invariant natural killer T cells (iNKTs) can be administered to a subject. iNKTs are subclass of CD1d-restricted Natural Killer T (NKT) cells that express a highly conserved αβ-T cell receptor that comprises of Vα24Jα18 TCRα chain in humans (referred to herein as "Vα24Jα18+"). iNKT cells can be identified by binding with CD1d-multimers like that are loaded with α-galactosylceramide (GalCer), PBS-57, PBS-44 or other natural or synthetic glycolipids, and can be found as tetramers, dendrimers, and other structures, Fc fusions, or any combination thereof. Another method of identification is an antibody or combination of antibodies that specifically recognize the Vα24Jα18 region. Examples include a Vα24 antibody, a Jα18 antibody, or the monoclonal antibody clone 6B11 which binds specifically to a unique region of the Vα24Jα18 TCR and can be used to identify iNKT cells. iNKTs can be $CD3^+V\alpha24J\alpha18^+$.

In the methods of the disclosure, administering iNKTs to a subject receiving HCT can, for example, promote engraftment, promote GVT, reduce GVHD, decrease susceptibility to cancer relapse, decrease susceptibility to infection, or a combination thereof. In some embodiments, iNKTs promote the activity of Tregs. In some embodiments, iNKTs promote the activity of HSPCs.

In the methods of the disclosure, memory T cells (Tmems) can be administered to a subject. Tmems can refer to antigen experienced T cells that express, for example, the phenotypic markers CD45RO, TCRα, TCRβ, CD3, CD4 or CD8, CD95, and IL-2Rβ. Memory T cells provide immunity and are capable of persisting for a long period of time in an inactive state. Memory T cells are able to rapidly acquire effector functions upon re-challenge with antigen. A population of memory T cells can include the any combination of the subclasses T central memory cells and T effector memory cells. In some embodiments, Tmems are CD3+ CD45RA−CD45RO+. In the methods of the disclosure, Tmems administered to a subject receiving HCT can, for example, promote GVT, reduce GVHD, decrease susceptibility to cancer relapse, decrease susceptibility to infection, or a combination thereof.

HLA Types and Donor/Host Matching

The present disclosure provides methods comprising administering to a subject populations of cells. A population of cells to be administered to the recipient can be derived from an allogenic donor. A prospective and recipient can be ILA-typed in order to determine whether they are a match at any HLA alleles.

Human leukocyte antigens (HLA), also broadly referred to as Major histocompatibility complex (MHC) antigens, are protein molecules expressed on the surface of a cell that can confer an antigenic identity to that cell. HLA/MHC antigens are target molecules that can be recognized by T cells and natural killer (NK) cells as being derived from the same source of hematopoietic stem cells as the immune effector cells ("self"), or as being derived from another source of hematopoietic cells ("non-self"). HLA class I antigens (A, B, and C in humans) are expressed by the vast majority of cells, while HLA class II antigens (DR, DP, and DQ in humans) expressed primarily on professional antigen presenting cells. Both HLA classes are implicated in GVHD.

HLA antigens are encoded by highly polymorphic genes; a range of alleles exist for each HLA class I and II gene. Allelic gene products differ in one or more amino acids in the α and/or β domain(s). Panels of specific antibodies or nucleic acid reagents are used to type HLA haplotypes of individuals, using leukocytes that express class I and class II molecules. HLA alleles can be described at various levels of detail. Most designations begin with HLA- and the locus name, then * and some (even) number of digits specifying the allele. The first two digits specify a group of alleles. Older typing methodologies often could not completely distinguish alleles, and so stopped at this level. The third through fourth digits specify a synonymous allele. Digits five through six denote any synonymous mutations within the coding frame of the gene. The seventh and eighth digits distinguish mutations outside the coding region. Letters such as L, N, Q, or S may follow an allele's designation to specify an expression level or other non-genomic data known about it. Thus, a completely described allele may be up to 9 digits long, not including the HLA-prefix and locus notation.

Three HLA genes are considered most critical for HLA typing of potential transplant donors and recipients, HLA-A, HLA-B, and HLA-DR. As a human subject carries two copies of each, there are six total genes are 1-LA-typed.

HLA matched refers to a donor-recipient pair for which all six of the six HLA-A, HLA-B, and LLA-DR alleles are matched between donor and recipient. HLA mismatched refers to a donor-recipient pair for which at least one HLA antigen is mismatched between the donor and recipient. GVHD can occur even if the donor and recipient are HL A-matched because the immune system can still recognize other differences between their tissues.

The set of HLA alleles inherited from one parent forms a haplotype. Identifying a patient's haplotypes can help predict the probability of finding matching donors and assist in developing a search strategy, because some alleles and haplotypes are more common than others and they are distributed at different frequencies in different racial and ethnic groups. HLA haploidentical refers to a donor-recipient pair where one chromosome is matched at least at HLA-A; HLA-B, and HLA-DR between the donor and recipient. The haploidentical pair may or may not be matched at other alleles, e.g., other HLA genes on the other chromosome, or additional histocompatibility loci on either chromosome. Such donors frequently occur in families, e.g. a parent is haploidentical to a child; and siblings may be haploidentical.

The present disclosure provides methods comprising administering to a subject populations of cells. A population of cells to be administered to the recipient can be derived from an allogenic donor.

In some embodiments, populations of cells as disclosed herein are administered to a recipient subject after HLA typing a donor and a recipient, e.g., determining whether a donor and a recipient are HLA-matched or HLA-mismatched by typing HLA alleles HLA-A, HLA-B and HLA-DR in the donor and the recipient. A donor-recipient pair of the disclosure can be lLA matched, HLA mismatched, or haploidentical. The donor and recipient can be related (for example, a parent, child, sibling, grandparent, grandchild, aunt, uncle, or cousin). The donor and recipient can be related and HLA matched, HLA mismatched, or haploidentical. The donor and recipient can be unrelated.

Chimerism

Following administration of transplant cells from a donor to a recipient, chimerism can be monitored in the recipient. Chimerism can refer to the mix of donor and host cells in an individual who has received a HCT. The risk of GVHD is markedly reduced in patients with mixed instead of complete chimerism, and achieving mixed chimerism is desirable for this reason. In addition, immunodeficiency and infection are more frequently observed in complete versus mixed chimerism. In some embodiments, the methods provided herein allow a human subject to achieve mixed chimerism.

Subjects who exhibit more than a 95% donor cells in a given cell lineage at any time post-transplantation can be referred to as having full donor chimerism. Subjects who exhibit greater than 1% but less than 95% donor DNA in such analysis can be referred to as having mixed chimerism. Subjects who exhibit mixed chimerism can be further classified according to the evolution of chimerism, where improving mixed chimerism can comprise a continuous increase in the proportion of donor cells over at least a 6-month period. Stable mixed chimerism can comprise fluctuations in the percentage of recipient cells overtime, without complete loss of donor cells.

A determination of whether a subject is a full chimera, mixed chimera, or non-chimera can be made by an analysis of a hematopoietic cell sample from the graft recipient, e.g. peripheral blood or bone marrow. Analysis can be done by any convenient method of typing. In some embodiments, the degree of chimerism amongst all mononuclear cells, T cells, B cells, CD56+ NK cells, and CD15+ neutrophils is regularly monitored, using PCR with probes for microsatellite analysis. For example, commercial kits can be used to quantify donor and host genetic material extracted from cells based on polymorphisms in short terminal repeat lengths. Automated readers provide the percentage of donor type cells based on standard curves from artificial donor and host cell mixtures.

Methods

Acquisition of Cells

One or more cell populations of the disclosure can be obtained from a single donor, for example, obtained from mobilized peripheral blood apheresis of a single donor. HSPCs, Tregs, Tcons, iNTs, Tmems, or any combination thereof can be obtained from a single donor.

One or more cell populations of the disclosure can be obtained from one donor, and one or more additional cell populations of the disclosure can be obtained from a second donor. One cell population of the disclosure can be obtained from a single donor, and a second cell population of the disclosure can be obtained from multiple donors.

Populations of the disclosure can be obtained from multiple donors, for example, obtained from mobilized peripheral blood apheresis of multiple donors. HSPCs can be obtained from multiple donors. Tregs can be obtained from multiple donors. Tcons can be obtained from multiple donors. iNKTs can be obtained from multiple donors. Tmems can be obtained from multiple donors.

A donor and a recipient of the disclosure can be allogenic. A donor and a recipient of the disclosure can be HLA matched. A donor and a recipient of the disclosure can be HLA mismatched, e.g. mismatched at 1, 2, 3, 4, 5, or 6 of the major HLA alleles. A donor and a recipient of the disclosure can be haploidentical.

In some embodiments, a cell population of the disclosure can be obtained whole blood. A cell population of the disclosure can be obtained from a peripheral blood apheresis product, for example, a mobilized peripheral blood apheresis product. A cell population of the disclosure can be obtained from at least one apheresis product, two apheresis products, three apheresis products, four apheresis products, five apheresis products, six apheresis products, or more.

In some embodiments, a cell population of the disclosure can be obtained from bone marrow. In some embodiments, a cell population of the disclosure can be obtained from umbilical cord blood.

Processing of Cells

A population of cells of the disclosure can be refined by selection from another population of cells, for example, peripheral blood or a peripheral blood apheresis product. Selection methods for cell populations can comprise methods involving positive or negative selection of a cell population of interest. Selection methods for cell populations can comprise affinity reagents, including but not limited to an antibody, a full-length antibody, a fragment of an antibody, a naturally occurring antibody, a synthetic antibody, an engineered antibody, a full-length affibody, a fragment of an affibody, a full-length affilin, a fragment of an affilin, a full-length anticalin, a fragment of an anticalin, a full-length avimer, a fragment of an avimer, a fulllength DARPin, a fragment of a DARPin, a full-length fynomer, a fragment of a fynomer, a full-length kunitz domain peptide, a fragment of a kunitz domain peptide, a full-length monobody, a fragment of a monobody, a peptide, or a polyaminoacid. In some embodiments, the affinity reagent is directly conjugated to a detection reagent and/or purification reagent. In some cases, the detection reagent and purification reagent are the same. In other cases, the detection reagent and purification reagent are different. For example, the detection reagent and/or purification reagent is fluorescent, magnetic, or the like. In some cases, the detection reagent and/or purification reagent is a magnetic particle for column purification. For example, magnetic column purification may be performed using the Miltenyi system (CliniMACs) of columns, antibodies, buffers, preparation materials and reagents Affinity reagents can comprise immunoaffinity reagents, utilizing the binding specificity of antibodies or fragments or derivatives thereof to positively or negatively select for a cell population of interest. Selection methods for cell populations can comprise an affinity agent and a column, such as magnetic activated cell sorting (MACS) with specific antibodies and microbeads. Selection methods for cell populations can comprise fluorescent activated cell sorting (FACS), with cell populations sorted based on staining profiles with one or more fluorescently-conjugated antibodies. Selection methods for cell populations can comprise physical adsorption, for example, physical adsorption of T cells to protein ligands such as lectins.

A population of HSPCs of the disclosure can be selected based on expression of CD34. For example, a population of HSPCs of the disclosure can be selected using anti-CD34 antibodies as part of a magnetic activated cell sorting (MACS) or fluorescent activated cell sorting (FACS) system.

The number of HPSCs in a population of cells can be determined, for example, by quantifying CD34+ cells via flow cytometry. In some embodiments, dose calculations are adjusted based on measures of cell viability measurements, e.g., viability determined via flow cytometry with propidium iodide or 7-AAD, or via trypan blue exclusion, A population of cells comprising Tregs of the disclosure can be selected based on expression of markers including CD3, CD4, CD25, CD127, FOXP3, and combinations thereof.

A population of cells comprising Tregs can be selected using magnetic activated cell sorting (MACS). A population of cells comprising Tregs can be selected using fluorescent activated cell sorting (FACS). A population of cells comprising Tregs can be selected using multiple procedures, for example, multiple MACS selections, multiple FACS selections, or a combination of MACS and FACS selections. For example, a first selection may be performed for expression of CD25, isolating CD25+ cells from a hematopoietic cell sample, for example with MACS. A second selection may be performed by contacting the CD25+ cells with antibodies specific for CD4 and for CD127, where FACS is used to isolate cells that are CD4+CD127dim.

A population of cells comprising Tregs can be isolated from whole blood. A population of cells comprising Tregs can be isolated from a peripheral blood apheresis product. A population of cells comprising Tregs can be isolated from a population of cells previously enriched and/or depleted for one or more other cell types, e.g., isolated from a population of cells depleted of CD34+ cells. In some embodiments, Tregs are isolated from the flow-through fraction of a CD34+ MACS selection.

The number of Tregs in a population of cells can be determined, for example, by flow cytometry, where Tregs can be identified as, for example, CD4+CD25+CD127dim or CD4+FOXP3+. Dose calculations can be adjusted based on measures of cell viability measurements, e.g., viability determined via flow cytometry with propidium iodide or 7-AAD, or via trypan blue exclusion, A population of Tcons can be sourced from peripheral blood. A population of Tregs can be sourced from a peripheral blood apheresis product.

In some embodiments, no selection steps are carried out, and a population of Tcons is sourced directly from an aliquot of peripheral blood or apheresis product. In some embodiments, a population of cells can be enriched for Tcons, for example, by sorting based on the expression of various markers using MACS, FACS, or a combination thereof. A population of Tcons can be enriched by sorting for CD3+ cells. A population of Tcons can be enriched by sorting for CD4+ and CD8+ cells. A population of Tcons can be enriched by negative selection, where non-Tcon cells are removed, for example, by MACS depletion of cells expressing CD34, CD19, CD25, or a combination thereof.

The number of Tcons present in a population can be quantified, for example, by quantifying CD3+ cells via flow cytometry. The number of CD3+ cells in an aliquot can be determined and a volume comprising an appropriate dose of CD3 cells administered to the recipient. Dose calculations can be adjusted based on measures of cell viability, e.g., viability determined via flow cytometry with propidium iodide or 7-AAD, or via trypan blue exclusion.

An apheresis product of the disclosure can be split into two portions, one portion used to provide Tcons cells and the other portion to isolate and purify HSPCs and Tregs. In some embodiments, CD34+ cells are isolated and purified from the apheresis product, creating a CD34-negative cell fraction from which the Treg are then isolated.

A population of iNKTs can be sourced from peripheral blood. A population of iNKTs can be sourced from a peripheral blood apheresis product.

A population of cells can be enriched for iNKTs, for example, by sorting based on the expression of various markers using MACS, FACS, or a combination thereof. A population of iNKTs can be enriched, for example, by sorting for CD3⁺Vα24Jα18⁺ cells.

The number of iNKTs present in a population can be quantified, for example, by quantifying CD3⁺Vα24Jα18⁺ cells via flow cytometry. The number of CD3⁺Vα24Jα18⁺ cells in an aliquot can be determined and a volume comprising an appropriate dose of iNKTs administered to the recipient. In some embodiments, dose calculations are adjusted based on measures of cell viability measurements, e.g., viability determined via flow cytometry with propidium iodide or 7-AAD, or via trypan blue exclusion.

A population of Tmems can be sourced from peripheral blood. A population of Tmems can be sourced from a peripheral blood apheresis product.

A population of cells can be enriched for Tmems, for example, by sorting based on the expression of various markers using MACS, FACS, or a combination thereof. A population of Tmems can be enriched, for example, by sorting for CD3+CD45RA−CD45RO+ cells.

The number of Tmems present in a population can be quantified, for example, by quantifying CD3+CD45RA−CD45RO+ cells via flow cytometry. The number of CD3+CD45RA−CD45RO+ cells in an aliquot can be determined and a volume comprising an appropriate dose of Tmems administered to the recipient. Dose calculations can be adjusted based on measures of cell viability measurements, e.g., viability determined via flow cytometry with propidium iodide or 7-AAD, or via trypan blue exclusion.

Use of Fresh or Cryopreserved Cells

A cell population of the disclosure can be administered freshly after isolation, or after cryopreservation and subsequent thawing.

Cells freshly isolated from a donor ("fresh cells" can be administered to a recipient subject. Fresh cells can be stored in a buffer, for example, CliniMACS PBS-EDTA Buffer with 0.5% human serum albumin, or Plasma-Lyte-A, pH 7.4 supplemented with 2% human serum albumin. Fresh cells can be stored at a reduced temperature (e.g., 2-8° C.), but cannot be cryopreserved/frozen.

After acquiring a fresh population of cells from a donor, the fresh cells can be stored for greater than at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 120, 150, 200, 300 hours, or more prior to administration to a subject.

After acquiring a fresh population of cells from a donor, the fresh cells can be stored for at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 120, 150, 200, 300 hours, or less prior to administration to a subject.

Cells of the disclosure can be cryopreserved. In some embodiments, cryopreservation can be beneficial to the methods disclosed herein. For example, cryopreservation of Tcons prior to subsequent thawing and administering to a subject may reduce GVHD.

Cryopreservation can comprise addition of a preservative agent (e.g., DMSO), and gradual cooling of cells in a controlled-rate freezer to prevent osmotic cellular injury during ice crystal formation. Cryopreservation can comprise commercial cryopreservation reagents and materials, for example, Cryobags and CryoStor® CS10.

Cryopreserved cells can be stored for periods of time ranging from hours to years at low temperatures. Cryopreserved cells can be stored at ultralow temperatures, for example, −50° C., −60° C., −70° C., −80° C., −90° C., −100° C., −110° C., −120° C., −130° C., −140° C., −150° C., −160° C., −170° C., −180° C., −190° C., −196° C., or less. Cryopreserved cells can be stored in storage devices comprising liquid nitrogen.

Cells can be cryopreserved before or after other methods of the disclosure, for example, before or after sorting methods, before or after characterization methods, such as determining cell viability or the concentration of cells of a particular type.

In some embodiments, whole blood can be cryopreserved. Whole blood can be cryopreserved without sorting or characterization. Whole blood can be cryopreserved after sorting but without characterization. Whole blood can be cryopreserved after characterization but without sorting. Whole blood can be cryopreserved after characterization and sorting. Whole blood can be cryopreserved after quantifying a cell type of the disclosure Whole blood can be cryopreserved after quantifying conventional T cells (Tcons, e.g., CD3+ cells). Whole blood can be cryopreserved after quantifying viability of all cells or a population of cells of the disclosure (e.g., conventional T cells).

A peripheral blood apheresis product of the disclosure can be cryopreserved. A peripheral blood apheresis product can be cryopreserved without sorting or characterization. A peripheral blood apheresis product can be cryopreserved after sorting but without characterization. A peripheral blood apheresis product can be cryopreserved after characterization but without sorting. A peripheral blood apheresis product can be cryopreserved after characterization and sorting. A peripheral blood apheresis product can be cryopreserved after quantifying a cell type of the disclosure. A peripheral blood apheresis product can be cryopreserved after quantifying conventional T cells (Tcons, e.g., CD3+ cells). A peripheral blood apheresis product can be cryopreserved after quantifying viability of all cells or a population of cells of the disclosure (e.g., conventional T cells).

A population of cells sorted or selected from another population of cells can be cryopreserved, for example, a population of HSPCs, Tregs, Tcons, iNKTs, or Tmems can be cryopreserved.

Cells of the disclosure can be cryopreserved for any amount of time. Cells of the disclosure may be cryopreserved for greater than at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours, or more prior to thawing and administration to a subject.

Cells of the disclosure can be cryopreserved for at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours, or less prior to thawing and administration to a subject.

Cells of the disclosure can be cryopreserved for greater than at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 days, or more prior to thawing and administration to a subject.

Cells of the disclosure can be cryopreserved for at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 days, or less prior to thawing and administration to a subject.

Administration of Cells

Sequence and Timing of Administration

Disclosed herein are methods for enhanced allogenic hematopoietic stem cell transplantation, comprising administering to a subject populations of cells.

In some embodiments, a population of hematopoietic stem and progenitor cells (HSPCs), a population of cells comprising regulatory T cells (Tregs) and a population of conventional T cells (Tcons) are administered to a subject.

The population of HSPCs and the population of cells comprising Tregs can be administered at the same or similar times, or at different times.

The population of HSPCs and the population of cells comprising Tregs can administered at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 hours apart.

The population of Tcons can be administered to the subject after the population of HSPCs.

The population of Tcons can be administered to the subject greater than at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours after the population of HSPCs.

In some embodiments, the population of Tcons is administered to the subject at most about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours after the population of HSPCs.

The population of Tcons can be administered to the subject, for example, between about 6-96, 12-84, 12-72, 12-66, 12-60, 12-54, 12-48, 12-42, 12-36, 12-30, 12-24, 12-18, 18-72, 18-66, 18-60, 18-54, 18-48, 18-42, 18-36, 18-30, 18-24, 24-72, 24-66, 24-60, 24-54, 24-48, 24-42, 24-36, 24-30, 30-72, 30-66, 30-60, 30-54, 30-48, 30-42, 30-36, 36-72, 36-66, 36-60, 36-54, 36-48, 36-42, 42-72, 42-66, 42-60, 42-54, 42-48, 48-72, 48-66, 48-60, 48-54, 54-72, 54-66, 54-60, 60-72, 60-66, or 66-72 hours after the population of HSPCs.

The population of Tcons can be administered to the subject after the population of cells comprising Tregs.

The population Tcons can be administered to the subject greater than at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours after the population of cells comprising Tregs.

In some embodiments, the population of Tcons is administered to the subject at most about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours after the population of cells comprising Tregs.

The population of Tcons can be administered to the subject, for example, between about 6-96, 12-84, 12-72, 12-66, 12-60, 12-54, 12-48, 12-42, 12-36, 12-30, 12-24, 12-18, 18-72, 18-66, 18-60, 18-54, 18-48, 18-42, 18-36, 18-30, 18-24, 24-72, 24-66, 24-60, 24-54, 24-48, 24-42, 24-36, 24-30, 30-72, 30-66, 30-60, 30-54, 30-48, 30-42, 30-36, 36-72, 36-66, 36-60, 36-54, 36-48, 36-42, 42-72, 42-66, 42-60, 42-54, 42-48, 48-72, 48-66, 48-60, 48-54, 54-72, 54-66, 54-60, 60-72, 60-66, or 66-72 hours after the population of Tregs.

The population of Tcons can be administered to the subject after the population of HSPCs and the population of cells comprising Tregs.

The population Tcons can administered to the subject, for example, greater than at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours after the population of HSPCs and the population of cells comprising Tregs.

In some embodiments, the population of Tcons is administered to the subject at most about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours after the population of iSPCs and the population of cells comprising Tregs.

The population of Tcons can be administered to the subject, for example, between about 6-96, 12-84, 12-72, 12-66, 12-60, 12-54, 12-48, 12-42, 12-36, 12-30, 12-24, 12-18, 18-72, 18-66, 18-60, 18-54, 18-48, 18-42, 18-36, 18-30, 18-24, 24-72, 24-66, 24-60, 24-54, 24-48, 24-42, 24-36, 24-30, 30-72, 30-66, 30-60, 30-54, 30-48, 30-42, 30-36, 36-72, 36-66, 36-60, 36-54, 36-48, 36-42, 42-72, 42-66, 42-60, 42-54, 42-48, 48-72, 48-66, 48-60, 48-54, 54-72, 54-66, 54-60, 60-72, 60-66, or 66-72 hours after the population of HSPCs and the population of cells comprising Tregs.

In some embodiments, a population of hematopoietic stem and progenitor cells (HSPCs), a population of cells comprising regulatory T cells (Tregs), a population of conventional T cells (Tcons), and a population of invariant natural killer T cells (iNKTs) are administered to a subject.

The population of iNKTs can be administered to the subject at the same time or at a similar time as the population of HSPCs. In some embodiments, the population of iNKTs is administered to the subject after the population of HSPCs.

The population of iNKTs can be administered to the subject greater than at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours after the population of HSPCs.

In some embodiments, the population of iNKTs is administered to the subject at most about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours after the population of HSPCs.

The population ofiNKTs can be administered to the subject, for example, between about 6-96, 12-84, 12-72, 12-66, 12-60, 12-54, 12-48, 12-42, 12-36, 12-30, 12-24, 12-18, 18-72, 18-66, 18-60, 18-54, 18-48, 18-42, 18-36, 18-30, 18-24, 24-72, 24-66, 24-60, 24-54, 24-48, 24-42, 24-36, 24-30, 30-72, 30-66, 30-60, 30-54, 30-48, 30-42, 30-36, 36-72, 36-66, 36-60, 36-54, 36-48, 36-42, 42-72, 42-66, 42-60, 42-54, 42-48, 48-72, 48-66, 48-60, 48-54, 54-72, 54-66, 54-60, 60-72, 60-66, or 66-72 hours after the population of HSPCs.

The population of iNKTs can be administered to the subject at the same time or at a similar time as the population of cells comprising Tregs. In some embodiments, the population of iNKTs is administered to the subject after the population of cells comprising Tregs.

A population of iNKTs can be administered to the subject greater than at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours after the population of cells comprising Tregs.

In some embodiments, the population of iNKTs is administered to the subject at most about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours after the population of cells comprising Tregs.

The population of iNKTs can be administered to the subject, for example, between about 6-96, 12-84, 12-72, 12-66, 12-60, 12-54, 12-48, 12-42, 12-36, 12-30, 12-24, 12-18, 18-72, 18-66, 18-60, 18-54, 18-48, 18-42, 18-36, 18-30, 18-24, 24-72, 24-66, 24-60, 24-54, 24-48, 24-42, 24-36, 24-30, 30-72, 30-66, 30-60, 30-54, 30-48, 30-42, 30-36, 36-72, 36-66, 36-60, 36-54, 36-48, 36-42, 42-72, 42-66, 42-60, 42-54, 42-48, 48-72, 48-66, 48-60, 48-54, 54-72, 54-66, 54-60, 60-72, 60-66, or 66-72 hours after the population of Tregs.

In some embodiments, a population of hematopoietic stem and progenitor cells (HSPCs), a population of cells comprising regulatory T cells (Tregs), a population of conventional T cells (Tcons), and a population of memory T cells (Tmems) are administered to a subject.

A population of Tmems can be administered to the subject at the same time or at a similar time as the population of HSPCs. in some embodiments, the population of Tmems is administered to the subject after the population of HSPCs.

The population of Tmems can be administered to the subject greater than at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours after the population of HSPCs.

In some embodiments, the population of Tmems is administered to the subject at most about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours after the population of HSPCs.

The population of Tmems can be administered to the subject, for example, between about 6-96, 12-84, 12-72, 12-66, 12-60, 12-54, 12-48, 12-42, 12-36, 12-30, 12-24, 12-18, 18-72, 18-66, 18-60, 18-54, 18-48, 18-42, 18-36, 18-30, 18-24, 24-72, 24-66, 24-60, 24-54, 24-48, 24-42, 24-36, 24-30, 30-72, 30-66, 30-60, 30-54, 30-48, 30-42, 30-36, 36-72, 36-66, 36-60, 36-54, 36-48, 36-42, 42-72, 42-66, 42-60, 42-54, 42-48, 48-72, 48-66, 48-60, 48-54, 54-72, 54-66, 54-60, 60-72, 60-66, or 66-72 hours after the population of HSPCs.

The population of Tmems can be administered to the subject at the same time or at a similar time as the population of cells comprising Tregs. In some embodiments, the population of Tmems is administered to the subject after the population of cells comprising Tregs.

The population of Tmems can be administered to the subject greater than at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours after the population of cells comprising Tregs.

In some embodiments, the population of Tmems is administered to the subject at most about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours after the population of cells comprising Tregs.

The population of Tmems can be administered to the subject, for example, between about 6-96, 12-84, 12-72, 12-66, 12-60, 12-54, 12-48, 12-42, 12-36, 12-30, 12-24, 12-18, 18-72, 18-66, 18-60, 18-54, 18-48, 18-42, 18-36, 18-30, 18-24, 24-72, 24-66, 24-60, 24-54, 24-48, 24-42, 24-36, 24-30, 30-72, 30-66, 30-60, 30-54, 30-48, 30-42, 30-36, 36-72, 36-66, 36-60, 36-54, 36-48, 36-42, 42-72, 42-66, 42-60, 42-54, 42-48, 48-72, 48-66, 48-60, 48-54, 54-72, 54-66, 54-60, 60-72, 60-66, or 66-72 hours after the population of Tregs.

Doses

HSPCs

A population of HPSCs administered to a subject can be administered at a dose greater than at least about $1 \times 10^4$, $1 \times 10^5$, $5 \times 10^5$, $6 \times 10^5$, $7 \times 10^5$, $8 \times 10^5$, $9 \times 10^5$, $1 \times 10^6$, $1.1 \times 10^6$, $1.2 \times 10^6$, $1.3 \times 10^6$, $1.4 \times 10^6$, $1.5 \times 10^6$, $1.6 \times 10^6$, $1.7 \times 10^6$, $1.8 \times 10^6$, $1.9 \times 10^6$, $2 \times 10^6$, $2.1 \times 10^6$, $2.2 \times 10^6$, $2.3 \times 10^6$, $2.4 \times 10^6$, $2.5 \times 10^6$, $2.6 \times 10^6$ $2.7 \times 10^6$, $2.8 \times 10^6$, $2.9 \times 10^6$, $3 \times 10^6$, $3.1 \times 10^6$, $3.2 \times 10^6$, $3.3 \times 10^6$, $3.4 \times 10^6$, $3.5 \times 10^6$, $3.6 \times 10^6$, $3.7 \times 10^6$, $3.8 \times 10^6$, $3.9 \times 10^6$, $4 \times 10^6$, $4.1 \times 10^6$, $4.2 \times 10^6$, $4.3 \times 10^6$, $4.4 \times 10^6$, $4.5 \times 10^6$, $4.6 \times 10^6$, $4.7 \times 10^6$, $4.8 \times 10^6$, $4.9 \times 10^6$, $5 \times 10^6$, $5.1 \times 10^6$, $5.2 \times 10^6$, $5.3 \times 10^6$, $5.4 \times 10^6$, $5.5 \times 10^6$, $5.6 \times 10^6$, $5.7 \times$ $10^6$, $5.8\times10^6$, $5.9\times10^6$, $6\times10^6$, $6.5\times10^6$, $7\times10^6$, $7.5\times10^6$, $8\times10^6$, $8.5\times10^6$, $9\times10^6$, $9.5\times10^6$, $1\times10^7$, $1.5\times10^7$, $2\times10^7$, $2.5\times10^7$, $3\times10^7$, $3.5\times10^7$, $4\times10^7$, $4.5\times10^7$, $5\times10^7$, $5.5\times10^7$, $6\times10^7$, $6.5\times10^7$, $7\times10^7$, $7.5\times10^7$, $8\times10^7$, $8.5\times10^7$, $9\times10^7$, $9.5\times10^7$, $1\times10^8$, $1\times10^8$, $1.5\times10^8$, $2\times10^8$, $2.5\times10^8$, $3\times10^8$, $3.5\times10^8$, $4\times10^7$, $4.5\times10^8$, $5\times10^8$, $5.5\times10^8$, $6\times10^8$, $6.5\times10^8$, $7\times10^8$, $7.5\times10^8$, $8\times10^8$, $8.5\times10^8$, $9\times10^8$, $9.5\times10^8$, $1\times10^9$, or more cells per kg of recipient body weight.

In some embodiments, a population of HPSCs administered to a subject can be administered at a dose of at most about $1\times10^4$, $1\times10^5$, $5\times10^5$, $6\times10^5$, $7\times10^5$, $8\times10^5$, $9\times10^5$, $1\times10^6$, $1.1\times10^6$, $1.2\times10^6$, $1\times10^6$, $1\times10^6$, $1.5\times10^6$, $1.6\times10^6$, $1.7\times10^6$, $1.8\times10^6$, $1.9\times10^6$, $2\times10^6$, $2.1\times10^6$, $2.2\times10^6$ $2.3\times10^6$, $2.4\times10^6$, $2.5\times10^6$ $2.6\times10^6$, $2.7\times10^6$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$, $4.5\times10^6$, $4.6\times10^6$, $4.7\times10^6$, $4.8\times10^6$, $4.9\times10^6$, $5\times10^6$, $5.1\times10^6$, $5.2\times10^6$, $5.3\times10^6$, $5.4\times10^6$, $5.5\times10^6$, $5.6\times10^6$, $5.7\times10^6$, $5.8\times10^6$, $5.9\times10^6$, $6\times10^6$, $6.5\times10^6$, $7\times10^6$, $7.5\times10^6$, $8\times10^6$, $8.5\times10^6$, $9\times10^6$, $9.5\times10^6$, $1\times10^7$, $1.5\times10^7$, $2\times10^7$, $2.5\times10^7$, $3\times10^7$, $3.5\times10^7$, $4\times10^7$, $4.5\times10^7$, $5\times10^7$, $5.5\times10^7$, $6\times10^7$, $6.5\times10^7$, $7\times10^7$, $7.5\times10^7$, $8\times10^7$, $8.5\times10^7$, $9\times10^7$, $9.5\times10^7$, $1\times10^8$, $1\times10^8$, $1.5\times10^8$, $2\times10^8$, $2.5\times10^7$, $3\times10^8$, $3.5\times10^8$, $4\times10^7$, $4.5\times10^8$, $5\times10^8$, $5.5\times10^8$, $6\times10^8$, $6.5\times10^8$, $7\times10^8$, $7.5\times10^8$, $8\times10^8$, $8.5\times10^8$, $9\times10^8$, $9.5\times10^8$, $1\times10^9$, or less cells per kg of recipient body weight.

A population of HPSCs administered to a subject can be administered at a dose, for example, greater than at least about $1\times10^4$, $1\times10^5$, $5\times10^5$, $6\times10^5$, $7\times10^5$, $8\times10^5$, $9\times10^5$, $1\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$, $3\times10^6$ $1\times10^6$, $3.2\times10^6$, $3.3\times10^6$, $3.4\times10^6$, $3.5\times10^6$, $3.6\times10^6$ $3.7\times10^6$, $3.8\times10^6$, $3.9\times10^6$, $4\times10^6$, $4.1\times10^6$ $4.2\times10^6$, $4.3\times10^6$, $4.4\times10^6$, $4.5\times10^6$, $4.6\times10^6$, $4.7\times10^6$, $4.8\times10^6$, $4.9\times10^6$, $5\times10^6$, $5.1\times10^6$, $5.2\times10^6$, $5.3\times10^6$, $5.4\times10^6$, $5.5\times10^6$, $5.6\times10^6$, $5.7\times10^6$, $5.8\times10^6$, $5.9\times10^6$, $6\times10^6$, $6.5\times10^6$, $7\times10^6$, $7.5\times10^6$, $8\times10^6$, $8.5\times10^6$, $9\times10^6$, $9.5\times10^6$, $1\times10^7$ $1.5\times10^7$, $2\times10^7$, $2.5\times10^7$, $3\times10^7$, $3.5\times10^7$, $4\times10^7$, $4.5\times10^7$, $5\times10^7$, $5.5\times10^7$, $6\times10^7$, $6.5\times10^7$, $7\times10^7$, $7.5\times10^7$, $8\times10^7$, $8.5\times10^7$, $9\times10^7$, $9.5\times10^7$, $1\times10^8$, $1\times10^8$, $1.5\times10^8$, $2\times10^8$, $2.5\times10^8$, $3\times10^8$, $3.5\times10^8$, $4\times10^7$, $4.5\times10^8$, $5\times10^8$, $5.5\times10^8$, $6\times10^8$, $6.5\times10^8$, $7\times10^8$, $7.5\times10^8$, $8\times10^8$, $8.5\times10^8$, $9\times10^8$, $9.5\times10^8$, $1\times10^9$, or more CD34+ cells per kg of recipient body weight.

A population of HPSCs administered to a subject can be administered at a dose of at most about $1\times10^4$, $1\times10^5$, $5\times10^5$, $6\times10^5$, $7\times10^5$, $8\times10^5$ $9\times10^5$, $1\times10^6$, $1.1\times10^6$, $1.2\times10^6$ $0.3\times10^6$, $1.4\times10^6$, $1.5\times10^6$, $1.6\times10^6$, $1.7\times10^6$, $1.8\times10^6$, $1.9\times10^6$, $2\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$, $4.5\times10^6$, $4.6\times10^6$, $4.7\times10^6$, $4.8\times10^6$, $4.9\times10^6$, $5\times10^6$, $5.1\times10^6$, $5.2\times10^6$, $5.3\times10^6$, $5.4\times10^6$, $5.5\times10^6$, $5.6\times10^6$, $5.7\times10^6$, $5.8\times10^6$, $5.9\times10^6$, $6\times10^6$, $6.5\times10^6$, $7\times10^6$, $7.5\times10^6$, $8\times10^6$, $8.5\times10^6$, $9\times10^6$, $9.5\times10^6$, $1\times10^7$, $1.5\times10^7$, $2\times10^7$, $2.5\times10^7$, $3\times10^7$, $3.5\times10^7$, $4\times10^7$, $4.5\times10^7$, $5\times10^7$, $5.5\times10^7$, $6\times10^7$, $6.5\times10^7$, $7\times10^7$, $7.5\times10^7$, $8\times10^7$, $8.5\times10^7$, $9\times10^7$, $9.5\times10^7$, $1\times10^8$, $1\times10^8$, $1.5\times10^8$, $2\times10^7$, $2.5\times10^8$, $3\times10^8$, $3.5\times10^8$, $4\times10^7$, $4.5\times10^8$, $5\times10^8$, $5.5\times10^8$, $6\times10^8$, $6.5\times10^8$, $7\times10^8$, $7.5\times10^8$, $8\times10^8$, $8.5\times10^8$, $9\times10^8$, $9.5\times10^8$, $1\times10^9$, or less CD34+ cells per kg of recipient body weight.

For example, a population of HPSCs administered to a subject can be administered at a dose of $1\times10^4$ to $1\times10^9$, $1\times10^5$ to $1\times10^8$, $1\times10^5$ to $2\times10^7$, $5\times10^5$ to $2\times10^7$, $5\times10^5$ to $1.5\times10^7$, $5\times10^5$ to $1\times10^7$, $5\times10^5$ to $9\times10^6$, $5\times10^5$ to $8\times10^6$, $5\times10^5$ to $7\times10^6$, $5\times10^5$ to $6\times10^6$, $5\times10^5$ to $5\times10^6$, $5\times10^5$ to $4\times10^6$, $5\times10^5$ to $3\times10^6$, $5\times10^5$ to $2\times10^6$, $5\times10^5$ to $1\times10^6$, $1\times10^6$ to $1.5\times10^7$, $1\times10^6$ to $1\times10^7$, $1\times10^6$ to $9\times10^6$, $1\times10^6$ to $8\times10^6$, $1\times10^6$ to $7\times10^6$, $1\times10^6$ to $6\times10^6$, $1\times10^6$ to $5\times10^6$, $1\times10^6$ to $4\times10^6$, $1\times10^6$ to $3\times10^6$, $1\times10^6$ to $2\times10^6$, $1.5\times10^6$ to $1.5\times10^7$, $1.5\times10^6$ to $1\times10^7$, $1.5\times10^6$ to $9\times10^6$, $1.5\times10^6$ to $8\times10^6$, $1.5\times10^6$ to $7\times10^6$, $1.5\times10^6$ to $6\times10^6$, $1.5\times10^6$ to $5\times10^6$, $1.5\times10^6$ to $4\times10^6$, $1.5\times10^6$ to $3\times10^6$, $1.5\times10^6$ to $2\times10^6$, $2\times10^6$ to $1.5\times10^7$, $2\times10^6$ to $1\times10^7$, $2\times10^6$ to $9\times10^6$, $2\times10^6$ to $8\times10^6$, $2\times10^6$ to $7\times10^6$, $2\times10^6$ to $6\times10^6$, $2\times10^6$ to $5\times10^6$, $2\times10^6$ to $4\times10^6$, $2\times10^6$ to $3\times10^6$, $2.5\times10^6$ to $1.5\times10^7$, $2.5\times10^6$ to $1\times10^7$, $2.5\times10^6$ to $9\times10^6$, $2.5\times10^6$ to $8\times10^6$, $2.5\times10^6$ to $7\times10^6$, $2.5\times10^6$ to $6\times10^6$, $2.5\times10^6$ to $5\times10^6$, $2.5\times10^6$ to $4\times10^6$, or $2.5\times10^6$ to $3\times10^6$ cells per kg of recipient body weight.

A population of HPSCs administered to a subject can be administered, for example, at a dose of $1\times10^4$ to $1\times10^9$, $1\times10^5$ to $1\times10^8$, $1\times10^5$ to $2\times10^7$, $5\times10^5$ to $2\times10^7$, $5\times10^5$ to $1.5\times10^7$, $5\times10^5$ to $1\times10^7$, $5\times10^7$ to $9\times10^6$, $5\times10^5$ to $8\times10^6$, $5\times10^7$ to $7\times10^6$, $5\times10^5$ to $6\times10^6$, $5\times10^5$ to $5\times10^6$, $5\times10^5$ to $4\times10^6$, $5\times10^5$ to $3\times10^6$, $5\times10^5$ to $2\times10^6$, $5\times10^5$ to $1\times10^6$, $1\times10^6$ to $1.5\times10^7$, $1\times10^6$ to $1\times10^7$, $1\times10^6$ to $9\times10^6$, $1\times10^6$ to $8\times10^6$, $1\times10^6$ to $7\times10^6$, $1\times10^6$ to $6\times10^6$, $1\times10^6$ to $5\times10^6$, $1\times10^6$ to $4\times10^6$, $1\times10^6$ to $3\times10^6$, $1\times10^6$ to $2\times10^6$, $1.5\times10^6$ to $1.5\times10^7$, $1.5\times10^6$ to $1\times10^7$, $1.5\times10^6$ to $9\times10^6$, $1.5\times10^6$ to $8\times10^6$, $1.5\times10^6$ to $7\times10^6$, $1.5\times10^6$ to $6\times10^6$, $1.5\times10^6$ to $5\times10^6$, $1.5\times10^6$ to $4\times10^6$, $1.5\times10^6$ to $3\times10^6$, $1.5\times10^6$ to $2\times10^6$, $2\times10^6$ to $1.5\times10^7$, $2\times10^6$ to $1\times10^7$, $2\times10^6$ to $9\times10^6$, $2\times10^6$ to $8\times10^6$, $2\times10^6$ to $7\times10^6$, $2\times10^6$ to $6\times10^6$, $2\times10^6$ to $5\times10^6$, $2\times10^6$ to $4\times10^6$, $2\times10^6$ to $3\times10^6$, $2.5\times10^6$ to $1.5\times10^7$, $2.5\times10^6$ to $1\times10^7$, $2.5\times10^6$ to $9\times10^6$, $2.5\times10^6$ to $8\times10^6$, $2.5\times10^6$ to $7\times10^6$, $2.5\times10^6$ to $6\times10^6$, $2.5\times10^6$ to $5\times10^6$, $2.5\times10^6$ to $4\times10^6$, or $2.5\times10^6$ to $3\times10^6$ CD34+ cells per kg of recipient body weight.

A population of HSPCs of the disclosure can have a defined level of purity for CD34+ cells.

For example, a population of HSPCs of the disclosure can comprise greater than at least about 5%, 10%, 15%, 20%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74% 75%, 76%, 77%, 78%, 79%, 80%, 81%, 82%, 83%, 84%, 85%, 86%, 87, 88%, 89%, 90%, 91%, 92%, 93%, 94%, 95%, 96%, 97%, 98%, 99%, or more CD34+ cells as a percentage of total cells, nucleated cells, or CD45+ cells.

In some embodiments, a population of HSPCs of the disclosure comprises at most about 5%, 10%, 15%, 20%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or less CD34+ cells as a percentage of total cells, nucleated cells, or CD45+ cells.

A population of HSPCs of the disclosure can have a defined level of contaminating CD3+ cells.

For example, greater than at least about $1\times10^2$, $2\times10^2$, $3\times10^2$, $4\times10^2$, $5\times10^2$, $6\times10^2$, $7\times10^2$, $8\times10^2$, $9\times10^2$, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, or more CD3+ cells per kg of recipient body weight are present in a population of HSPCs of the disclosure.

In some embodiments, at most about $1\times10$, $2\times10^2$, $3\times10^2$, $4\times10^2$, $5\times10^2$, $6\times10^2$, $7\times10^2$, $8\times10^2$, $9\times10^2$, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, or less CD3+ cells per kg of recipient body weight are present in a population of HSPCs of the disclosure.

A population of HSPCs of the disclosure can comprise greater than at least about 0.001%, 0.002%, 0.003%, 0.004%, 0.005%, 0.006%, 0.007%, 0.008% 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 5%, 6%, 7%, 8%, 9%, 10%, or more CD3+ cells as a percentage of total cells, nucleated cells, or CD45+ cells.

In some embodiments, a population of HSPCs of the disclosure comprises at most about 0.001%, 0.002%, 0.003%, 0.004%, 0.005%, 0.006%, 0.007%, 0.008% 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9% 3%, 3.1%, 3.2%, 3.3% 3.4%, 3.5%, 3.6%, 3.7%, 3.8%, 3.9%, 4%, 5%, 6%, 7%, 8%, 9%, 10%, or less CD3+ cells as a percentage of total cells, nucleated cells, or CD45+ cells.

Tregs

A population of cells comprising Tregs administered to a subject can be administered at a dose greater than at least about $1\times10^4$, $1\times10^5$, $2\times10^5$, $3\times10^5$, $4\times10^5$, $5\times10^5$, $6\times10^5$, $7\times10^5$ $8\times10^5$, $9\times10^5$, $1\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$, $4.5\times10^6$, $4.6\times10^6$, $4.7\times10^6$, $4.8\times10^6$, $4.9\times10^6$, $5\times10^6$, $5.1\times10^6$, $52\times10^6$, $5.3\times10^6$, $5.4\times10^6$, $5.5\times10^6$, $5.6\times10^6$, $5.7\times10^6$, $5.8\times10^6$, $5.9\times10^6$, $6\times10^6$, $6.5\times10^6$, $7\times10^6$, $7.5\times10^6$, $8\times10^6$, $8.5\times10^6$, $9\times10^6$, $9.5\times10^6$, $1\times10^7$, $1.5\times10^7$, $2\times10^7$, $2.5\times10^7$, $3\times10^7$, $3.5\times10^7$, $4\times10^7$, $4.5\times10^7$, $5\times10^7$, $5.5\times10^7$, $6\times10^7$, $6.5\times10^7$, $7\times10^7$, $7.5\times10^7$, $8\times10^7$, $8.5\times10^7$, $9\times10^7$, $9.5\times10^7$, $1\times10^8$, $1\times10^8$, $1.5\times10^8$, $2\times10^8$, $2.5\times10^8$, $3\times10^8$, $3.5\times10^8$, $4\times10^7$, $4.5\times10^8$, $5\times10^8$, $5.5\times10^8$, $6\times10^8$, $6.5\times10^8$, $7\times10^8$, $7.5\times10^8$, $8\times10^8$, $8.5\times10^8$, $9\times10^8$, $9.5\times10^8$, $1\times10^9$, or more cells per kg of recipient body weight.

In some embodiments, a population of cells comprising Tregs administered to a subject can be administered at a dose of at most about $1\times10^4$, $1\times10^5$, $2\times10^5$, $3\times10^5$, $4\times10^5$, $6\times10^5$, $7\times10^5$, $8\times10^5$, $9\times10^5$, $1\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$, $4.5\times10^6$, $4.6\times10^6$, $4.7\times10^6$, $4.8\times10^6$, $4.9\times10^6$, $5\times10^6$, $5.1\times10^6$, $5.2\times10^6$, $53\times10^6$, $5.4\times10^6$, $5.5\times10^6$, $5.6\times10^6$, $5.7\times10^6$, $5.8\times10^6$, $5.9\times10^6$, $6\times10^6$, $6.5\times10^6$, $7\times10^6$, $7.5\times10^6$, $8\times10^6$, $8.5\times10^6$, $9\times10^6$, $9.5\times10^6$, $1\times10^7$, $1.5\times10^7$, $2\times10^7$, $2.5\times10^7$, $3\times10^7$, $3.5\times10^7$, $4\times10^7$, $4.5\times10^7$, $5\times10^7$, $5.5\times10^7$, $6\times10^7$, $6.5\times10^7 7\times10^7$, $8\times10^7$, $8.5\times10^7$, $9\times10^7$, $9.5\times10^7$, $1\times10^8$, $1\times10^8$, $1.5\times10^8$, $2\times10^8$, $2.5\times10^8$, $3\times10^8$, $3.5\times10^8$, $4\times10^7$, $4.5\times10^8$, $5\times10^8$, $5.5\times10^8$, $6\times10^8$, $6.5\times10$, $7\times10^8$, $7.5\times10$, $8\times10^8$, $8.5\times10^8$, $9\times10^8$, $9.5\times10^8$, $1\times10^9$ or less cells per kg of recipient body weight.

A population of cells comprising Tregs administered to a subject can be administered, for example at a dose greater than at least about $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $1.1\times10^6$, $1.2\times10^6$, $1.3\times 10^6$, $1.4\times10^6$, $1.5\times10^6$, $1.6\times10^6$, $1.7\times10^6$, $1.8\times10^6$, $1.9\times10^6$, $2\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$ $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times 10^6$, $4\times10^6$, $4.1\times10^6$, $4.2\times10^6$, $4.3\times10^6$, $4.4\times10^6$, $4.5\times10^6$, $4.6\times10^6$, $4.7\times10^6$, $4.8\times10^6$, $4.9\times10^6$, $5\times10^6$, $5.1\times10^6$, $5.2\times 10^6$, $5.3\times10^6$, $5.4\times10^6$, $5.5\times10^6$, $5.6\times10^6$, $5.7\times10^6$, $5.8\times10^6$, $5.9\times10^6$, $6\times10^6$, $6.5\times10^6$, $7\times10^6$, $7.5\times10^6$, $8\times10^6$, $8.5\times10^6$, $9\times10^6$, $9.5\times10^6$, $1\times10^7$, $1.5\times10^7$, $2\times10^7$, $2.5\times10^7$, $3\times10^7$, $3.5\times10^7$, $4\times10^7$, $4.5\times10^7$, $5\times10^7$, $5.5\times10^7$, $6\times10^7$, $6.5\times10^7$, $7\times10^7$, $7.5\times10^7$, $8\times10^7$, $8.5\times10^7$, $9\times10^7$, $9.5\times10^7$, $1\times10^8$, $1\times10^8$, $1.5\times10^8$, $2\times10^8$, $2.5\times10^8$, $3\times10^8$, $3.5\times10^8$, $4\times10^7$, $4.5\times10^8$, $5\times10^8$, $5.5\times10^8$, $6\times10^8$, $6.5\times10$, $7\times10^8$, $7.5\times10$, $8\times10^8$, $8.5\times10^8$, $9\times10^8$, $9.5\times10^8$, $1\times10^9$, or more Tregs per kg of recipient body weight, where Tregs are defined as CD4+CD25+CD127dim, CD3+CD4+CD25+, CD3+CD4+CD25+CD127dim, CD3+CD4+CD25+CD127dim FOXP3+, CD3+FOXP3+, CD3+CD4+FOXP3+, CD3+CD4+CD25+FOXP3+, CD3+CD25+FOXP3+, CD3+CD25+CD127dim, CD4+CD25-, CD4+CD25+CD127dimFOXP3+, FOXP3+, CD4+FOXP3+, CD4+CD25+FOXP3+, CD25+FOXP3+, or CD25+CD127dim.

A population of cells comprising Tregs administered to a subject can be administered, for example, at a dose of at most about $1\times10^4$, $1\times10^5$, $5\times10^5$, $6\times10^5$, $7\times10^5$, $8\times10^5$, $9\times10^5$, $1\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$, $4.5\times10^6$, $4.6\times10^6$, $4.7\times10^6$ $4.8\times10^6$, $4.9\times10^6$, $5\times10^6$, $5.1\times10^6$, $5.2\times10^6$, $5.3\times10^6$, $5.4\times10^6$, $5.5\times10^6$, $5.6\times10^6$, $5.7\times10^6$, $5.8\times10^6$, $5.9\times10^6$, $6\times10^6$, $6.5\times10^6$, $7\times10^6$, $7.5\times10^6$, $8\times10^6$, $8.5\times10^6$, $9\times10^6$, $9.5\times10^6$ $1\times10^7$, $1.5\times10^7$, $2\times10^7$, $2.5\times10^7$, $3\times10^7$, $3.5\times10^7$ $4\times10^7$, $4.5\times10^7$, $5\times10^7$, $5.5\times10^7$, $6\times10^7$ $6.5\times10^7$, $7\times10^7$, $7.5\times10^7$, $8\times10^7$, $8.5\times10^7$, $9\times10^7$, $9.5\times10^7$, $1\times10^7$, $1.5\times10^8$, $2\times10^8$, $2.5\times10^8$, $3\times10^8$, $3.5\times10^8$, $4\times10^7$, $4.5\times10^8$, $5\times10^8$, $5.5\times10^8$, $6\times10^8$, $6.5\times10^8$, $7\times10^8$, $7.5\times10^8$, $8\times10^8$, $8.5\times10^8$, $9\times10^8$, $9.5\times10^8$, $1\times10^9$, or less Tregs per kg of recipient body weight, where Tregs are defined as CD4+CD25+CD127dim, CD3+CD4+CD25+, CD3+CD4+CD25+CD127dim, CD3+CD4+CD25+CD127dim FOXP3+, CD3+FOXP3+, CD3+CD4+FOXP3+, CD3+CD4+CD25+FOXP3+, CD3+CD25+FOXP3+, CD3+CD25+CD127dim, CD4+CD25+, CD4+CD25+CD127dimFOXP3+, FOXP3+, CD4+FOXP3+, CD4+CD25+FOXP3+, CD25+FOXP3+, or CD25+CD127dim.

A population of cells comprising Tregs administered to a subject can be administered at a dose of $1\times10^4$ to $1\times10^9$, $1\times10^5$ to $1\times10^8$, $1\times10^5$ to $1\times10^7$, $5\times10^5$ to $1\times10^7$, $5\times10^5$ to $5\times10^6$, $5\times10^5$ to $4\times10^6$, $5\times10^5$ to $3\times10^6$, $5\times10^5$ to $2\times10^6$, $5\times10^5$ to $1\times10^6$, $1\times10^6$ to $1\times10^7$, $1\times10^6$ to $5\times10^6$, $1\times10^6$ to $4\times10^6$, $1\times10^6$ to $3\times10^6$, $1\times10^6$ to $2\times10^6$, $1\times10^6$ to $1.5\times10^6$, $1.5\times10^6$ to $1\times10$ $1.5\times10^6$ to $5\times10^6$, $1.5\times10^6$ to $4\times10^6$, $1.5\times10^6$ to $3\times10^6$, $1.5\times10^6$ to $2\times10^6$, $2\times10^6$ to $1\times10^7$, $2\times10^6$ to $5\times10^6$, $2\times10^6$ to $4\times10^6$, $2\times10^6$ to $3\times10^6$ $2\times10^6$ to $1\times10^7$, $2\times10^6$ to $5\times10^6$, $2\times10^6$ to $4\times10^6$ $2\times10^6$ to $3\times10^6$, $2\times10^6$ to $2\times10^6$, $2.5\times10^6$ to $1\times10^7$, $2.5\times10^6$ to $5\times10^6$, $2.5\times10^6$ to $4\times10^6$, or $2.5\times10^6$ to $3\times10^6$ cells per kg of recipient body weight.

In some embodiments, a population of cells comprising Tregs administered to a subject can be administered at a dose of $1\times10^4$ to $1\times10^9$, $1\times10^5$ to $1\times10^8$, $1\times10^5$ to $1\times10^7$, $5\times10^5$ to $1\times10^7$, $5\times10^5$ to $5\times10^6$, $5\times10^5$ to $4\times10^6$, $5\times10^5$ to $3\times10^6$, $5\times10^5$ to $2\times10^6$, $5\times10^5$ to $1\times10^6$, $1\times10^6$ to $1\times10^7$, $1\times10^6$ to $5\times10^6$, $1\times10^6$ to $4\times10^6$, $1\times10^6$ to $3\times10^6$, $1\times10^6$ to $2\times10^6$, $1\times10^6$ to $1.5\times10^6$, $1.5\times10^6$ to $1\times10^7$, $1.5\times10^6$ to $5\times10^6$, $1.5 \times 10^6$ to $4 \times 10^6$, $1.5 \times 10^6$ to $3 \times 10^6$, $1.5 \times 10^6$ to $2 \times 10^6$, $2 \times 10^6$ to $1 \times 10^7$, $2 \times 10^6$ to $5 \times 10^6$, $2 \times 10^6$ to $4 \times 10^6$, $2 \times 10^6$ to $3 \times 10^6$, $2 \times 10^6$ to $1 \times 10^7$ $2 \times 10^6$ to $5 \times 10^6$, $2 \times 10^6$ to $4 \times 10^6$, $2 \times 10^6$ to $3 \times 10^6$, $2 \times 10^6$ to $2 \times 10^6$, $2.5 \times 10^6$ to $1 \times 10^7$, $2.5 \times 10^6$ to $5 \times 10^6$, $2.5 \times 10^6$ to $4 \times 10^6$, or $2.5 \times 10^6$ to $3 \times 10^6$ Tregs per kg of recipient body weight, where Tregs are defined as CD4+CD25+CD127dim, CD3+CD4+CD25+, CD3+CD4+CD25+CD127dim, CD3+CD4+CD25+CD127dim FOXP3+, CD3+FOXP3+, CD3+CD4+FOXP3+, CD3+CD4+CD25+FOXP3+, CD3+CD25+FOXP3+, CD3+CD25+CD127dim, CD4+CD25+, CD4+CD25+CD127dimFOXP3, FOXP3+, CD4+FOXP3+, CD4+CD25+FOXP3+, CD25+FOXP3+, or CD25+CD127dim.

A population of cells comprising Tregs of the disclosure can comprise, for example, greater than at least about 50%, 51%, 52%, 53%, 54%, 55%, 5657%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more FOXP3+ cells as a percentage of total cells, nucleated cells, or CD45+ cells.

In some embodiments, a population of cells comprising Tregs of the disclosure comprises at most about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94% 95%, 96%, 97%, 98%, 99%, or less FOXP3+ cells as a percentage of total cells, nucleated cells, or CD451 cells.

A population of cells comprising Tregs of the disclosure can comprise, for example, greater than at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more CD4+CD25+CD127dim cells as a percentage of total cells, nucleated cells, or CD45+ cells.

In some embodiments, a population of cells comprising Tregs of the disclosure comprises at most about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or less CD4+CD25+CD127dim cells as a percentage of total cells, nucleated cells, or CD45+ cells.

For example, a population of cells comprising Tregs of the disclosure can comprise greater than at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more Tregs as a percentage of total cells, nucleated cells, or CD45+ cells, where Tregs are defined as CD4+CD25+CD127dim, CD3+CD4+CD25+, CD3+CD4+CD25+CD127dim, CD3+CD4+CD25+CD127dim FOXP3+, CD3+FOXP3+, CD3+CD4+FOXP3+, CD3+CD4+CD25+FOXP3+, CD3+CD25+FOXP3+, CD3+CD25+CD127dim, CD4+CD25+, CD4+CD25-CD127dimFOXP3+, FOXP3+, CD4+FOXP3+, CD4+CD25+FOXP3+, CD25+FOXP3+, or CD25+CD127dim.

In some embodiments, a population of cells comprising Tregs of the disclosure comprises at most about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or less Tregs as a percentage of total cells, nucleated cells, or CD45+ cells, where Tregs are defined as CD4+CD25+CD127dim, CD3+CD4+CD25+, CD3+CD4+CD25+CD127dim, CD3+CD4+CD25+CD127dim FOXP3+, CD3+FOXP3+, CD3+CD4+FOXP3+, CD3+CD4+CD25+FOXP3+, CD3+CD25+FOXP3+, CD3+CD25+CD127dim, CD4+CD25+, CD4+CD25+CD127dimFOXP3+, FOXP3+, CD4+FOXP3+, CD4+CD25+FOXP3+, CD25+FOXP3+, or CD25+CD127dim.

A population of cells comprising Tregs of the disclosure can comprise, for example, 50% to 100%, 60% to 100%, 70% to 100%, 75% to 100%, 80% to 100%, 81% to 100%, 82% to 100%, 83% to 100%, 84% to 100%, 84% to 100%, 86% to 100%, 87% to 100%, 88% to 100%, 89% to 100%, 90% to 91%, 92% to 100%, 93% to 100%, 94% to 100%, 95% to 100%, 96% to 100%, 97% to 100%, 98% to 100%, 99% to 100%, 99.5% to 100%, 50% to 99%, 60% to 99%, 70% to 99%, 80% to 99%, 81% to 99%, 82% to 99%, 83% to 99%, 84% to 99%, 85% to 99%, 86% to 99%, 87% to 99%, 88% to 99%, 89% to 99%, 90% to 99%, 91% to 99%, 92% to 99%, 94% to 99%, 95% to 99%, 96% to 97%, 98% to 99%, 50% to 98%, 60% to 98%, 70% to 98%, 80% to 98%, 81% to 98%, 82% to 98%, 83% to 98%, 84% to 98%, 85% to 98%, 86% to 98%, 87% to 98%, 88% to 98%, 89% to 98%, 90% to 98%, 91% to 98%, 92% to 98%, 94% to 98%, 95% to 98%, 96% to 97%, 98% to 98%, 50% to 97%, 60% to 97%, 70% to 97%, 80% to 97% 81% to 97%, 82% to 97%, 83% to 97%, 84% to 97%, 85% to 97%, 86% to 97%, 87% to 97%, 88% to 97%, 89% to 97%, 90% to 97%, 91% to 97%, 92% to 97%, 94% to 97%, 95% to 97%, 96% to 97%, 50% to 96%, 60% to 96%, 70% to 96%, 80% to 96%, 81% to 96%, 82% to 96%, 83% to 96%, 84% to 96%, 85% to 96%, 86% to 96%, 87% to 96%, 88% to 96%, 89% to 96%, 90% to 96%, 91% to 96%, 92% to 96%, 94% to 96%, 95% to 96%, 50% to 95%, 60% to 95%, 70% to 95%, 80% to 95%, 81% to 95%, 82% to 95%, 83% to 95%, 84% to 95%, 85% to 95%, 86% to 95%, 87% to 95%, 88% to 95%, 89% to 95%, 90% to 95%, 91% to 95%, 92% to 95%, or 94% to 95%, FOXP3+ cells as a percentage of nucleated cells, or as a percentage of CD45+ cells.

A population of cells comprising Tregs of the disclosure can comprise 50% to 100%, 60% to 100%, 70% to 100%, 75% to 100%, 80% to 100%, 81% to 100%, 82% to 100%, 83% to 100%, 84% to 100%, 84% to 100%, 86% to 100%, 87% to 100%, 88% to 100%, 89% to 100%, 90% to 91%, 92% to 0%, 93% to 100%, 94% to 100%, 95% to 100%, 96% to 100%, 97% to 100%, 98% to 100%, 99% to 100%, 99.5% to 100%, 50% to 99%, 60% to 99%, 97% to 99%, 80% to 99%, 81% to 99%, 82% to 99%, 83% to 99%, 84% to 99%, 85% to 99%, 86% to 99%, 87% to 99%, 88% to 99%, 89% to 99%, 90% to 99%, 91 to 99%, 92% to 99%, 94% to 99%, 95% to 99%, 96% to 97%, 98% to 99%, 50% to 98%, 60% to 98%, 70% to 98%, 80% to 98%, 81% to 98%, 82% to 98%, 83% to 98%, 84% to 98%, 85% to 98%, 86% to 98%, 87% to 98%, 88% to 98%, 89% to 98%, 90% to 98%, 91 to 98%, 92% to 98%, 94% to 98%, 95% to 98%, 96% to 97%, 98% to 98%, 50% to 97%, 60% to 97%, 70% to 97%, 8% to 97%, 81 to 97%, 82% to 97%, 83% to 97%, 84% to 97%, 85% to 97%, 86% to 97%, 87% to 97%, 88% to 97%, 89% to 97%, 90% to 97%, 91% to 97%, 92% to 97%, 94% to 97%, 95% to 97%, 96% to 97%, 50% to 96%, 60% to 96%, 70% to 96%, 80% to 96%, 81% to 96%, 82% to 96%, 83% to 96%, 84% to 96%, 85% to 96%, 86% to 96%, 87% to 96%, 88% to 96%, 89% to 96%, 90% to 96%, 91% to 96%, 92% to 96%, 94% to 96%, 95% to 96%, 50% to 95%, 60% to 95% 70% to 95%, 80% to 95%, 81% to 95%, 82% to 95%, 83% to 95%, 84% to 95%, 85% to 95%, 86% to 95%, 87% to 95%, 88% to 95%, 89% to 95%, 90% to 95%, 91% to 95%, 92% to 95%, or 94% to 95%, Tregs as a percentage of total cells, nucleated cells, or CD45+ cells, where Tregs are defined as CD4+CD25+CD127dim, CD3+CD4+CD25+, CD3+CD4+CD25+CD127dim, CD3+CD4+CD25+ CD127dim FOXP3+, CD3+FOXP3+, CD3+CD4+FOXP3+, CD3+CD4+CD25+FOXP3+, CD3+CD25+FOXP3+, CD3+ CD25+CD127dim, CD4+CD25+, CD4+CD25+ CD127dimFOXP3+, FOXP3+, CD4+FOXP3+, CD4+ CD25+FOXP3+, CD25+FOXP3+, or CD25+CD127dim.

A population of cells comprising Tregs of the disclosure can have a defined level of contaminating non-Treg cells.

For example, greater than at least about $1 \times 10^2$, $2 \times 10^2$, $3 \times 10^2$, $4 \times 10^2$, $5 \times 10^2$, $6 \times 10^2$ $7 \times 10^2$, $8 \times 10^2$, $9 \times 10^2$, $1 \times 10^3$, $2 \times 10^3$, $3 \times 10^3$, $4 \times 10^3$, $5 \times 10^3$, $6 \times 10^3$, $7 \times 10^3$, $8 \times 10^3$, $9 \times 10^3$, $1 \times 10^7$, $2 \times 10^4$, $3 \times 10^4$, $4 \times 10^4$, $5 \times 10^4$, $6 \times 10^4$, $7 \times 10^4$, $8 \times 10^4$ $9 \times 10^4$, $1 \times 10^5$, or more non-Treg cells per kg of recipient body weight can be present in population of cells comprising Tregs of the disclosure, where non-Treg cells are FOXP3− or CD127+/bright.

In some embodiments, at most about $1 \times 10^2$, $2 \times 10^2$, $3 \times 10^2$, $4 \times 10^2$, $5 \times 10^2$, $6 \times 10^2$, $7 \times 10^2$, $8 \times 10^2$, $9 \times 10^2$, $1 \times 10^3$, $2 \times 10^3$, $3 \times 10^3$, $4 \times 10^3$, $5 \times 10^3$, $6 \times 10^3$, $7 \times 10^3$, $8 \times 10^3$, $9 \times 10^3$, $1 \times 10^4$, $2 \times 10^4$, $3 \times 10^4$, $4 \times 10^4$, $5 \times 10^4$, $6 \times 10^4$, $7 \times 10^4$, $8 \times 10^4$, $9 \times 10^4$, $1 \times 10^5$, or less non-Treg cells per kg of recipient body weight are present in a population of cells comprising Tregs of the disclosure, where non-Treg cells are FOXP3- or CD127-f-bright.

A population of cells comprising Tregs of the disclosure can comprise, for example, greater than at least about 0.001%, 0.002%, 0.003%, 0.004%, 0.005%, 0.006%, 0.007%, 0.008% 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 5%, 6%, 7%, 8%, 9%, 10%, or more non-Treg cells as a percentage of total cells, nucleated cells, or CD45+ cells, where non-Treg cells are FOXP3− or CD127+/bright.

In some embodiments, a population of cells comprising Tregs of the disclosure comprises at most about 0.001%, 0.002%, 0.003%, 0.004%, 0.005%, 0006%, 0.007%, 0.008% 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 11%, 1.2%, 1.3%, 1.4%, 1.5%, 1.6%, 1.7%, 1.8%, 1.9%, 2% 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 5%, 6%, 7%, 8%, 9%, 10%, or less non-Treg cells as a percentage of total cells, nucleated cells, or CD45+ cells, where non-Treg cells are FOXP3− or CD127+/bright.

Tcons

A population of Tcons administered to a subject can be administered, for example, at a dose greater than at least about $1 \times 10^4$, $1 \times 10^5$, $2 \times 10^5$, $3 \times 10^5$, $4 \times 10^5$, $5 \times 10^5$, $6 \times 10^5$, $7 \times 10^5$, $8 \times 10^5$, $9 \times 10^5$, $1 \times 10^6$, $1.1 \times 10^6$, $1.2 \times 10^6$, $1.3 \times 10^6$, $1.4 \times 10^6$, $1.5 \times 10^6$, $1.6 \times 10^6$, $1.7 \times 10^6$, $1.8 \times 10^6$, $1.9 \times 10^6$, $2 \times 10^6$, $2.1 \times 10^6$, $2.2 \times 10^6$, $2.3 \times 10^6$, $2.4 \times 10^6$, $2.5 \times 10^6$, $2.6 \times 10^6$, $2.7 \times 10^6$, $2.8 \times 10^6$, $2.9 \times 10^6$, $3 \times 10^6$, $3.1 \times 10^6$, $3.2 \times 10^6$, $3.3 \times 10^6$, $3.4 \times 10^6$, $3.5 \times 10^6$, $3.6 \times 10^6$, $3.7 \times 10^6$, $3.8 \times 10^6$, $3.9 \times 10^6$, $4 \times 10^6$, $4.1 \times 10^6$, $4.2 \times 10^6$, $4.3 \times 10^6$, $4.4 \times 10^6$, $4.5 \times 10^6$, $4.6 \times 10^6$, $4.7 \times 10^6$, $4.8 \times 10^6$, $4.9 \times 10^6$, $5 \times 10^6$, $5.1 \times 10^6$, $5.2 \times 10^6$, $5.3 \times 10^6$, $5.4 \times 10^6$, $5.5 \times 10^6$, $5.6 \times 10^6$, $5.7 \times 10^6$, $5.8 \times 10^6$, $5.9 \times 10^6$, $6 \times 10^6$ $6.5 \times 10^6$ $7 \times 10^6$, $7.5 \times 10^6$, $8 \times 10^6$, $8.5 \times 10^6$, $9 \times 10^6$, $9.5 \times 10^6$, $1 \times 10^7$, $1.5 \times 10^7$, $2 \times 10^7$, $2.5 \times 10^7$, $3 \times 10^7$, $3.5 \times 10^7$, $4 \times 10^7$, $4.5 \times 10^7$, $5 \times 10^7$, $5.5 \times 10^7$, $6 \times 10^7$, $6.5 \times 10^7$, $7 \times 10^7$, $7.5 \times 10^7$, $8 \times 10^7$, $8.5 \times 10^7$, $9 \times 10^7$, $9.5 \times 10^7$, $1 \times 10^8$, $1 \times 10^7$, $1.5 \times 10^8$, $2 \times 10^8$, $2.5 \times 10^8$, $3 \times 10^8$, $3.5 \times 10^8$, $4 \times 10^7$, $4.5 \times 10^8$, $5 \times 10^8$, $5.5 \times 10^8$, $6 \times 10^8$, $6.5 \times 10^8$, $7 \times 10^8$, $7.5 \times 10^8$, $8 \times 10^8$, $8.5 \times 10^8$, $9 \times 10^8$, $9.5 \times 10^8$, $1 \times 10^9$, or more cells per kg of recipient body weight.

In some embodiments, a population of Tcons administered to a subject can be administered at a dose of at most about $1 \times 10^4$, $\times 10^5$, $2 \times 10^5$, $3 \times 10^5$, $4 \times 10^5$, $5 \times 10^5$, $6 \times 10^5$, $7 \times 10^5$, $8 \times 10^5$, $9 \times 10^5$, $1 \times 10^6$, $1.1 \times 10^6$, $1.2 \times 10^6$, $1.3 \times 10^6$, $1.4 \times 10^6$, $1.5 \times 10^6$, $1.6 \times 10^6$, $1.7 \times 10^6$, $1.8 \times 10^6$, $1.9 \times 10^6$, $2 \times 10^6$, $2.1 \times 10^6$, $2.2 \times 10^6$, $2.3 \times 10^6$, $2.4 \times 10^6$, $2.5 \times 10^6$ $2.6 \times 10^6$, $2.7 \times 10^6$, $2.8 \times 10^6$, $2.9 \times 10^6$, $3 \times 10^6$, $3.1 \times 10^6$, $3.2 \times 10^6$, $3.3 \times 10^6$, $3.4 \times 10^6$, $3.5 \times 10^6$, $3.6 \times 10^6$, $3.7 \times 10^6$, $3.8 \times 10^6$, $3.9 \times 10^6$, $4 \times 10^6$, $4.1 \times 10^6$, $4.2 \times 10^6$, $4.3 \times 10^6$, $4.4 \times 10^6$, $4.5 \times 10^6$, $4.6 \times 10^6$, $4.7 \times 10^6$, $4.8 \times 10^6$, $4.9 \times 10^6$, $5 \times 10^6$, $5.1 \times 10^6$, $5.2 \times 10^6$, $5.3 \times 10^6$, $5.4 \times 10^6$, $5.5 \times 10^6$, $5.6 \times 10^6$, $5.7 \times 10^6$, $5.8 \times 10^6$, $5.9 \times 10^6$, $6 \times 10^6$, $6.5 \times 10^6$, $7 \times 10^6$, $7.5 \times 10^6$, $8 \times 10^6$, $8.5 \times 10^6$, $9 \times 10^6$, $9.5 \times 10^6$, $\times 10^7$, $1.5 \times 10^7$, $2 \times 10^7$, $2.5 \times 10^7$, $3 \times 10^7$, $3.5 \times 10^7$, $4 \times 10^7$, $4.5 \times 10^7$, $5 \times 10^7$, $5.5 \times 10^7$, $6 \times 10^7$, $6.5 \times 10^7$, $7 \times 10^7$, $7.5 \times 10^7$, $8 \times 10^7$, $8.5 \times 10^7$, $9 \times 10^7$, $9.5 \times 10^7$, $1 \times 10^8$, $1 \times 10^8$, $1.5 \times 10^8$, $2 \times 10^8$, $2.5 \times 10^8$, $3 \times 10$, $3.5 \times 10^7$, $4 \times 10^7$, $4.5 \times 10^8$, $5 \times 10^7$, $5.5 \times 10^8$, $6 \times 10^8$, $6.5 \times 10^8$, $7 \times 10^8$, $7.5 \times 10^8$, $8 \times 10^8$, $8.5 \times 10^8$, $9 \times 10^8$, $9.5 \times 10^8$, $1 \times 10^9$, or less cells per kg of recipient body weight.

A population of Tcons administered to a subject can be administered at a dose greater than at least about $1 \times 10^5$, $2 \times 10^5$, $3 \times 10^5$ $4 \times 10^5$, $5 \times 10^5$, $6 \times 10^5$, $7 \times 10^5$, $8 \times 10^5$, $9 \times 10^5$, $1 \times 10^6$, $1.1 \times 10^6$, $1.2 \times 10^6$, $1.3 \times 10^6$, $1.4 \times 10^6$, $1.5 \times 10^6$, $1.6 \times 10^6$, $1.7 \times 10^6$, $1.8 \times 10^6$, $1.9 \times 10^6$, $2 \times 10^6$, $2.1 \times 10^6$, $2.2 \times 10^6$, $2.3 \times 10^6$, $2.4 \times 10^6$, $2.5 \times 10^6$, $2.6 \times 10^6$, $2.7 \times 10^6$, $2.8 \times 10^6$, $2.9 \times 10^6$, $3 \times 10^6$ $3.1 \times 10^6$, $3.2 \times 10^6$ $3.3 \times 10^6$ $3.4 \times 10^6$, $3.5 \times 10^6$ $3.6 \times 10^6$ $3.7 \times 10^6$, $3.8 \times 10^6$, $3.9 \times 10^6$, $4 \times 10^6$, $4.1 \times 10^6$, $4.2 \times 10^6$, $4.3 \times 10^6$, $4.4 \times 10^6$, $4.5 \times 10^6$, $4.6 \times 10^6$, $4.7 \times 10^6$, $4.8 \times 10^6$, $4.9 \times 10^6$, $5 \times 10^6$, $5.1 \times 10^6$, $5.2 \times 10^6$, $5.3 \times 10^6$, $5.4 \times 10^6$, $5.5 \times 10^6$, $5.6 \times 10^6$, $5.7 \times 10^6$ $5.8 \times 10^6$, $5.9 \times 10^6$, $6 \times 10^6$, $6.5 \times 10^6$, $7 \times 10^6$, $7.5 \times 10^6$, $8 \times 10^6$, $8.5 \times 10^6$, $9 \times 10^6$, $9.5 \times 10^6$, $1 \times 10^7$, $1.5 \times 10^7$, $2 \times 10^7$, $2.5 \times 10^7$, $3 \times 10^7$, $3.5 \times 10^7$, $4 \times 10^7$, $4.5 \times 10^7$, $5 \times 10^7$, $5.5 \times 10^7$, $6 \times 10^7$, $6.5 \times 10^7$, $7 \times 10^7$, $7.5 \times 10^7$, $8 \times 10^7$, $8.5 \times 10^7$, $9 \times 10^7$, $9.5 \times 10^7$, $1 \times 10^8$, $1 \times 10^7$, $1.5 \times 10^7$, $2 \times 10^8$, $2.5 \times 10^8$, $3 \times 10^8$, $3.5 \times 10^8$, $4 \times 10^7$, $4.5 \times 10^8$, $5 \times 10^8$, $5.5 \times 10^8$, $6 \times 10^8$, $6.5 \times 10^7$, $7 \times 10^8$, $7.5 \times 10^8$, $8 \times 10^8$, $8.5 \times 10^8$, $9 \times 10^8$, $9.5 \times 10^8$, $1 \times 10^9$, or more Tcons per kg of recipient body weight, where Tcons are defined as CD3+.

A population of Tcons administered to a subject can be administered at a dose of at most about $1 \times 10^4$, $1 \times 10^5$, $5 \times 10^5$, $6 \times 10^5$, $7 \times 10^5$, $8 \times 10^5$, $9 \times 10^5$, $1 \times 10^6$, $1.1 \times 10^6$, $1.2 \times 10^6$, $0.3 \times 10^6$, $1.4 \times 10^6$, $1.5 \times 10^6$, $1.6 \times 10^6$, $1.7 \times 10^6$, $1.8 \times 10^6$, $1.9 \times 10^6$ $2 \times 10^6$, $2.1 \times 10^6$, $2.2 \times 10^6$ $2.3 \times 10^6$, $2.4 \times 10^6$, $2.5 \times 10^6$, $2.6 \times 10^6$, $2.7 \times 10^6$, $2.8 \times 10^6$, $2.9 \times 10^6$, $3 \times 10^6$, $3.1 \times 10^6$, $3.2 \times 10^6$, $3.3 \times 10^6$, $3.4 \times 10^6$, $3.5 \times 10^6$, $3.6 \times 10^6$, $3.7 \times 10^6$, $3.8 \times 10^6$, $3.9 \times 10^6$, $4 \times 10^6$, $4.1 \times 10^6$, $4.2 \ 10^6$, $4.3 \times 10^6$, $4.4 \times 10^6$, $4.5 \times 10^6$, $4.6 \times 10^6$, $4.7 \times 10^6$, $4.8 \times 10^6$, $4.9 \times 10^6$, $5 \times 10^6$, $5.1 \times 10^6$, $5.2 \times 10^6$, $5.3 \times 10^6$, $5.4 \times 10^6$, $5.5 \times 10^6$, $5.6 \times 10^6$, $5.7 \times 10^6$, $5.8 \times 10^6$, $5.9 \times 10^6$, $6 \times 10^6$, $6.5 \times 10^6$, $7 \times 10^6$, $7.5 \times 10^6$, $8 \times 10^6$, $8.5 \times 10^6$, $9 \times 10^6$, $9.5 \times 10^6$, $1 \times 10^7$, $1.5 \times 10^7$, $2 \times 10^7$, $2.5 \times 10^7$, $3 \times 10^7$, $3.5 \times 10^7$, $4 \times 10^7$, $4.5 \times 10^7$, $S \times 10^7$, $5.5 \times 10^7$, $6 \times 10^7$, $6.5 \times 10^7$, $7 \times 10^7$, $7.5 \times 10^7$, $8 \times 10^7$, $8.5 \times 10^7$, $9 \times 10^7$, $9.5 \times 10^7$, $1 \times 10^8$, $1 \times 10^8$, $1.5 \times 10^7$, $2 \times 10^8$, $2.5 \times 10^8$, $3 \times 10^8$, $3.5 \times 10^8$, $4 \times 10^7$, $4.5 \times 10^8$, $5 \times 10^8$, $5.5 \times 10^8$, $6 \times 10^8$, $6.5 \times 10^8$, $7 \times 10^8$, $7.5 \times 10^8$, $8 \times 10^8$, $8.5 \times 10^8$, $9 \times 10^8$, $9.5 \times 10^8$, $1 \times 10^9$, or less Tcons per kg of recipient body weight, where Tcons are defined as CD3+.

In some embodiments, a population of Tcons administered to a subject can be administered at a dose of $1\times10^4$ to $1\times10^9$, $1\times10^5$ to $1\times10^8$, $1\times10^5$ to $1\times10^7$, $5\times10^5$ to $1\times10^7$, $5\times10^5$ to $5\times10^6$, $5\times10^5$ to $4\times10^6$, $5\times10^5$ to $3\times10^6$, $5\times10^5$ to $2\times10^6$, $5\times10^5$ to $1\times10^6$, $1\times10^6$ to $1\times10^7$, $1\times10^6$ to $5\times10^6$, $1\times10^6$ to $4\times10^6$, $1\times10^6$ to $3\times10^6$, $1\times10^6$ to $2\times10^6$, $1\times10^6$ to $1.5\times10^6$, $1.5\times10^6$ to $1\times10^7$, $1.5\times10^6$ to $5\times10^6$, $1.5\times10^6$ to $4\times10^6$, $1.5\times10^6$ to $3\times10^6$, $1.5\times10^6$ to $2\times10^6$, $2\times10^6$ to $1\times10^7$, $2\times10^6$ to $5\times10^6$, $2\times10^6$ to $4\times10^6$, $2\times10^6$ to $3\times10^6$, $2\times10^6$ to $1\times10$, $2\times10^6$ to $5\times10^6$, $2\times10^6$ to $4\times10^6$, $2\times10^6$ to $3\times10^6$, $2\times10^6$ to $2\times10^6$, $2.5\times10^6$ to $1\times10^7$, $2.5\times10^6$ to $5\times10^6$, $2.5\times10^6$ to $4\times10^6$, or $2.5\times10^6$ to $3\times10^6$ cells per kg of recipient body weight.

In some embodiments, a population Tcons administered to a subject can be administered at a dose of $1\times10^4$ to $1\times10^9$, $1\times10^5$ to $1\times10^8$, $1\times10^5$ to $1\times10^7$, $5\times10^5$ to $1\times10^7$, $5\times10^5$ to $5\times10^6$, $5\times10^5$ to $4\times10^6$, $5\times10^5$ to $3\times10^6$, $5\times10^5$ to $2\times10^6$, $5\times10^5$ to $1\times10^6$, $1\times10^6$ to $1\times10^7$, $1\times10^6$ to $5\times10^6$, $1\times10^6$ to $4\times10^6$, $1\times10^6$ to $3\times10^6$, $1\times10^6$ to $2\times10^6$, $1\times10^6$ to $1.5\times10^6$, $1.5\times10^6$ to $1\times10^7$, $1.5\times10^6$ to $5\times10^6$, $1.5\times10^6$ to $4\times10^6$, $1.5\times10^6$ to $3\times10^6$, $1.5\times10^6$ to $2\times10^6$, $2\times10^6$ to $1\times10^7$, $2\times10^6$ to $5\times10^6$, $2\times10^6$ to $4\times10^6$, $2\times10^6$ to $3\times10^6$, $2\times10^6$ to $1\times10^7$, $2\times10^6$ to $5\times10^6$, $2\times10^6$ to $4\times10^6$, $2\times10^6$ to $3\times10^6$, $2\times10^6$ to $2\times10^6$, $2.5\times10^6$ to $1\times10^7$, $2.5\times10^6$ to $5\times10^6$, $2.5\times10^6$ to $4\times10^6$, or $2.5\times10^6$ to $3\times10^6$ Tcons per kg of recipient body weight, where Tcons are defined as CD3+.

A population Tcons of the disclosure can comprise greater than at least about 5%, 10%, 20%, 30%, 40%, 50%, 51%, 52%, 53%, 54%, 55%, 56%, 57% 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93% 94% 95%, 96%, 97%, 98%, 99%, or more CD3+ cells as a percentage of total cells, nucleated cells, or CD45+ cells.

A population Tcons of the disclosure can comprise at most about 5%, 10%, 20%, 30%, 40%, 50% 51%, 52%, 53%, 54%, 55%, 56%, 57% 58%, 59% 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or less CD3+ cells as a percentage of total cells, nucleated cells, or CD45+ cells.

For example, a population Tcons of the disclosure can comprise between about 10% to 100%, 10% to 90%, 10% to 80%, 10% to 70%, 10% to 60%, 10% to 50%, 10% to 40%, 10% to 30%, 10% to 20%, 20% to 100%, 20% to 90%, 20% to 80%, 20% to 70%, 20% to 60%, 20% to 50%, 20% to 40%, 20% to 30%, 30% to 100%, 30% to 90%, 30% to 80%, 30% to 70%, 30% to 60%, 30% to 50%, 30% to 40%, 40% to 100%, 40% to 90%, 40% to 80%, 40% to 70%, 40% to 60%, 40% to 50%, 50% to 100%, 50% to 90%, 50% to 80%, 50% to 70%, 50% to 60%, 60% to 100%, 60% to 90%, 60% to 80%, 60% to 70%, 70% to 100%, 70% to 90%, 70% to 80%, 80% to 100%, 80% to 90%, or 90% to 100% CD3+ cells as a percentage of total cells, nucleated cells, or CD45+ cells.

iNKTs

A population of iNKTs administered to a subject can be administered at a dose greater than at least about $1\times10^4$, $1\times10^5$, $5\times10^5$, $6\times10^5$, $7\times10^5$, $8\times10^5$, $9\times10^5$, $1\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2\times10^6$, $2.1\times10^6$, $2.2\times10^6$ $2.3\times10^6$, $2.4\times10^6$ $2.5\times10^6$ $2.6\times10^6$, $2.7\times10^6$ $2.8\times10^6$ $2.9\times10^6$, $3\times10^6$ $3\times10^6$, $3.2\times10^6$ $3.3\times10^6$, $3.4\times10^6$, $3.5\times10^6$, $3.6\times10^6$, $3.7\times10^6$, $3.8\times10^6$, $3.9\times10^6$ $4\times10^6$, $4.1\times10^6$, $4.2\times10^6$ $4.3\times10^6$ $4.4\times10^6$ $4.5\times10^6$, $4.6\times10^6$ $4.7\times10^6$ $4.8\times10^6$ $4.9\times10^6$, $5\times10^6$, $5.1\times10^6$ $5.2\times10^6$ $5.3\times10^6$, $5.4\times10^6$ $5.5\times10^6$, $5.6\times10^6$ $5.7\times10^6$ $5.8\times10^6$ $5.9\times10^6$, $6\times10^6$, $6.5\times10^6$, $7\times10^6$, $7.5\times10^6$, $8\times10^6$, $8.5\times10^6$, $9\times10^6$, $1\times10^7$, $1.5\times10^7$, $2\times10^7$, $2.5\times10^7$ $3\times10^7$ $3.5\times10^7$, $4\times10^7$, $4.5\times10^7$, $5\times10^7$, $5.5\times10^7$, $6\times10^7$, $6.5\times10^7$, $7\times10^7$, $7.5\times10^7$, $8\times10^7$, $8.5\times10^7$, $9\times10^7$, $9.5\times10^7$, $1\times10^8$, $1\times10^8$, $1.5\times10^8$, $2\times10^8$, $2.5\times10^8$, $3\times10^8$, $3.5\times10^7$, $4\times10^7$, $4.5\times10^8$, $5\times10^8$, $5.5\times10^8$, $6\times10^8$, $6.5\times10^8$, $7\times10^8$, $7.5\times10^8$, $8\times10^8$, $8.5\times10^8$, $9\times10^8$, $9.5\times10^8$, $1\times10^9$, or more cells per kg of recipient body weight.

A population of iNKTs administered to a subject can be administered at a dose of at most about $1\times10^4$, $1\times10^5$, $5\times10^5$ $6\times10^5$, $7\times10^5$, $8\times10^5$, $9\times10^5$, $1\times10^6$, $1.1\times10^6$, $1.2\times10^6$, $0.3\times10^6$, $1.4\times10^6$, $1.5\times10^6$, $1.6\times10^6$, $1.7\times10^6$, $1.8\times10^6$, $1.9\times10^6$, $2\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$, $3\times10^6$, $3.1\times10^6$, $3.2\times10^6$, $3.3\times10^6$, $3.4\times10^6$ $3.5\times10^6$ $3.6\times10^6$, $3.7\times10^6$ $3.8\times10^6$ $3.9\times10^6$, $4\times10^6$, $4.1\times10^6$, $4.2\times10^6$, $4.3\times10^6$, $4.4\times10^6$, $4.5\times10^6$, $4.6\times10^6$, $4.7\times10^6$, $4.8\times10^6$, $4.9\times10^6$, $5\times10^6$, $5\times10^6$, $5.2\times10^6$, $5.3\times10^6$, $5.4\times10^6$, $5.5\times10^6$, $5.6\times10^6$, $5.7\times10^6$, $5.8\times10^6$ $5.9\times10^6$ $6\times10^6$ $6.5\times10^6$, $7\times10^6$, $7.5\times10^6$, $8\times10^6$, $8.5\times10^6$, $9\times10^6$, $9.5\times10^6$, $1\times10^7$, $1.5\times10_7$, $2\times10^7$, $2.5\times10^7$, $3\times10^7$, $3.5\times10^7$, $4\times10^7$, $4.5\times10^7$, $5\times10^7$, $5.5\times10^7$, $6\times10^7$, $6.5\times10^7$, $7\times10^7$ $7.5\times10^7$, $8\times10^7$, $8.5\times10^7$, $9\times10^7$, $9.5\times10^7$, $1\times10^8$, $1\times10^8$, $1.5\times10^8$, $2\times10^8$, $2.5\times10^7$, $3\times10^8$, $3.5\times10^8$, $4\times10^7$, $4.5\times10^8$, $5\times10^8$, $5.5\times10^8$, $6\times10^8$, $6.5\times10^8$, $7\times10^8$, $7.5\times10^7$, $8\times10^8$, $8.5\times10^8$, $9\times10^8$, $9.5\times10^8$, $1\times10^9$, or less cells per kg of recipient body weight.

In some embodiments, a population of iNKTs administered to a subject can be administered at a dose greater than at least about $1\times10^4$, $1\times10^5$ $5\times10^5$, $6\times10^5$, $7\times10^5$, $8\times10^5$, $9\times10^5$, $1\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2\times10^6$ $2.1\times10^6$, $2.2\times10^6$ $2.3\times10^6$, $2.4\times10^6$, $2.5\times10^6$, $2.6\times10^6$, $2.7\times10^6$, $2.8\times10^6$, $2.9\times10^6$, $3\times10^6$ $3.1\times10^6$ $3.2\times10^6$, $3.3\times10^6$ $3.4\times10^6$, $3.5\times10^6$, $3.6\times10^6$ $3.7\times10^6$, $3.8\times10^6$, $3.9\times10^6$, $4\times10^6$, $4.1\times10^6$, $4.2\times10^6$, $4.3\times10^6$, $4.4\times10^6$, $4.5\times10^6$, $4.6\times10^6$, $4.7\times10^6$, $4.8\times10^6$, $4.9\times10^6$, $5\times10^6$, $5.1\times10^6$, $5.2\times10^6$, $5.3\times10^6$, $5.4\times10^6$, $5.5\times10^6$, $5.6\times10^6$, $5.7\times10^6$, $5.8\times10^6$, $5.9\times10^6$, $6\times10^6$, $6.5\times10^6$ $7\times10^6$, $7.5\times10^6$, $8\times10^6$, $8.5\times10^6$, $9\times10^6$, $9.5\times10^6$, $1\times10^7$, $1.5\times10^7$, $2\times10^7$, $2.5\times10^7$, $3\times10^7$, $3.5\times10^7$, $4\times10^7$, $4.5\times10^7$, $5\times10^7$, $5.5\times10^7$, $6\times10^7$ $6\times10^7$, $7\times10^7$, $7.5\times10^7$, $8\times10^7$, $8.5\times10^7$, $9\times10^7$, $9.5\times10^7$, $1\times10^8$, $1\times10^8$, $1.5\times10^7$, $2\times10^8$, $2.5\times10^8$, $3\times10^7$, $3.5\times10^8$, $4\times10^7$, $4.5\times10^8$, $5\times10^8$, $5.5\times10^8$, $6\times10^8$, $6.5\times10^7$, $7\times10^8$, $7.5\times10^8$, $8\times10^8$, $8.5\times10$, $9\times10^8$, $9.5\times10^8$, $1\times10^9$, or more CD3+Vα24Jα18+ cells per kg of recipient body weight.

In some embodiments, a population of iNKTs administered to a subject can be administered at a dose of at most about $1\times10^4$, $1\times10^5$, $5\times10^5$, $6\times10^5$, $7\times10^5$, $8\times10^5$, $9\times10^5$, $1\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$, $3\times 10^6$, $3.1\times10^6$ $3.2\times10^6$, $3.3\times10^6$, $3.4\times10^6$, $3.5\times10^6$ $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$, $4.5\times10^6$, $4.6\times10^6$, $4.7\times10^6$, $4.8\times10^6$, $4.9\times10^6$, $5\times10^6$, $5.1\times10^6$, $5.2\times10^6$, $5.3\times10^6$, $5.4\times10^6$, $5.5\times10^6$, $5.6\times10^6$, $5.7\times10^6$, $5.8\times10^6$, $5.9\times10^6$, $6\times10^6$, $6.5\times10^6$, $7\times10^6$, $7.5\times10^6$, $8\times10^6$, $8.5\times10^6$, $9\times10^6$, $9.5\times10^6$, $1\times10^7$, $1.5\times10^7$, $2\times10^7$, $2.5\times10^7$, $3\times10^7$, $3.5\times10^7$, $4\times10^7$, $4.5\times10^7$, $5\times10^7$, $5.5\times10^7$, $6\times10^7$, $6.5\times10^7$, $7\times10^7$, $7.5\times10^7$, $8\times10^7$, $8.5\times10^8$, $9\times10^8$, $9.5\times10^7$, $1\times10^7$, $1\times10^8$, $1.5\times10^8$, $2\times10^8$, $2.5\times10^8$, $3\times10^8$, $3.5\times10^8$, $4\times10^7$, $4.5\times10^8$, $10^8$, $5.5\times10^8$, $6\times10^8$, $6.5\times10^8$, $7\times10^8$, $7.5\times10^8$, $8\times10^8$, $8.5\times10^8$, $9\times10^8$, $9.5\times10^8$, $1\times10^9$, or less CD3'Vα24Jα18+ cells per kg of recipient body weight.

A population of iNKTs administered to a subject can be administered at a dose, for example, of $1\times10^4$ to $1\times10^9$, $1\times10^5$ to $1\times10^8$, $1\times10^5$ to $2\times10^7$, $5\times10^5$ to $2\times10^7$, $5\times10^5$ to $1.5\times10^7$, $5\times10^5$ to $1\times10^7$, $5\times10^5$ to $9\times10^6$, $5\times10^5$ to $8\times10^6$, $5\times15$ to $7\times10^6$, $5\times05$ to $6\times10^6$, $5\times10^5$ to $5\times10^6$, $5\times10^5$ to $4\times10^6$, $5\times10^5$ to $3\times10^6$, $5\times10^5$ to $2\times10^6$, $5\times10^5$ to $1\times10^6$, $1\times10^6$ to $1.5\times10^7$, $1\times10^6$ to $1\times10^7$, $1\times10^6$ to $9\times10^6$, $\times10^6$ to $8\times10^6$, $1\times10^6$ to $7\times10^6$, $1\times10^6$ to $6\times10^6$, $1\times10^6$ to $5\times10^6$, $1\times10^6$ to $4\times10^6$, $1\times10^6$ to $3\times10^6$, $1\times10^6$ to $2\times10^6$, $1.5\times10^6$ to $1.5\times10^7$, $1.5\times10^6$ to $1\times10^7$, $1.5\times10^6$ to $9\times10^6$, $1.5\times10^6$ to $8\times10^6$, $1.5\times10^6$ to $7\times10^6$, $1.5\times10^6$ to $6\times10^6$, $1.5\times10^6$ to $5\times10^6$, $1.5\times10^6$ to $4\times10^6$, $1.5\times10^6$ to $3\times10^6$, $1.5\times10^6$ to $2\times10^6$, $2\times10^6$ to $1.5\times10^7$, $2\times10^6$ to $1\times10^7$, $2\times10^6$ to $9\times10^6$, $2\times10^6$ to $8\times10^6$, $2\times10^6$ to $7\times10^6$, $2\times10^6$ to $6\times10^6$, $2\times10^6$ to $5\times10^6$, $2\times10^6$ to $4\times10^6$, $2\times10^6$ to $3\times10^6$, $2.5\times10^6$ to $1.5\times10^7$, $2.5\times10^6$ to $1\times10^7$ $2.5\times10^6$ to $9\times10^6$, $2.5\times10^6$ to $8\times10^6$, $2.5\times10^6$ to $7\times10^6$, $2.5\times10^6$ to $6\times10^6$, $2.5\times10^6$ to $5\times10^6$, $2.5\times10^6$ to $4\times10^6$, or $2.5\times10^6$ to $3\times10^6$ cells per kg of recipient body weight.

A population of iNKTs administered to a subject can be administered at a dose of $1\times10^4$ to $1\times10^9$, $1\times10^5$ to $1\times10^8$, $1\times10^5$ to $2\times10^7$, $5\times10^5$ to $2\times10^7$, $5\times10^5$ to $1.5\times10^7$, $5\times10^5$ to $1\times10^7$, $5\times10^5$ to $9\times10^6$, $5\times10^5$ to $8\times10^6$, $5\times10^5$ to $7\times10^6$, $5\times10^5$ to $6\times10^6$, $5\times10^5$ to $5\times10^6$, $5\times10^5$ to $4\times10^6$, $5\times10^5$ to $3\times10^6$, $5\times10^5$ to $2\times10^6$, $5\times10^5$ to $1\times10^6$, $1\times10^6$ to $1.5\times10^7$, $1\times10^6$ to $1\times10$, $1\times10^6$ to $9\times10^6$, $1\times10^6$ to $8\times10^6$, $1\times10^6$ to $7\times10^6$, $1\times10^6$ to $6\times10^6$, $1\times10^6$ to $5\times10^6$, $1\times10^6$ to $4\times10^6$, $1\times10^6$ to $3\times10^6$, $1\times10^6$ to $2\times10^6$, $1.5\times10^6$ to $1.5\times10^7$, $1.5\times10^6$ to $1\times10^7$, $1.5\times10^6$ to $9\times10^6$, $1.5\times10^6$ to $8\times10^6$, $1.5\times10^6$ to $7\times10^6$, $1.5\times10^6$ to $6\times10^6$, $1.5\times10^6$ to $5\times10^6$, $1.5\times10^6$ to $4\times10^6$, $1.5\times10^6$ to $3\times10^6$, $1.5\times10^6$ to $2\times10^6$, $2\times10^6$ to $1.5\times10^7$, $2\times10^6$ to $1\times10^7$, $2\times10^6$ to $9\times10^6$ $2\times06$ to $8\times10^6$, $2\times10^6$ to $7\times10^6$, $2\times10^6$ to $6\times10^6$ $2\times10^6$ to $5\times10^6$, $2\times10^6$ to $4\times10^6$, $2\times10^6$ to $3\times10^6$, $2.5\times10^6$ to $1.5\times10^7$, $2.5\times10^6$ to $1\times10^7$, $2.5\times10^6$ to $9\times10^6$, $2.5\times10^6$ to $8\times10^6$, $2.5\times10^6$ to $7\times10^6$, $2.5\times10^6$ to $6\times10^6$, $2.5\times10^6$ to $5\times10^6$, $2.5\times10^6$ to $4\times10^6$, or $2.5\times10^6$ to $3\times10^6$ $CD3^{'}V\alpha24J\alpha18^{'''}$ cells per kg of recipient body weight.

Tmems

A population of Tmems administered to a subject can be administered at a dose greater than at least about $1\times10^4$, $1\times10^5$, $5\times10^5$, $6\times10^5$, $7\times10^5$ $8\times10^5$, $9\times10^5$, $1\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2\times10^6$, $2.1\times10^6$, $2.2\times10^6$, $2.3\times10^6$, $2.4\times10^6$, $2.5\times10^6$, $2.6\times10^6$ $2.7\times10^6$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $43\times10^6$, $44\times10^6$, $4.5\times10^6$, $4.6\times10^6$, $4.7\times10^6$, $4.8\times10^6$, $4.9\times10^6$, $5\times10^6$, $5.1\times10^6$, $5.2\times10^6$, $5.3\times10^6$, $5.4\times10^6$, $5.5\times10^6$, $5.6\times10^6$, $5.7\times10^6$, $5.8\times10^6$, $5.9\times10^6$, $6\times10^6$, $6.5\times10^6$ $7\times10^6$, $7.5\times10^6$, $8\times10^6$, $8.5\times10^6$, $9\times10^6$, $9.5\times10^6$, $1\times10^7$, $1.5\times10^7$, $2\times10^7$, $2.5\times10^7$, $3\times10^7$, $3.5\times10^7$ $4\times10^7$, $4.5\times10$, $5\times10^7$, $5.5\times10^7$, $6\times10^7$ $6.5\times10$, $7\times10^7$, $7.5\times10^7$, $8\times10^7$, $8.5\times10^7$, $9\times10^7$, $9.5\times10^7$, $1\times10^8$, $1\times10^8$, $1.5\times10^8$, $2\times10^8$, $2.5\times10^8$, $3\times10^8$, $3.5\times10^7$, $4\times10^7$, $4.5\times10^7$, $5\times10^8$, $5.5\times10^7$, $6\times10^8$, $6.5\times10^8$, $7\times10^8$, $7.5\times10^7$, $8\times10^7$, $8.5\times10^8$, $9\times10^8$, $9.5\times10^8$, $1\times10^9$, or more cells per kg of recipient body weight.

A population of Tmems administered to a subject can be administered at a dose of at most about $1\times10^4$, $1\times10^5$, $5\times10^5$, $6\times10^5$, $7\times10^5$, $8\times10^5$, $9\times10^5$, $1\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$ $4.2\times10^6$, $4.3\times10^6$, $4.4\times10^6$, $4.5\times10^6$, $4.6\times10^6$, $4.7\times10^6$, $4.8\times10^6$, $4.9\times10^6$, $5\times10^6$, $5.1\times10^6$, $5.2\times10^6$, $5.3\times10^6$, $5.4\times10^6$, $5.5\times10^6$, $5.6\times10^6$, $5.7\times10^6$, $5.8\times10^6$, $5.9\times10^6$ $6\times10^6$, $6.5\times10^6$, $7\times10^6$, $7.5\times10^6$, $8\times10^6$, $8.5\times10^6$, $9\times10^6$, $9.5\times10^6$, $1\times10^7$, $1.5\times10^7$, $2\times10^7$, $2.5\times10^7$, $3\times10^7$, $3.5\times10^7$, $4\times10^7$, $4.5\times10^7$, $5\times10^7$, $5.5\times10^7$, $6\times10^7$, $6.5\times10^7$, $7\times10^7$, $7.5\times10^7$, $8\times10^7$, $8.5\times10^7$, $9\times10^7$, $9.5\times10^7$, $1\times10^8$, $1.5\times10^8$, $2\times10^8$, $2.5\times10^8$, $3\times10^8$, $3.5\times10^8$, $4\times10^7$, $4.5\times10^8$, $5\times10^8$, $5.5\times10^8$, $6\times10^8$, $6.5\times10^8$, $7\times10^8$, $7.5\times10^8$, $8\times10^8$, $8.5\times10^8$, $9\times10^8$, $9.5\times10^8$, $1\times10^9$, or less cells per kg of recipient body weight.

For example, a population of Tmems administered to a subject can be administered at a dose greater than at least about $1\times10^4$, $1\times10^5$, $5\times10^5$, $6\times10^5$, $7\times10^5$, $8\times10^5$, $9\times10^5$, $1\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$ $2\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$, $3\times10^6$, $3.1\times10^6$ $3.2\times10^6$ $3.3\times10^6$ $3.4\times10^6$, $3.5\times10^6$ $3.6\times10^6$ $3.7\times10^6$ $3.8\times10^6$, $3.9\times10^6$, $4\times10^6$, $4.1\times10^6$, $4.2\times10^6$, $4.3\times10^6$, $4.4\times10^6$, $4.5\times10^6$, $4.6\times10^6$, $4.7\times10^6$, $4.8\times10^6$ $4.9\times10^6$, $5\times10^6$, $5.1\times10^6$, $5.2\times10^6$ $5.3\times10^6$ $5.4\times10^6$, $5.5\times10^6$, $5.6\times10^6$, $5.7\times10^6$, $5.8\times10^6$, $5.9\times10^6$, $6\times10^6$, $6.5\times10^6$ $7\times10^6$, $7.5\times10^6$, $8\times10^6$, $8.5\times10^6$, $9\times10^6$ $9.5\times10^6$, $1\times10^7$ $1.5\times10^7$, $2\times10^7$, $2.5\times10^7$, $3\times10^7$, $3.5\times10^7$, $4\times10^7$, $4.5\times10^7$, $5\times10^7$, $5.5\times10^7$, $6\times10^7$, $6.5\times10^7$, $7\times10^7$, $7.5\times10^7$, $8\times10^7$, $8.5\times10^7$, $9\times10^7$, $9.5\times10^7$, $1\times10^8$, $1\times10^8$, $1.5\times10^8$, $2\times10^8$, $2.5\times10^7$, $3\times10^7$, $3.5\times10^7$, $4\times10^7$, $4.5\times10^8$, $5\times10^8$, $5.5\times10^8$, $6\times10^8$, $6.5\times10^8$, $7\times10^8$, $7.5\times10^8$, $8\times10^8$, $8.5\times10^8$, $9\times10^8$, $9.5\times10^8$, $1\times10^4$, or more $CD3^+CD45RA^-CD45RO^+$ cells per kg of recipient body weight.

In some embodiments, a population of Tmems administered to a subject can be administered at a dose of at most about $1\times10^4$, $1\times10^5$, $5\times10^5$, $6\times10^5$, $7\times10^5$, $8\times10^5$, $9\times10^5$, $1\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$ $0.9\times10^6$, $2\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$, $3\times10^6$ $3.1\times10^6$, $3.2\times10^6$, $3.3\times10^6$, $3.4\times10^6$, $3.5\times10^6$, $3.6\times10^6$, $3.7\times10^6$ $3.8\times10^6$, $3.9\times10^6$, $4\times10^6$, $4.1\times10^6$, $4.2\times10^6$, $4.3\times10^6$, $4.4\times10^6$, $4.5\times10^6$, $4.6\times10^6$, $4.7\times10^6$, $4.8\times10^6$, $4.9\times10^6$, $5\times10^6$, $5.1\times10^6$, $5.2\times10^6$, $5.3\times10^6$, $5.4\times10^6$, $5.5\times10^6$, $5.6\times10^6$, $5.7\times10^6$, $5.8\times10^6$, $5.9\times10^6$, $6\times10^6$, $6.5\times10^6$, $7\times10^6$, $7.5\times10^6$, $8\times10^6$, $8.5\times10^6$, $9\times10^6$, $9.5\times10^6$, $1\times10^7$, $1.5\times10^7$, $2\times10^7$, $2.5\times10^7$, $3\times10^7$, $3.5\times10^7$, $4\times10^7$, $4.5\times10^7$, $5\times10^7$, $5.5\times10^7$, $6\times10^7$, $6.5\times10^7$, $7\times10^7$, $7.5\times10^7$, $8\times10^7$, $8.5\times10^7$, $9\times10^7$, $9.5\times10$, $1\times10^7$, $0.1\times10^7$, $1.5\times10^8$, $2\times10^8$, $2.5\times10^8$, $3\times10^8$, $3.5\times10^8$, $4\times10^7$, $4.5\times10^8$, $5\times10^8$, $5.5\times10^8$, $6\times10^8$, $6.5\times10^8$, $7\times10^8$, $7.5\times10^8$, $8\times10^8$, $8.5\times10^8$, $9\times10^8$, $9.5\times10^8$, $1\times10^9$, or less $CD3^+CD45RA^-CD45RO^+$ cells per kg of recipient body weight.

In some embodiments, a population of Tmems administered to a subject can be administered at a dose of $1\times10^4$ to $1\times10^9$, $1\times10^5$ to $1\times10^8$, $1\times10^5$ to $2\times10^7$, $5\times10^5$ to $2\times10^7$, $5\times10^5$ to $1.5\times10^7$, $5\times10^5$ to $1\times10^7$, $5\times10^5$ to $9\times10^6$, $5\times10^5$ to $8\times10^6$, $5\times10^5$ to $7\times10^6$, $5\times10^5$ to $6\times10^6$, $5\times10^5$ to $5\times10^6$, $5\times10^5$ to $4\times10^6$, $5\times10^5$ to $3\times10^6$, $5\times10^5$ to $2\times10^6$, $5\times10^5$ to $1\times10^6$, $1\times10^6$ to $1.5\times10^7$, $1\times10^6$ to $1\times10^7$, $1\times10^6$ to $9\times10^6$, $1\times10^6$ to $8\times10^6$, $1\times10^6$ to $7\times10^6$, $1\times10^6$ to $6\times10^6$, $1\times10^6$ to $5\times10^6$, $1\times10^6$ to $4\times10^6$, $1\times10^6$ to $3\times10^6$, $1\times10^6$ to $2\times10^6$, $1.5\times10^6$ to $1.5\times10^7$, $1.5\times10^6$ to $1\times10^7$, $1.5\times10^6$ to $9\times10^6$, $1.5\times10^6$ to $8\times10^6$, $1.5\times10^6$ to $7\times10^6$, $1.5\times10^6$ to $6\times10^6$, $1.5\times10^6$ to $5\times10^6$, $1.5\times10^6$ to $4\times10^6$, $1.5\times10^6$ to $3\times10^6$, $1.5\times10^6$ to $2\times10^6$, $2\times10^6$ to $1.5\times10^7$, $2\times10^6$ to $1\times10^7$, $2\times10^6$ to $9\times10^6$, $2\times10^6$ to $8\times10^6$, $2\times10^6$ to $7\times10^6$, $2\times10^6$ to $6\times10^6$, $2\times10^6$ to $5\times10^6$, $2\times10^6$ to $4\times10^6$, $2\times10^6$ to $3\times10^6$, $2.5\times10^6$ to $1.5\times10^7$, $2.5\times10^6$ to $1\times10^7$, $2.5\times10^6$ to $9\times10^6$, $2.5\times10^6$ to $8\times10^6$, $2.5\times10^6$ to $7\times10^6$, $2.5\times10^6$ to $6\times10^6$, $2.5\times10^6$ to $5\times10^6$, $2.5\times10^6$ to $4\times10^6$, or $2.5\times10^6$ to $3\times10^6$ cells per kg of recipient body weight.

A population of Tmems administered to a subject can be administered at a dose of, for example, $1\times10^4$ to $1\times10^9$, $1\times10^5$ to $1\times10^8$, $1\times10^5$ to $2\times10^7$, $5\times10^5$ to $2\times10^7$, $5\times10^5$ to $1.5\times10^7$, $5\times10^5$ to $1\times10^7$, $5\times10^5$ to $9\times10^6$, $5\times10^5$ to $8\times10^6$, $5 \times 10^5$ to $7 \times 10^6$, $5 \times 10^5$ to $6 \times 10^6$, $5 \times 10^5$ to $5 \times 10^6$, $5 \times 10^5$ to $4 \times 10^6$, $5 \times 10^5$ to $3 \times 10^6$, $5 \times 10^5$ to $2 \times 10^6$, $5 \times 10^5$ to $1 \times 10^6$, $1 \times 10^6$ to $1.5 \times 10^7$ $1 \times 10^6$ to $1 \times 10$, $1 \times 10^6$ to $9 \times 10^6$, $1.5 \times 10^6$ to $8 \times 10^6$, $1 \times 10^6$ to $7 \times 10^6$, $1 \times 10^6$ to $6 \times 10^6$, $1 \times 10^6$ to $5 \times 10^6$, $1 \times 10^6$ to $4 \times 10^6$, $1 \times 10^6$ to $3 \times 10^6$, $1 \times 10^6$ to $2 \times 10^6$, $1.5 \times 10^6$ to $1.5 \times 10^7$, $1.5 \times 10^6$ to $1 \times 10^7$, $1.5 \times 10^6$ to $9 \times 10^6$, $1.5 \times 10^6$ to $8 \times 10^6$, $1.5 \times 10^6$ to $7 \times 10^6$, $1.5 \times 10^6$ to $6 \times 10^6$, $1.5 \times 10^6$ to $5 \times 10^6$, $1.5 \times 10^6$ to $4 \times 10^6$, $1.5 \times 10^6$ to $3 \times 10^6$, $1.5 \times 10^6$ to $2 \times 10^6$, $2 \times 10^6$ to $1.5 \times 10^7$, $2 \times 10^6$ to $1 \times 10^7$, $2 \times 10^6$ to $9 \times 10^6$, $2 \times 10^6$ to $8 \times 10^6$, $2 \times 10^6$ to $7 \times 10^6$, $2 \times 10^6$ to $6 \times 10^6$, $2 \times 10^6$ to $5 \times 10^6$, $2 \times 10^6$ to $4 \times 10^6$, $2 \times 10^6$ to $3 \times 10^6$, $2.5 \times 10^6$ to $1.5 \times 10^7$, $2.5 \times 10^6$ to $1 \times 10^7$, $2.5 \times 10^6$ to $9 \times 10^6$, $2.5 \times 10^6$ to $8 \times 10^6$, $2.5 \times 10^6$ to $7 \times 10^6$, $2.5 \times 10^6$ to $6 \times 10^6$, $2.5 \times 10^6$ to $5 \times 10^6$, $2.5 \times 10^6$ to $4 \times 10^6$, or $2.5 \times 10^6$ to $3 \times 10^6$ $CD3^-CD45RA^-CD45RO^+$ cells per kg of recipient body weight.

Treg to Tcon Ratio

In the methods of the disclosure, the ratio of Tcons:Tregs administered to a subject can be, for example, about 1:100, 1:50, 1:25, 1:20, 1:15, 1:10, 1:9, 1:8, 1:7, 1:6, 1:5, 1:4, 1:3, 1:2.5, 1:2, 1.5:2, 1:1.5, 1:1, 1.5:1, 2:1, 2:1.5, 2.5:1, 3:1, 4:1, 5:1, 6:1, 7:1, 8:1, 9:1, 10:1, 15:1, 20:1, 25:1, 50:1, or 100:1.

Conditioning Regimens, GVHD Prophylactics, and Additional Agents.

In some embodiments of the methods of the disclosure, a subject can be treated with myeloablative conditioning prior to infusion of cell populations described herein.

In some embodiments, the methods of the disclosure can comprise administration of one or more immunosuppressants or other agents to a subject.

An immunosuppressant agent can be administered to a subject, for example, to prevent rejection of the graft by the recipient immune system, or to prevent or reduce GVHD resulting from the graft attacking recipient cells. hnmunosuppressive agents include, for example, calcineurin inhibitors, which combine with binding proteins to inhibit calcineurin activity, and monoclonal antibodies.

Calcineurin inhibitors include, for example, tacrolimus, cyclosporine A, etc. Adjuvant agents can be combined with calcineurin inhibitors and include, for example, steroids, azathioprine, mycophenolate mofetil, and sirolimus. Monoclonal antibodies useful as immunosuppressive agents include, for example, antagonist antibodies, (e.g., antibodies that antagonize IL-2R such as basiliximab and daclizumab), and antibodies that deplete an immune cell population by antibody dependent cellular cytotoxicity (e.g., anti-CD3 antibodies for T cell depletion such as muromonab-CD3)

A method of the disclosure further can further comprise administering to a subject in need thereof an anti-tumor agent, or a pharmaceutically-acceptable salt or prodrug thereof. Examples of anti-tumor agents include but are not limited to antitumor alkylating agents, antitumor antimetabolites, antitumor antibiotics, plant-derived antitumor agents, antitumor organoplatinum compounds, antitumor campthotecin derivatives, antitumor tyrosine kinase inhibitors, monoclonal antibodies, interferons, biological response modifiers, and other agents having antitumor activities, or pharmaceutically acceptable salts thereof.

Exemplary Embodiments

Disclosed herein, in some embodiments, is a method of treating a human subject in need thereof, comprising administering to said human subject: a) a population of hematopoietic stem and progenitor cells (HSPCs), wherein said population of HSPCs comprises more than $1 \times 10^5$ HSPCs (preferably $5 \times 10^5$ to $2 \times 10^7$ HSPCs) per kilogram of body weight of said human subject, wherein said HPSCs are $CD34^+$; b) a population of cells comprising regulatory T cells (Tregs); wherein said Tregs are $CD4^+CD25^+CD127^{dim}$ or $CD4^+FOXP3^+$, wherein said population of cells comprising Tregs comprises more than $1 \times 10^5$ Tregs (preferably $5 \times 10^5$ to $4 \times 10^6$ Tregs) per kilogram of body weight of said human subject, wherein said population of cells comprising Tregs has not been cryopreserved prior to said administering of said population of cells comprising Tregs; and c) a population of conventional T cells (Tcons), wherein said Tcons are CD3+, wherein said population of Tcons comprises fewer than $1 \times 10^7$ Tcons (preferably $5 \times 10^5$ to $4 \times 10^6$ Tcons) per kilogram of body weight of said human subject; wherein said population of HSPCs and said population of cells comprising Tregs are administered prior to (preferably 36-60 hours prior to) said population of Tcons.

Disclosed herein, in some embodiments, is a method of treating a human subject in need thereof, comprising administering to said human subject: a) a population of hematopoietic stem and progenitor cells (HSPCs), wherein said population of HSPCs comprises more than $1 \times 10^5$ HSPCs (preferably $5 \times 10^5$ to $2 \times 10^7$ HSPCs) per kilogram of body weight of said human subject, wherein said HPSCs are $CD34^+$; b) a population of cells comprising regulatory T cells (Tregs); wherein said Tregs are $CD4^+CD25^+CD127^{dim}$ or $CD4^+FOXP3^+$, wherein said population of cells comprising Tregs comprises more than $1 \times 10^5$ Tregs (preferably $5 \times 10^5$ to $4 \times 10^6$ Tregs) per kilogram of body weight of said human subject, wherein said population of cells comprising Tregs has not been cryopreserved prior to said administering of said population of cells comprising Tregs; c) a population of conventional T cells (Tcons), wherein said Tcons are CD3+, wherein said population of Tcons comprises fewer than $1 \times 10^7$ Tcons (preferably $5 \times 10^5$ to $4 \times 10^6$ Tcons) per kilogram of body weight of said human subject; and d) a graft versus host disease (GVHD) prophylactic agent (preferably tacrolimus or sirolimus); wherein said population of HSPCs and said population of cells comprising Tregs are administered prior to (preferably 36-60 hours prior to) said population of Tcons, and wherein said human subject does not develop graft versus host disease (GVHD) within 30 days (preferably within 1 year) after said administering of said population of Tcons.

Disclosed herein, in some embodiments, is a method of treating a human subject in need thereof, comprising administering to said human subject: a) a population of hematopoietic stem and progenitor cells (HSPCs), wherein said population of HSPCs comprises more than $1 \times 10^5$ HSPCs (preferably $5 \times 10^5$ to $2 \times 10^7$ HSPCs) per kilogram of body weight of said human subject, wherein said HPSCs are $CD34^+$; b) a population of cells comprising regulatory T cells (Tregs); wherein said Tregs are $CD4^+CD25^+CD127^{dim}$ or $CD4^+FOXP3^+$, wherein said population of cells comprising Tregs comprises more than $1 \times 10^5$ Tregs (preferably $5 \times 10^5$ to $4 \times 10^6$ Tregs) per kilogram of body weight of said human subject, wherein said population of cells comprising Tregs comprises $CD45^+$ cells, wherein more than 50% (preferably more than 90%) of said $CD45^+$ cells are Tregs, wherein said population of cells comprising Tregs has not been cryopreserved prior to said administering of said population of cells comprising Tregs; and c) a population of conventional T cells (Tcons), wherein said Tcons are CD3+, wherein said population of Tcons comprises fewer than $1 \times 10^7$ Tcons (preferably $5 \times 10^5$ to $4 \times 10^6$ Tcons) per kilogram of body weight of said human subject, wherein said population of Tcons has been cryopreserved prior to said administering of said population Tcons; wherein said population of HSPCs and said population of cells comprising Tregs are administered prior to (preferably 36-60 hours prior to) said population of Tcons.

Disclosed herein, in some embodiments, is a method of treating a human subject in need thereof, comprising administering to said human subject: a) a population of hematopoietic stem and progenitor cells (HSPCs), wherein said population of HSPCs comprises more than $1\times10^5$ HSPCs (preferably $5\times10^5$ to $2\times10^7$ HSPCs) per kilogram of body weight of said human subject, wherein said IPSCs are CD34$^+$; b) a population of cells comprising regulatory T cells (Tregs); wherein said Tregs are CD4$^+$CD25$^+$CD127$^{dim}$ or CD4$^+$FOXP3$^+$, wherein said population of cells comprising Tregs comprises more than $1\times10^5$ Tregs (preferably $5\times10^5$ to $4\times10^6$ Tregs) per kilogram of body weight of said human subject, wherein said population of cells comprising Tregs has not been cryopreserved prior to said administering of said population of cells comprising Tregs; c) a population of conventional T cells (Tcons), wherein said Tcons are CD3+, wherein said population of Tcons comprises fewer than $1\times10^7$ Tcons (preferably $5\times10^5$ to $4\times10^6$ Tcons) per kilogram of body weight of said human subject, wherein said population of Tcons has been cryopreserved prior to said administering of said population Tcons; and d) a graft versus host disease (GVTD) prophylactic agent (preferably tacrolimus or sirolimus); wherein said population of HSPCs and said population of cells comprising Tregs are administered prior to (preferably 36-60 hours prior to) said population of Tcons, and wherein said human subject does not develop graft versus host disease (GVHD) within 30 days (preferably within 1 year) after said administering of said population of Tcons.

Disclosed herein, in some embodiments, is a method of treating a human subject in need thereof, comprising administering to said human subject: a) a population of hematopoietic stem and progenitor cells (HSPCs), wherein said population of HSPCs comprises more than $1\times10^5$ HSPCs (preferably $5\times10^5$ to $2\times10^7$ HSPCs) per kilogram of body weight of said human subject, wherein said HPSCs are CD34$^+$; b) a population of cells comprising regulatory T cells (Tregs); wherein said Tregs are CD4$^+$CD25$^+$CD127$^{dim}$ or CD4$^+$FOXP3$^+$, wherein said population of cells comprising Tregs comprises more than $1\times10^5$ Tregs (preferably $5\times10^5$ to $4\times10^6$ Tregs) per kilogram of body weight of said human subject, wherein said population of cells comprising Tregs comprises CD45$^+$ cells, wherein more than 50% (preferably more than 90%) of said CD45$^+$ cells are Tregs, wherein said population of cells comprising Tregs has not been cryopreserved prior to said administering of said population of cells comprising Tregs; c) a population of conventional T cells (Tcons), wherein said Tcons are CD3+, wherein said population of Tcons comprises fewer than $1\times10^7$ Tcons (preferably $5\times10^5$ to $4\times10^6$ Tcons) per kilogram of body weight of said human subject, d) a graft versus host disease (GVHD) prophylactic agent (preferably tacrolimus or sirolimus); wherein said population of HSPCs and said population of cells comprising Tregs are administered prior to (preferably 36-60 hours prior to) said population of Tcons, and wherein said human subject does not develop graft versus host disease (GVHD) within 30 days (preferably within 1 year) after said administering of said population of Tcons.

Disclosed herein, in some embodiments, is a method of treating a human subject in need thereof, comprising administering to said human subject: a) a population of hematopoietic stem and progenitor cells (HSPCs), wherein said population of HSPCs comprises more than $1\times10^5$ HSPCs (preferably $5\times10^5$ to $2\times10^7$ HSPCs) per kilogram of body weight of said human subject, wherein said IPSCs are CD34$^+$; b) a population of cells comprising regulatory T cells (Tregs); wherein said Tregs are CD4$^+$CD25$^+$CD127$^{dim}$ or CD4$^+$FOXP3$^+$, wherein said population of cells comprising Tregs comprises more than $1\times10^5$ Tregs (preferably $5\times10^5$ to $4\times10^6$ Tregs) per kilogram of body weight of said human subject, wherein said population of cells comprising Tregs comprises CD45$^+$ cells, wherein more than 50% (preferably more than 90%) of said CD45$^+$ cells are Tregs, wherein said population of cells comprising Tregs has not been cryopreserved prior to said administering of said population of cells comprising Tregs; and c) a population of conventional T cells (Tcons), wherein said Tcons are CD3+, wherein said population of Tcons comprises fewer than $1\times10^7$ Tcons (preferably $5\times10^5$ to $4\times10^6$ Tcons) per kilogram of body weight of said human subject, wherein said population of Tcons has been cryopreserved prior to said administering of said population Tcons; wherein said population of HSPCs and said population of cells comprising Tregs are administered prior to (preferably 36-60 hours prior to) said population of Tcons, and wherein said human subject does not develop graft versus host disease (GVHD) within 30 days (preferably within 1 year) after said administering of said population of Tcons.

Disclosed herein, in some embodiments, is a method of treating a human subject in need thereof, comprising administering to said human subject: a) a population of hematopoietic stem and progenitor cells (HSPCs), wherein said population of HSPCs comprises more than $1\times10^5$ HSPCs (preferably $5\times10^5$ to $2\times10^7$ HSPCs) per kilogram of body weight of said human subject, wherein said HPSCs are CD34$^+$; b) a population of cells comprising regulatory T cells (Tregs); wherein said Tregs are CD4$^+$CD25$^+$CD127$^{dim}$ or CD4$^+$FOXP3$^+$, wherein said population of cells comprising Tregs comprises more than $1\times10^5$ Tregs (preferably $5\times10^5$ to $4\times10^6$ Tregs) per kilogram of body weight of said human subject, wherein said population of cells comprising Tregs comprises CD45$^+$ cells, wherein more than 50% (preferably more than 90%) of said CD45$^+$ cells are Tregs, wherein said population of cells comprising Tregs has not been cryopreserved prior to said administering of said population of cells comprising Tregs; c) a population of conventional T cells (Tcons), wherein said Tcons are CD3+, wherein said population of Tcons comprises fewer than $1\times10^7$ Tcons (preferably $5\times10^5$ to $4\times10^6$ Tcons) per kilogram of body weight of said human subject, wherein said population of Tcons has been cryopreserved prior to said administering of said population Tcons; and d) a graft versus host disease (GVHD) prophylactic agent (preferably tacrolimus or sirolimus); wherein said population of HSPCs and said population of cells comprising Tregs are administered prior to (preferably 36-60 hours prior to) said population of Tcons.

Disclosed herein, in some embodiments, is a method of treating a human subject in need thereof, comprising administering to said human subject: a) a population of hematopoietic stem and progenitor cells (HSPCs), wherein said population of HSPCs comprises more than $1\times10^5$ HSPCs (preferably $5\times10^5$ to $2\times10^7$ HSPCs) per kilogram of body weight of said human subject, wherein said HPSCs are CD34$^+$; b) a population of cells comprising regulatory T cells (Tregs); wherein said Tregs are CD4$^+$CD25$^+$CD127$^{dim}$ or CD4$^+$FOXP3$^+$, wherein said population of cells comprising Tregs comprises more than $1\times10^5$ Tregs (preferably $5\times10^5$ to $4\times10^6$ Tregs) per kilogram of body weight of said human subject, wherein said population of cells comprising Tregs comprises CD45$^+$ cells, wherein more than 50% (preferably more than 90%) of said CD45$^+$ cells are Tregs, wherein said population of cells comprising Tregs has not been cryopreserved prior to said administering of said population of cells comprising Tregs; c) a population of conventional T cells (Tcons), wherein said Tcons are CD3+, wherein said population of Tcons comprises fewer than 1×10$^7$ Tcons (preferably 5×10$^5$ to 4×10$^6$ Tcons) per kilogram of body weight of said human subject, wherein said population of Tcons has been cryopreserved prior to said administering of said population Tcons; and d) a graft versus host disease (GVHD) prophylactic agent (preferably tacrolimus or sirolimus); wherein said population of HSPCs and said population of cells comprising Tregs are administered prior to (preferably 36-60 hours prior to) said population of Tcons, and wherein said human subject does not develop graft versus host disease (GVHD) within 30 days (preferably within 1 year) after said administering of said population of Tcons.

EXAMPLES

Example 1: Clinical Trial Comprising Administering HSPC and Treg Prior to Tcon

This example illustrates the utility of method disclosed herein to treat subjects with cancer, including achieving immune reconstitution and GVT in the absence of GVHD.

This study included twelve patients with high risk malignancies who had HLA matched sibling donors. The study was approved by the Stanford Institutional Review Board (NCT01660607) and FDA IND 14686. Written informed consent was obtained for all patients and donors consistent with the Declaration of Helsinki.

Study Design

Patient characteristics are provided in FIG. 1; abbreviations are as follows: TBI, total body irradiation; Cy, Cytoxan; VP-16, etoposide; Bu, busulfan; AML, acute myeloid leukemia; CR, complete remission; MDS, myelodysplastic syndrome; RAEB2, refractory anemia of excess blasts 2; NHL, non-Hodgkins lymphoma; ETP-ALL, early T cell precursor acute lymphoplastic leukemia; MRD, minimal residual disease; CML, chronic myeloid leukemia; MF, myelofibrosis After myeloablative conditioning, subjects were administered a population of HSPCs and a population of Tregs on day 0, followed by a population of Tcons on day 2. The primary objectives of the study were to determine the efficacy, safety and feasibility of this approach, to determine the maximum tolerated dose of infused Treg and Tcon, and to determine 1 year EFS post-HCT. Safety was assessed as any grade 2 or greater serious adverse event attributed to treatment, and specific dose limiting toxicity was defined as: Acute GVHD>grade 2, Grade 4 neutropenia lasting to 28 days after HCT, and Grade 3 to 5 cytokine/release syndrome/acute infusion reactions.

Inclusion criteria for enrollment were: Acute leukemia (primary refractory, CR1 with minimal residual disease (MRD) positive or high-risk features, beyond CR1), chronic myelogenous leukemia (accelerated or blast phase), myelodysplastic syndromes (Int-2 or high risk), myeloproliferative disorders, non-Hodgkin lymphoma with poor risk features not suitable for autologous HCT, age≤60 years, availability of an HLA matched related donor and no prior myeloablative therapy or HCT.

Figure 2B:
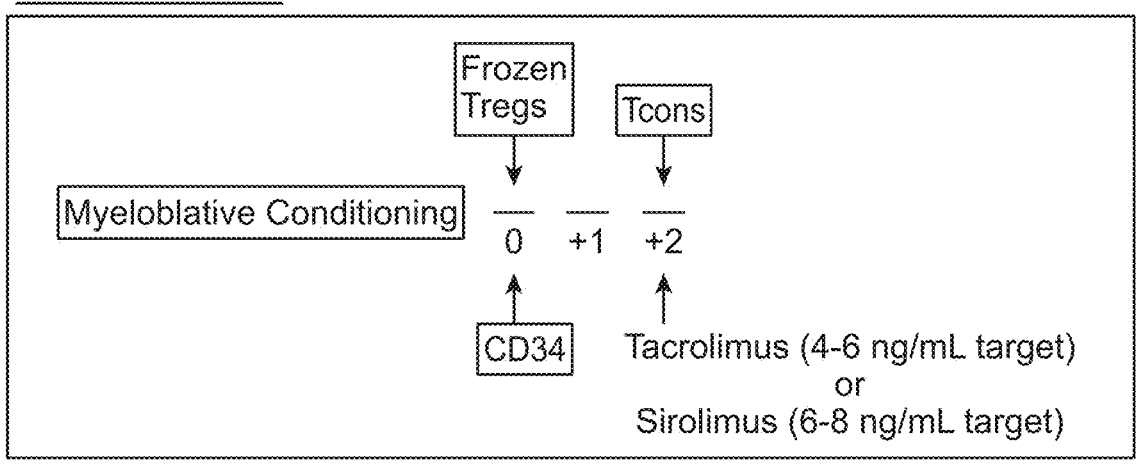

The original clinical protocol schema is shown in FIG. 2A. Treg were administered with the HSPC donor graft, two days prior to Tcon administration. After accrual of the first cohort of five patients on the original protocol, GVHD was noted. The protocol was amended to utilize fresh rather than frozen Treg cells and to introduce targeted-dose single-agent tacrolimus (4-6 ng/ml) or sirolimus (6-8 ng/ml) GVHD prophylaxis (FIG. 2B).

Conditioning Regimens and Supportive Care

The clinical protocol supported the use of different myeloblative conditioning regimens depending upon the disease characteristics of enrolled subjects. For acute leukemia, high risk CML, myelodysplastic syndrome, and myeloproliferative disorders, conditioning included fractionated total body irradiation: fTBI (1320 cGy, fractionated over four days), VP16 (60 mg/kg, as a single infusion) and cyclophosphamide (60 mg/kg, as a single infusion); or busulfan (3.6 mg/kg q24 initially, infused over 4 days, with targeting to busulfan level of 800-900 nM) and cyclophosphamide (60 mg/kg, per infusion over two infusions). For non-Hodgkin lymphoma, conditioning consisted of carmustine (300 mg/m2), VP16 (60 mg/kg) and cyclophosphamide (100 mg/kg).

Subjects on the original protocol received no GVHD prophylaxis, however after protocol modification subjects could receive either tacrolimus or sirolimus, based upon pre-clinical evidence that sirolimus facilitates Treg function. Following one case of sinusoidal obstruction syndrome (SOS) in a subject with BU/Cy conditioning, sirolimus GVHD prophylaxis was restricted to only subjects with TBI-based conditioning.

Infectious disease prophylaxis consisted of acyclovir 400 mg TID PO (for 1 year), single strength Bactrim (day 30-60) and ciprofloxacin 500 mg PO BID (day −2 until engraftment). Viral surveillance via quantitative PCR was performed for EBV (every 2 weeks) and CMV (weekly) starting at Day +14 until Day +100.

Graft Engineering

Donor cells were obtained from volunteer donors by apheresis at Stanford Health Care after 5 daily doses of 10 mcg/kg rhG-CSF (Neupogen, Amgen, Thousand Oaks, Calif.) using a continuous-flow cell separator (SPECTRA; Cobe BCT). Two consecutive apheresis collections were performed on days 4 and 5 and the cell products were combined. CD34+ cells were collected using either the isolex 300i (Baxter healthcare, Deerfield, Ill.) or the CliniMACS Cell Selection System (Miltenyi Biotec, Bergish Gladbach, Germany). The CD34 reduced (flow-through) fractions were retained and used for isolation of donor Treg. For cell selection, clinical grade reagents were used under Good Manufacturing Practice Conditions within the BMT Cellular Therapy Facility.

Figure 3:
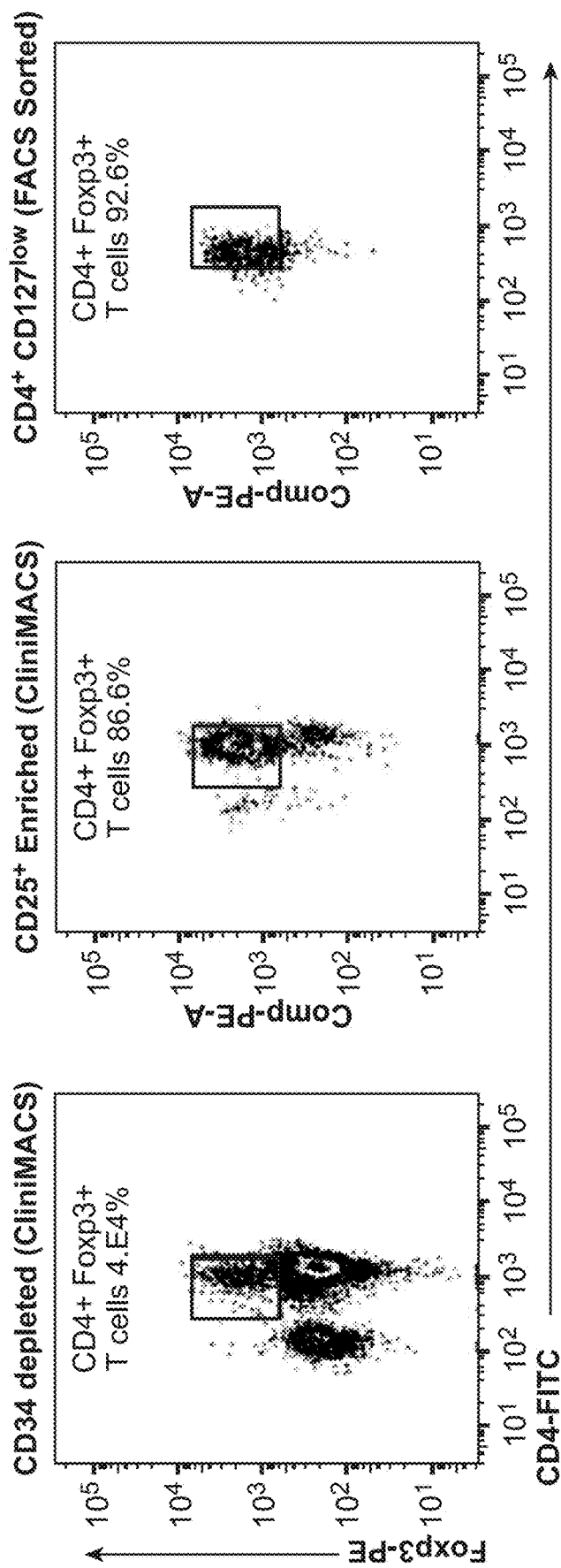
FIG. 3 illustrates enrichment of Treg cells from a peripheral blood apheresis product for administration to a subject.
Figure 4A:
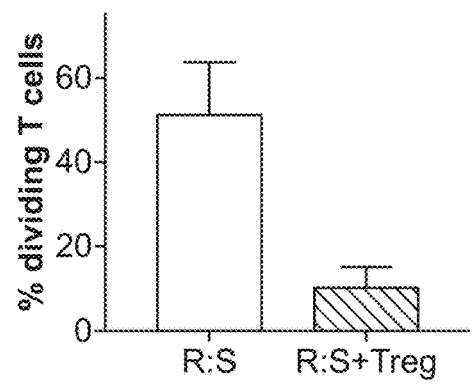
FIG. 4 illustrates the suppressive capacity of populations of cells comprising Tregs in mixed lymphocyte reactions (MLRs).
Figure 4B:
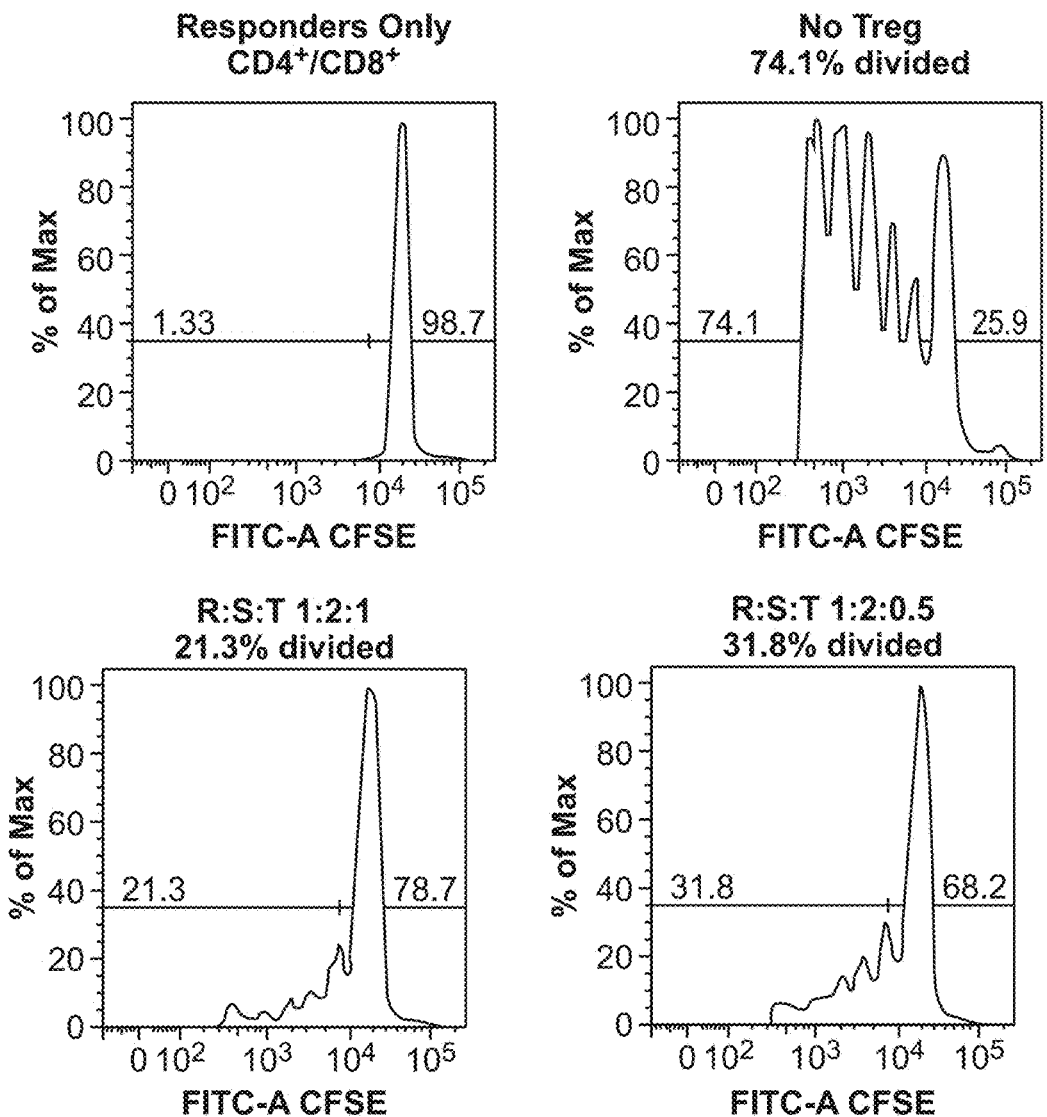

CD25+ cells were then selected from the CD34-depleted fraction using bead purification (Miltenyi). Tcon were obtained from the negative fraction and the positive fraction was used for Treg purification. CD4+CD25+CD127dim cells underwent further selection by FACS using a BD Influx cell sorter (BD Biosciences, San Jose Calif.). A representative analysis of cells collected after CD34+ selection, CD25+ cell selection and CD4+CD127+cell sorting analyzed for CD4 and FoxP3 expression is shown in FIG. 3. Enrichment of Tregs is shown following depletion of CD34+ cells by immunomagnetic selection (left panel), selection of CD25+ by immunomagnetic selection (middle panel) and purification by FACS sorting of CD4+CD127lowCD25+ cells (right panel). Representative plots are provided from one patient. As can be seen, high purity of Tregs were obtained. These cells were highly suppressive in a mixed lymphocyte reaction (MLR). FIG. 4A illustrates the percentage of CFSE$^{dim}$ populations of T cells cultured HLA-mismatched PBMC with/without Treg (1:1 ratio) in allo-MLR, analyzed by FACS. For the MLR, enriched CD4+ and CD8+ cells (2×10⁵, MACS beads Miltenyi Biotech) from the donor peripheral blood or apheresis were set in triplicates in 96 well flat-bottom plates as Responders. Responders were labeled with CellTrace CFSE, according to the manufacturer's instructions at day 0 (Invitrogen, molecular probes), or pulsed with 1 µCi/well [³H, thymidine Perkin-Elmer] for the last 16 hours of the 5 day assay. Stimulators were a combination of 9 different buffy coats from healthy donors and were irradiated with cesium irradiator (¹⁵⁷Cs) at 33 Gy and were set in Responders to Stimulators (R:S) in 1:0, 1:1, 1:2 and 1:4 ratios. Treg were added as suppressors in Responders to Suppressors (R:SUP) ratios of 1:1, 1:0.5, 1:0.25 and 1:10. The media (cRPMI) was supplemented with OKT3 (Miltenyi Biotech). Results were read at day 5 by flow cytometry (LSRII BD) or Beta counter reader (Tomtec, Wallac). Further results are presented in FIG. 4-C.

For clinical sorting, the antibodies were re-purified over Protein A (or G) columns, held at low pH for 30 minutes. Antibodies were conjugated with FITC and Alexafluor 647, sterile filtered and stored in single use aliquots.

Dose Escalation and Graft Properties

After myeloablative conditioning, subjects were administered a population of HSPCs and a population of Tregs on day 0, followed by a population of Tcons on day 2.

Figure 5:
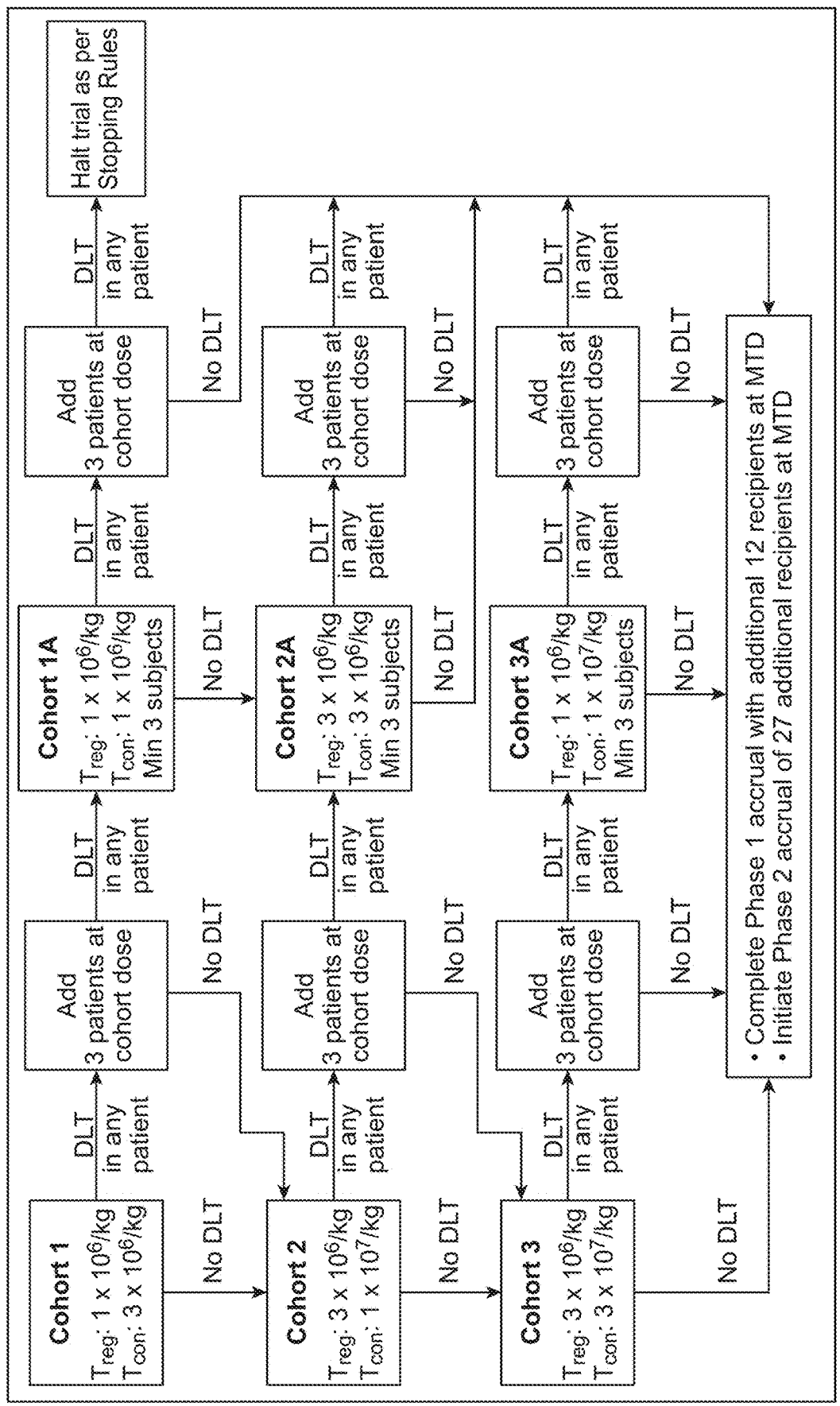
FIG. 5 illustrates the dose escalation scheme of a clinical trial comprising administering HSPCs and Tregs prior to Tcons.

The study involved a dose escalation scheme as illustrated in FIG. 5. The Treg dose escalation was established as the ratio Treg:Tcon, with the initial dose cohort target dose of 1×10⁶ Treg/kg and 3×10⁶ CD3+ Tcon/kg in the first cohort of three patients. Since GVHD was observed in one patient, according to the predefined dose-escalation plan, the group underwent expansion to an additional three subjects at a Treg:Tcon ratio of 1:1, with 1×10⁶ Treg/kg and 1×10⁶ Tcon/kg. Since no dose limiting toxicity was observed in these additional subjects, the target dose was escalated to 3×10⁶ Treg/kg and 3×10⁶ CD3+ Tcon/kg. After no dose limiting toxicity was observed in three additional patients, the maximally tolerated target dose was established which was also the maximal technical dose of Treg that could be collected from two apheresis collections, and an additional three patients were accrued at this dose level. In a number of patients, achieving 3×10⁶ Treg/kg was not feasible and whatever cell dose achieved was administered.

Figure 6:
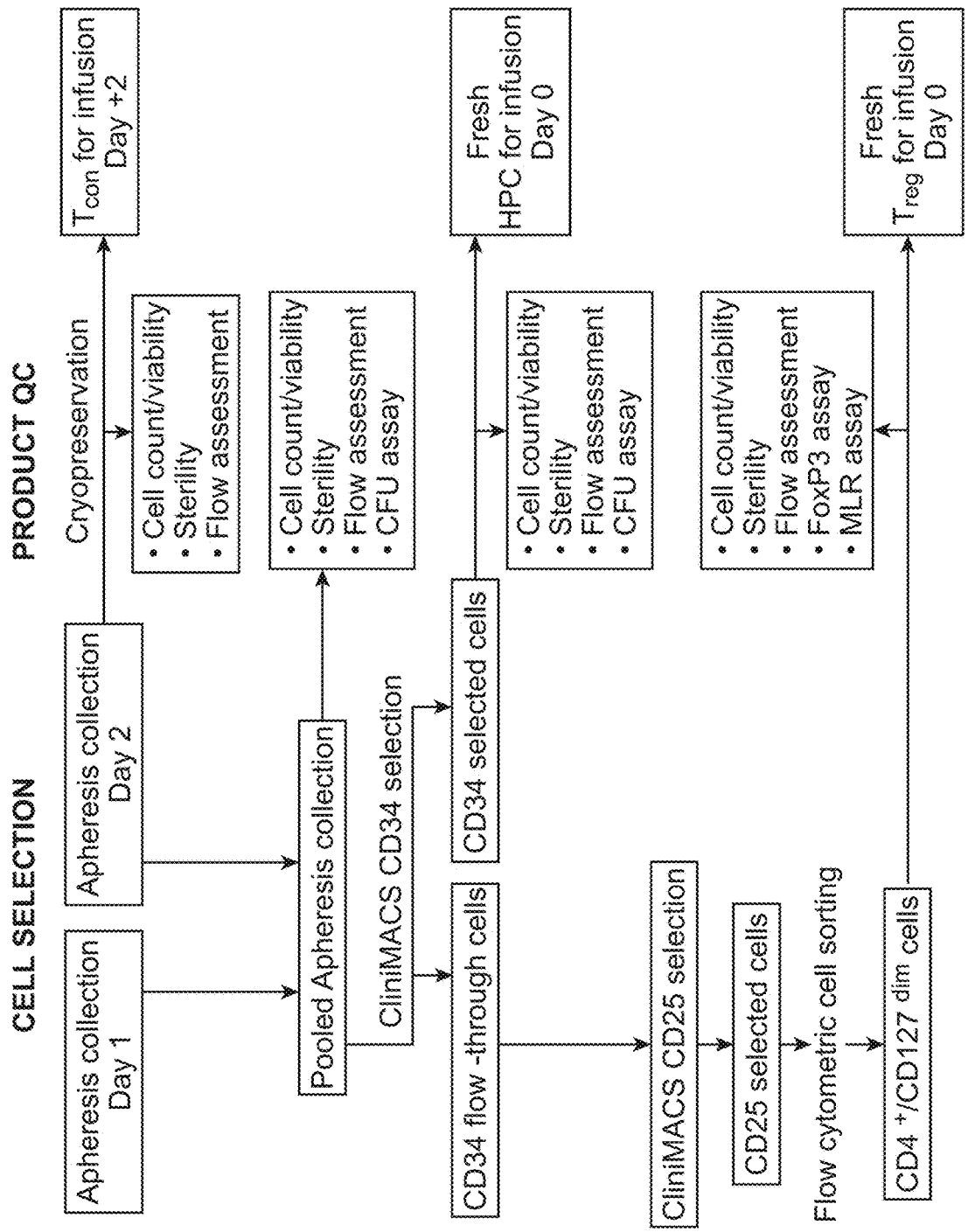
FIG. 6 provides a schematic of graft production and administration with fresh Tregs.

A schematic of graft production and administration for the modified protocol with fresh Tregs is provided in FIG. 6. All subjects at the 1.0×10⁶/kg Treg dose received this target dose of Treg, however not all subjects received a target dose of 3.0×10⁶ Treg/kg. FIG. 7 shows the cell dose yields of subjects, with a median of 2.5×10⁶ Treg/kg administered (range 2.4-3.0×10⁶ Treg/kg). Median Treg recovery was 67% (range 50.7-87.8%) and median Treg purity was 94% (91-96%), based on FOXP3+ expression by intracellular cytokine staining. All but one patient achieved a CD34+ dose >2.0×10⁶ cells/kg, with a median dose of 3.9×10⁶ cells/kg (range 1.2-15.9×10⁶). Dosing details are provided in FIG. 8.

Cell Infusion, Engraftment, and Clinical Outcomes

Clinical outcomes are summarized in FIG. 9. No infusion reactions were observed. All twelve subjects achieved primary full donor engraftment, however one subject receiving the lowest dose level (1×10⁶ Treg/kg and 1×10⁶ CD3+ Tcon/kg) with high-risk RAEB-2 MDS had secondary graft failure. Including this subject, neutrophils reached 1.0× 10⁹/L at a median of 11 days (10-16 days). Platelets reached 50×10⁹/L at a median of 16 days (9-25 days). Prior to protocol modification, three of five patients treated achieved a complete remission (2 of which remain in remission >1 year). Following protocol modification (to fresh Tregs with GVHD prophylaxis), five of seven patients achieved a complete remission (four of which remain in remission >1 year) and no GVHD was observed.

In an initial patient who received Treg:Tcon at a ratio of 1:3, acute GVHD grade III was observed. Therefore, the ratio was adjusted according to the protocol to 1:1 at a dose of 1×10⁶/kg for both Treg and Tcon. Of the first three subjects treated at this dose level, one case of acute GVHD was observed (grade III). An additional two patients were treated at this ratio. One additional patient developed acute grade I skin GVHD, which was steroid responsive.

The protocol was modified to use only fresh Treg and to include low dose single agent GVHD prophylaxis with sirolimus since this agent has been shown to be protective of Treg (FIG. 2). In clinical situations where the risk of sinusoidal obstruction syndrome may be increased with sirolimus, low dose tacrolimus was substituted. Following protocol modification, no additional cases of GVHD were observed in the subsequent seven patients, although one subject had a transaminitis and was treated for possible hepatic GVHD or medication intolerance, after medications were changed quick resolution of transaminitis was observed.

A total of eleven patients achieved survival >6 months and could be evaluated for chronic GVHD. At a median follow-up of 481 days (range 212-1887 days), two of the eleven subjects developed chronic GVHD, both of whom were in the initial protocol cohort. Both had prior grade III acute GVHD and chronic GVHD manifestations were skin-limited and steroid responsive. After protocol modification, no patients in the second cohort have developed chronic GVHD After protocol modification, one patient conditioned with busulfan and cyclophosphamide conditioning and who received sirolimus for GVHD prophylaxis had mild SOS, treated to resolution with defibrotide and supportive care. Eleven of twelve patients experienced mucositis (4 with grade 1, 3 with grade 2 and 4 with grade 3).

Immune Reconstitution

In order to evaluate the immune reconstitution of patients enrolled in this research study, a comparison standard-of-care control cohort was identified, consisting of five concurrent patients who received myeloablative HCT and who had no acute or chronic GVHD or relapse. Using flow cytometry, immune cell subsets were quantified from frozen and thawed PBMCs at standardized time points after HCT (FIG. 10).

PBMCs from BMT patients with or without pre-infusion of Treg were recovered from liquid nitrogen. PBMCs were washed with MACS buffer and stained with a pan-PBMC panel or $T_{reg}$ activation panel at 4° C. for 1 hr. After washing with MACS buffer, the stained cells were fixed with 4% formaldehyde at 4° C. overnight. Flow cytometric analysis was performed on an LSR II and data were analyzed by FlowJo software. Viability staining was performed using 0.5 µM Cisplatinum (Fluidigm Cat #201064), for 5 min at room temperature. Cell surface antibody master mix was prepared and filtered through 0.2 µm filters. Cells were resuspended in the master mix and incubated for 30 min. Cells were washed and incubated in the fixing solution prepared in accordance with manufacturer's recommendations (eBiosciences Cat #00-5523). The cells were fixed for 1 hr at room temperature, washed and then incubated with intracellular antibody mixture in permeabilization buffer (eBiosciences Cat #00-5523) for 1 hr.

Figure 10:
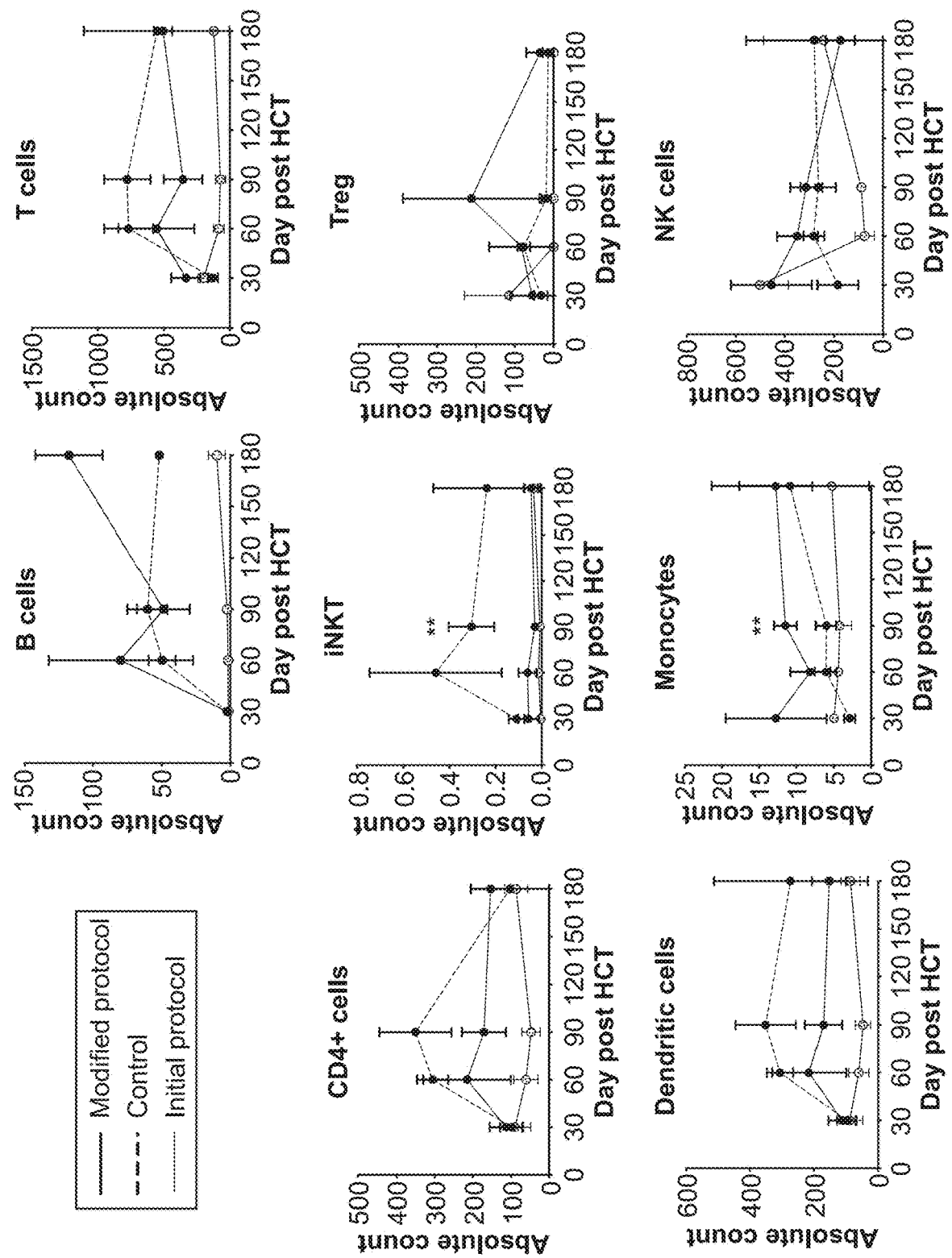
FIG. 10 illustrates immune cell reconstitution at standardized time points after HCT.

Patients in the initial cohort showed relatively poor T, B, NK and Treg reconstitution compared to patients treated under the modified protocol or standard of care (FIG. 10). Patients treated on the modified protocol with fresh Treg appeared to have generally comparable immune reconstitution in T, B, NK, DC, and monocyte populations as compared to standard of care controls. The absolute number of iNKT cells was significantly lower in the first six months in both the initial and modified patient cohorts when compared to controls (two-tailed student T test, p<0.01).

Figure 11A:
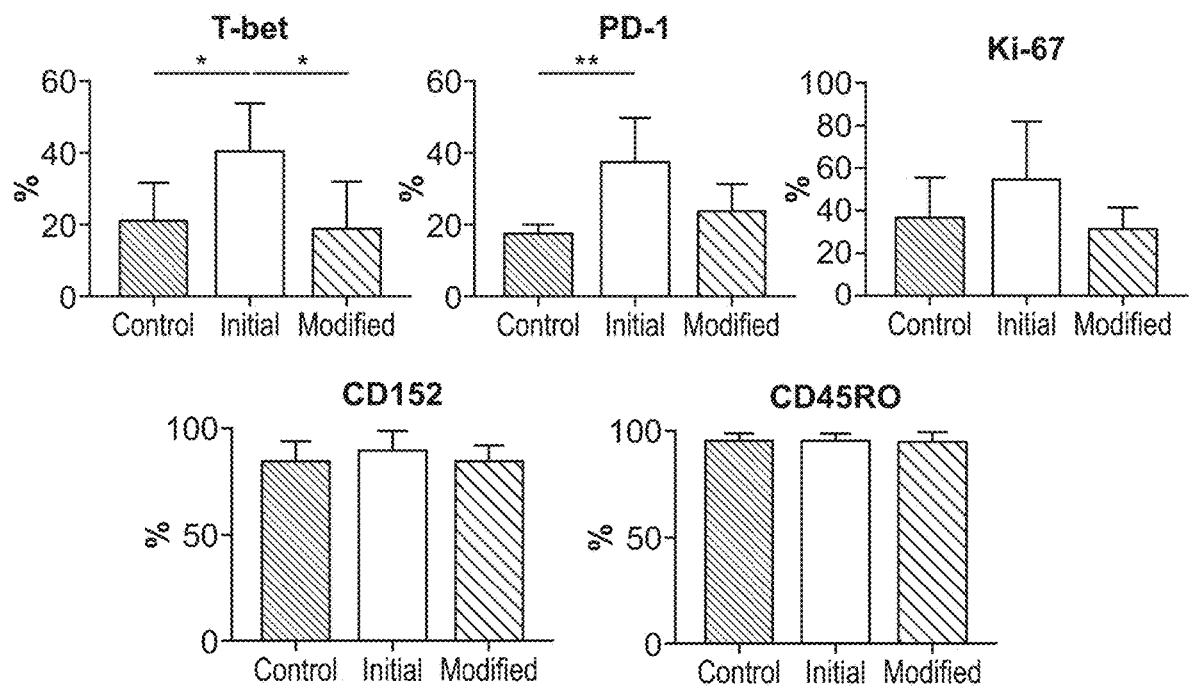
FIG. 11 illustrates Treg characteristics at day 60 post-HCT and Treg TCR repertoire diversity at day 90 post-HCT.
Figure 11B:
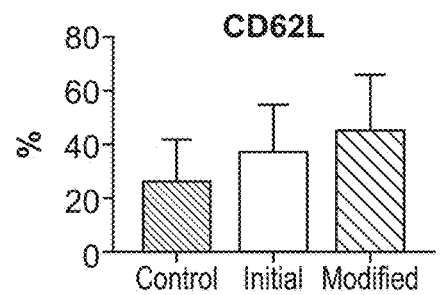

Patients treated on the modified protocol with fresh Treg appeared to have comparable immune reconstitution in percentage and absolute value of Treg following HCT as compared to standard of care controls who had not developed acute or chronic GVHD (two-tailed student T test, p=0.01). Phenotypic characterization of Treg by flow cytometry showed no statistical differences in the expression of surface receptors CTLA-4, PD-1, CD62L, CD45 RO or FOXP3. This was confirmed by CyTOF with the additional observation that there appeared to be no increases in intracellular IFN-γ, TNF-α expression ex vivo and without stimulation. FIG. 11A illustrates characteristics of Tregs (gated on CD4+CD25+CD127dim) as quantified by flow cytometry on day 60 post-HCT. FIG. 11B illustrates characteristics of Tregs (gated on CD4+CD25+CD127dim) as quantified by CyTOF on day 60 post-HCT.

Treg TCR Repertoire Analysis

In order to assess TCR repertoire reconstitution of the Treg compartment following HCT, FACS was used to purify CD4+CD25+CD127dim Treg from patients at ~day 90 post-transplant. For TCR repertoire analysis, Treg were enriched from PBMCs of patients by a two-step isolation procedure: CD25+ cells were isolated from PBMCs using CD25 Microleads II(Miltenyi Biotech) following the manufacturer's instructions. After staining with anti-CD3 (OKT3, BioLegend), -CD4 (OKT4, BioLegend), -CD8 (RPA-T8, BioLegend), -CD25 (BC96, BioLegend) and -CD127 (A019D5, BioLegend) antibodies, CD3+, CD4+, CD8-, CD25+, CD127dim cells were isolated, lysed by TRIzol® Plus reagent and stored at −80° C. Between 2,700-48,000 Treg cells were isolated.

Figure 11C:
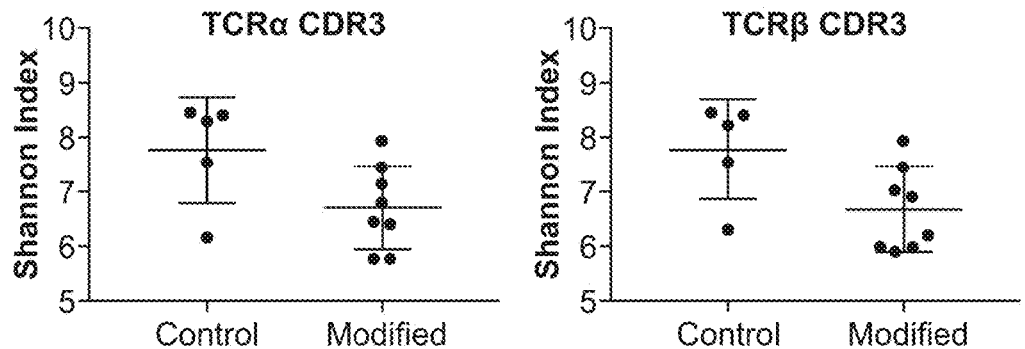

Using RNA as a template, TCR Rep-Seq was performed using 5'RACE methodology with modified gene specific primers in the TCRA or TCRB constant region. The purified 5'RACE PCR products were processed to make sequencing libraries using the KAPA Hyper Prep kit. Sequencing was performed using an Illumina MiSeq reagent 500-cycle V2 kit by paired-end 250×2 cycles. The paired-end reads from the MiSeq were submitted to MixCR for TCRA and TCRB rearrangement analyses. The unique CDR3 amino acid sequences (CDR3 clones) for each sample were summarized based on the MixCR results. Single-copy CDR3 clones were removed. The frequency of a clonotype was calculated by the copy number of the clonotype divided by the total number of copies of all clonotypes in a sample. Data were subjected to bioinformatics analyses. There were no statistical differences in the diversity of Treg following either standard of care or the modified clinical trial protocol wherein fresh Tregs were administered (FIG. 11C).

What is claimed is:

1. A method of treating a human subject having a hematologic malignancy, comprising:
    (a) administering to the human subject:
        one or more graft versus host disease (GVHD) prophylactic agents;
        a population of cells comprising a dose of $5 \times 10^5$ to $2 \times 10^7$ donor hematopoietic stem and progenitor cells (HSPCs) per kilogram of body weight of the human subject, wherein the HSPCs comprise less than 2% CD3+ cells;
        a population of cells comprising a dose of $1 \times 10^6$ to $5 \times 10^6$ donor regulatory T cells (Tregs) per kilogram of body weight of the human subject, wherein at least 80% of the nucleated cells administered in the population of cells comprising a dose of donor Tregs are FOXP3+ cells; and
        a population of cells comprising a dose of $1 \times 10^6$ to $5 \times 10^6$ donor CD3+ conventional T cells (Tcons) per kilogram of body weight of the human subject, and
    (b) myeloablative conditioning of the human subject prior to the administration of the population of cells comprising a dose of HSPCs, the population of cells comprising a dose of Tregs, and/or the population of cells comprising a dose of Tcons.

2. The method of claim 1, wherein the one or more GVHD prophylactic agents comprise tacrolimus.

3. The method of claim 1, wherein the human subject does not develop a stage 2 or higher GVHD within 30 days of administering the population of Tcons.

4. The method of claim 1, wherein the human subject does not develop chronic GVHD within 100 days of administering the population of Tcons.

5. The method of claim 1, wherein the population of cells comprising a dose of donor HSPCs, the population of cells comprising a dose of Tregs, and/or the population of cells comprising a dose of Tcons is allogeneic to the human subject.

6. The method of claim 1, wherein the human subject exhibits full donor chimerism.

7. The method of claim 1, wherein the method does not require the subject to be treated for GVHD.

8. The method of claim 1, wherein a ratio of Tregs to Tcons administered is between about 1:1 and 1:3.

9. The method of claim 1, wherein the HSPCs are CD34+.

10. The method of claim 1, wherein the Tregs are CD4+ CD25+CD127$^{dim}$.

11. The method of claim 1, wherein peripheral blood of the human subject exhibits a donor engraftment of greater than $1 \times 10^9$ neutrophil cells/L within 20 days of being administered the population of cells comprising a dose of hematopoietic HSPCs.

12. The method of claim 1, wherein the population of cells comprising a dose of HSPCs is obtained from a donor that is HLA-matched to the human subject.

13. The method of claim 1, wherein the population of cells comprising a dose of HSPCs, the population of cells comprising a dose of Tregs, and/or the population of cells comprising a dose of Tcons are administered at different times.

14. The method of claim 1, wherein the population of cells comprising a dose of HSPCs and the population of cells comprising a dose of Tregs are administered at the same time.

15. The method of claim 1, wherein the population of cells comprising a dose of HSPCs is administered as a single dose to the human subject.

16. The method of claim 1, wherein the population of cells comprising a dose of Tregs is administered as a single dose to the human subject.

17. The method of claim 1, wherein the population of cells comprising a dose of Tcons is administered as a single dose to the human subject.

18. The method of claim 1, wherein the population of cells comprising a dose of HSPCs and the population of cells comprising a dose of Tregs are not cryopreserved.

19. The method of claim 1, wherein the population of cells comprising a dose of Tcons is administered at least 12 hours after administration of the population of cells comprising a dose of Tregs and/or the population of cells comprising a dose of HSPCs.

20. The method of claim 1, wherein the hematologic malignancy is selected from the group consisting of: acute lymphocytic leukemia (ALL), acute myelogenous leukemia (AML), chronic myelogenous leukemia (CML), multiple myeloma, Hodgkin's lymphoma, and non-Hodgkin's lymphoma.

21. The method of claim 20, wherein the hematologic malignancy is in remission for at least 1 year after the administration of the of population of cells comprising a dose of HSPCs, the population of cells comprising a dose of Tregs and/or the population of cells comprising a dose of Tcons.

22. The method of claim 1, wherein the myeloablative conditioning comprises administration of one or more of total body irradiation, cyclophosphamide, etoposide, and busulfan.

\* \* \* \* \*